US011364306B2

(12) United States Patent
Shayakhmetov et al.

(10) Patent No.: US 11,364,306 B2
(45) Date of Patent: Jun. 21, 2022

(54) DETARGETED ADENOVIRUS VARIANTS AND RELATED METHODS

(71) Applicant: ADCURE BIOTECHNOLOGIES, LLC., Snellville, GA (US)

(72) Inventors: Dmitry M. Shayakhmetov, Snellville, GA (US); Nelson C. Di Paolo, Avondale Estates, GA (US)

(73) Assignee: ADCURE BIOTECHNOLOGIES, LLC, Snellville, GA (US)

( * ) Notice: Subject to any disclaimer, the term of this patent is extended or adjusted under 35 U.S.C. 154(b) by 387 days.

(21) Appl. No.: 16/460,160

(22) Filed: Jul. 2, 2019

(65) Prior Publication Data

US 2019/0388487 A1 Dec. 26, 2019

Related U.S. Application Data

(63) Continuation of application No. 15/537,392, filed as application No. PCT/US2016/013765 on Jan. 17, 2016, now Pat. No. 10,376,549.

(60) Provisional application No. 62/105,284, filed on Jan. 20, 2015.

(51) Int. Cl.
| | |
|---|---|
| *A61K 48/00* | (2006.01) |
| *A61K 35/76* | (2015.01) |
| *C07K 14/005* | (2006.01) |
| *C12N 15/86* | (2006.01) |
| *C12N 7/00* | (2006.01) |
| *A61P 43/00* | (2006.01) |
| *A61K 35/761* | (2015.01) |
| *C07K 14/075* | (2006.01) |
| *C12N 7/06* | (2006.01) |
| *C12N 15/861* | (2006.01) |

(52) U.S. Cl.
CPC ............. *A61K 48/00* (2013.01); *A61K 35/76* (2013.01); *A61K 35/761* (2013.01); *A61P 43/00* (2018.01); *C07K 14/005* (2013.01); *C07K 14/075* (2013.01); *C12N 7/00* (2013.01); *C12N 7/06* (2013.01); *C12N 15/86* (2013.01); *C12N 15/8616* (2013.01); *C12N 2710/00043* (2013.01); *C12N 2710/00061* (2013.01); *C12N 2710/10021* (2013.01); *C12N 2710/10322* (2013.01); *C12N 2710/10332* (2013.01); *C12N 2710/10333* (2013.01); *C12N 2710/10334* (2013.01); *C12N 2710/10345* (2013.01); *C12N 2810/405* (2013.01)

(58) Field of Classification Search
None
See application file for complete search history.

(56) References Cited

U.S. PATENT DOCUMENTS

| 2006/0281090 A1 | 12/2006 | Lieber |
| 2011/0104788 A1 | 5/2011 | Baker et al. |
| 2011/0189234 A1 | 8/2011 | Van Beusechem et al. |

FOREIGN PATENT DOCUMENTS

| JP | 2004-290018 | 10/2004 |
| WO | 92/14755 | 9/1992 |
| WO | 00/15823 | 3/2000 |
| WO | 2002/081497 | 10/2002 |
| WO | 03/029448 | 4/2003 |
| WO | 92/14755 | 10/2014 |

OTHER PUBLICATIONS

Bradshaw, A.C., et al., "Biodistribution and inflammatory profiles of novel penton and hexon double-mutant serotype 5 adenoviruses", Journal of Controlled Release, 164(2012) 394-402.
Khare, R., et al., "Identification of Adenovirus Serotype 5 Hexon Regions That Interact with Savenger Receptors", Journal of Virology, Feb. 2012, vol. 86(4), pp. 2293-2303.
U.S. Appl. No. 15/357,392, filed Jun. 16, 2017, Patented.
Communication pursuant to Article 94(3) EPC issued in European Application No. 16 740 545.5, dated Oct. 17, 2019.
Extended European Search Report dated May 14, 2018 in European Application No. EP 16 74 0545.
Bradshaw, A. C. et al., "Biodistribution and inflammatory profiles of novel penton and hexon-double-mutant serotype 5 adenoviruses", Journal of Controlled Release, Dec. 28, 2012, 164, pp. 394-402.
Atasheva, S. et al., "Adenovirus Variant with Defined Set of Genetic Mutations in the Penton and Hexon Escapes Liver Sequenstration Afer Intravasuclar Administration", Molecular Therapy, May 2015, vol. 23.
Koizumi, N. et al., "Reduction of Natural Adenovirus Tropism to Mouse Liver by Fiber-Shaft Exchange in Combination with both CAR-and av Integrin-Binding Ablation", Dec. 1, 2003, vol. 77, No. 24, p. 13062-13072.
Zhang, Y. et al., "Adenovirus Receptors", Journal of Virology, Oct. 2005, vol. 79, No. 19, pp. 12125-12131.

*Primary Examiner* — Marcia S Noble
(74) *Attorney, Agent, or Firm* — Michael Ye; Rimon Law

(57) ABSTRACT

The present disclosure describes the generation and the use of Ad variants (Ad) possessing any combination of mutations in genes that code for the hexon, penton, fiber, and non-structural proteins, where simultaneous modification of hexon and penton are made to avoid the trapping of Ad in the liver and to reduce toxicity after intravascular virus administration. Such liver de-targeted Ad can be useful tool for selective and specific gene delivery to extra-hepatic tissues and cells, including disseminated metastatic cancer cells.

13 Claims, 34 Drawing Sheets

Specification includes a Sequence Listing.

*FIG. 11A*

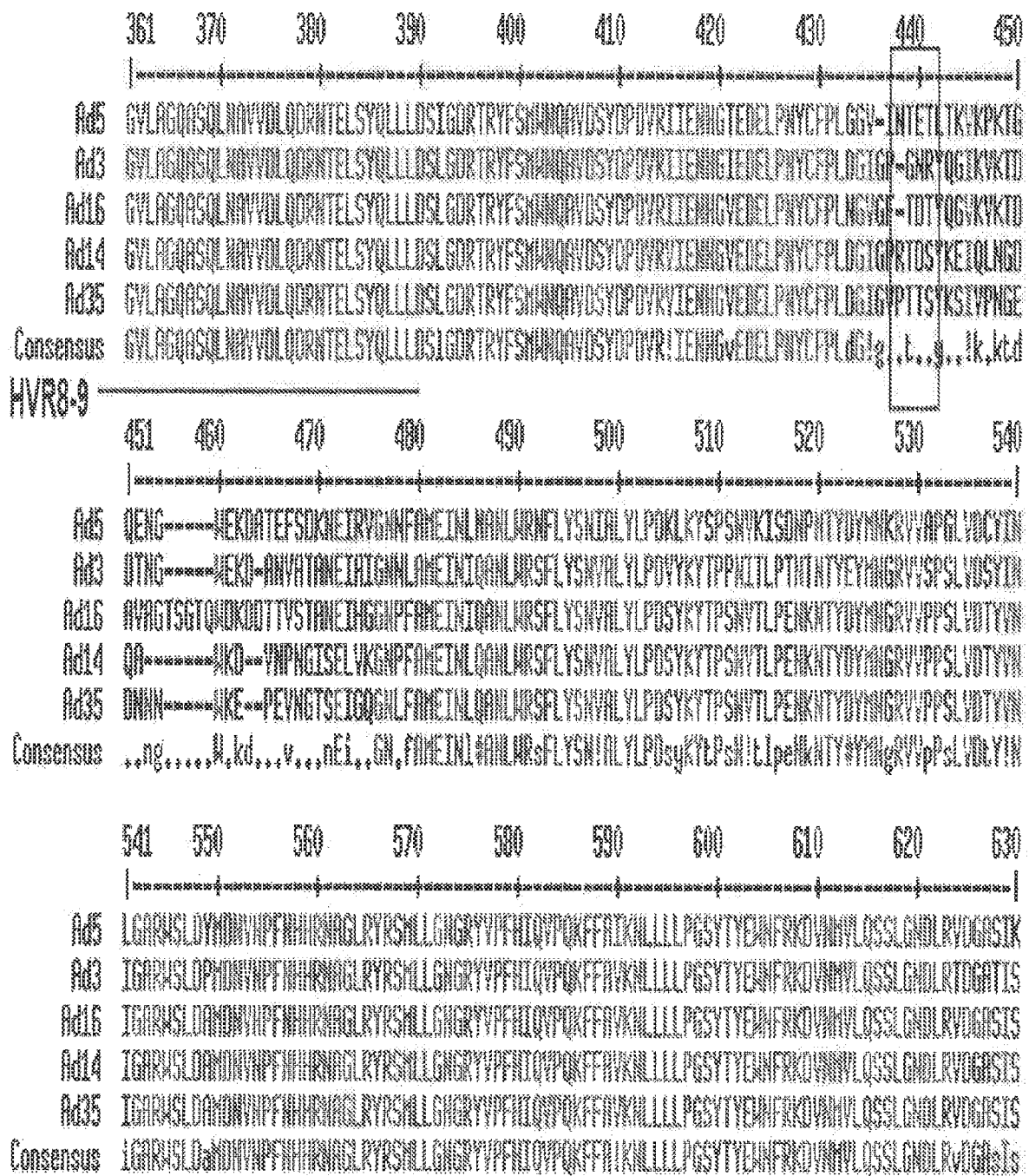
FIG. 11A, continued

```
               631       640       650       660       670       680       690       700       710       720
                |---------+---------+---------+---------+---------+---------+---------+---------+---------|
          Ad5  FDSICLYATFFPMAHNTASTLEAMLRNDTNDQSFNDYLSAANMLYPIPANATNVPISIPSRNWAAFRGHAFTRLKTKETPSLGSGYDPYY
          Ad3  FTSINLYATFFPMAHNTASTLEAMLRNDTNDQSFNDYLSAANMLYPIPANATNIPISIPSRNWAAFRGHSFTRLKTKETPSLGSGFDPYF
         Ad16  FTSINLYATFFPMAHNTASTLEAMLRNDTNDQSFNDYLSAANMLYPIPANATNIPISIPSRNWAAFRGHSFTRLKTKETPSLGSGFDPYF
         Ad14  FTSINLYATFFPMAHNTASTLEAMLRNDTNDQSFNDYLSAANMLYPIPANATNIPISIPSRNWAAFRGHSFTRLKTKETPSLGSGFDPYF
         Ad35  FTSINLYATFFPMAHNTASTLEAMLRNDTNDQSFNDYLSAANMLYPIPANATNIPISIPSRNWAAFRGHSFTRLKTKETPSLGSGFDPYF
    Consensus  FtSInLYATFFPMAHNTASTLEAMLRNDTNDQSFNDYLSAANMLYPIPANATNiPISIPSRNWAAFRGHsFTRLKTKETPSLGSGxDPYx 721       730       740       750       760       770       780       790       800       810
                |---------+---------+---------+---------+---------+---------+---------+---------+---------|
          Ad5  TYSGSIPYLDGTFYLNHTFKKVAITFDSSVSHPGNDRLLTPNEFEIKRSVDGEGYNVAQCNMTKDHFLVQMLANYNIGYQGFYIPESYKD
          Ad3  VYSGSIPYLDGTFYLNHTFKKVSINFDSSVSHPGNDRLLSPNEFEIKRTVDGEGYNVAQCNMTKDHFLVQMLANYNIGYQGFYIPEGYKD
         Ad16  VYSGSIPYLDGTFYLNHTFKKVSINFDSSVSHPGNDRLLSPNEFEIKRTVDGEGYNVAQCNMTKDHFLVQMLANYNIGYQGFYIPEGYKD
         Ad14  VYSGSIPYLDGTFYLNHTFKKVSINFDSSVSHPGNDRLLSPNEFEIKRTVDGEGYNVAQCNMTKDHFLVQMLANYNIGYQGFYIPEGYKD
         Ad35  VYSGSIPYLDGTFYLNHTFKKVSINFDSSVSHPGNDRLLSPNEFEIKRTVDGEGYNVAQCNMTKDHFLVQMLANYNIGYQGFYIPEGYKD
    Consensus  vYSGSIPYLDGTFYLNHTFKKVsInFDSSVSHPGNDRLLsPNEFEIKRtVDGEGYNVAQCNMTKDHFLVQMLANYNIGYQGFYIPEgYKD 811       820       830       840       850       860       870       880       890       900
                |---------+---------+---------+---------+---------+---------+---------+---------+---------|
          Ad5  RMYSFFRNFQPMSRQVVDDTKYKDYQQVGILHQHNNSGFVGYLAPTMREGQAYPANFPYPLIGKTAVDSITQKKFLCDRTLWRIPFSSNF
          Ad3  RMYSFFRNFQPMSRQVVDEYNYTDYKAVTLPYQHNNSGFVGYLAPTMRQGEPYPANYPYPLIGTTAVKSVTQKKFLCDRTMWRIPFSSNF
         Ad16  RMYSFFRNFQPMSRQVVDEYNYTDYKAVTLPYQHNNSGFVGYLAPTMRQGEPYPANYPYPLIGTTAVKSVTQKKFLCDRTMWRIPFSSNF
         Ad14  RMYSFFRNFQPMSRQVVDEYNYKDFKAVAIPYQHNNSGFVGYMAPTMRQGQPYPANYPYPLIGTTAVNSVTQKKFLCDRTMWRIPFSSNF
         Ad35  RMYSFFRNFQPMSRQVVDEYNYKDFKAVAIPYQHNNSGFVGYMAPTMRQGQPYPANYPYPLIGTTAVNSVTQKKFLCDRTMWRIPFSSNF
    Consensus  RMYSFFRNFQPMSRQVVDxvnYkDxkaV.ipyQHNNSGFVGYxAPTMRxGxpYPANxPYPLIGtTAV.SITQKKFLCDRTxWRIPFSSNF 901       910       920       930       940       950       960       970873
                |---------+---------+---------+---------+---------+---------+---------+---|
          Ad5  MSNGALTDLGQNLLYANSAHALDMTFEVDPMDEPTLLYVLFEVFDVVRVHRPHRGVIETVYLRTPFSAGNATT
          Ad3  MSNGALTDLGQNMLYANSAHALDMTFEVDPMDEPTLLYLLFEVFDVVRVHQPHRGVIEAVYLRTPFSAGNATT
         Ad16  MSNGALTDLGQNLLYANSAHALDMTFEVDPMDEPTLLYLLFEVFDVVRVHQPHRGVIEAVYLRTPFSAGNATT
         Ad14  MSNGALTDLGQNMLYANSAHALDMTFEVDPMDEPTLLYLLFEVFDVVRVHQPHRGIIETVYLRTPFSAGNATT
         Ad35  MSNGALTDLGQNMLYANSAHALDMTFEVDPMDEPTLLYLLFEVFDVVRVHQPHRGIIEAVYLRTPFSAGNATT
    Consensus  MSNGALTDLGQNxLYANSAHALDMTFEVDPMDEPTLLYlLFEVFDVVRVHqPHRGiIEaVYLRTPFSAGNATT
```

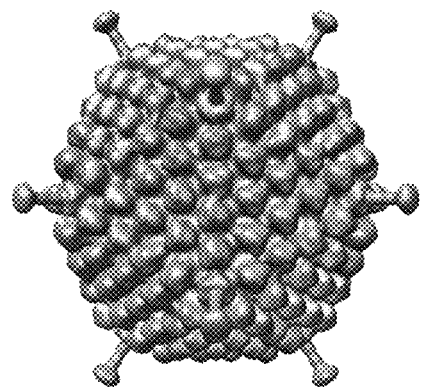

FIG. 12B

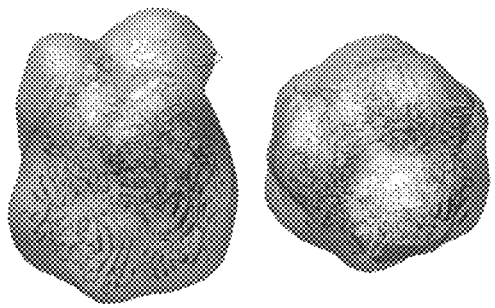

FIG. 12C

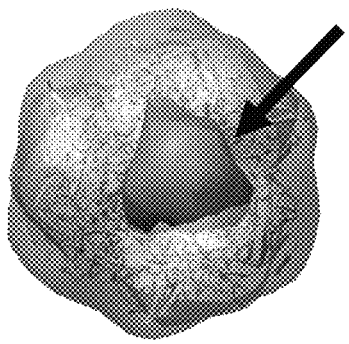

FIG. 12D

|  | HVR3 SITE |  | HVR7 SITE |  |
|---|---|---|---|---|
| Ad5  | QIGESQWYETEIN--HA | 219 | LGGVI-NTETLTKVKPK | 432 |
| Ad16 | QVGNASWVDANGTEEKY | 204 | LNGVG-FTDTYQGVKVK | 415 |
| Ad2  | QIGESQWNEADAN--AA | 230 | LGGIG-VTDTYQAIKAN | 444 |
| Ad21 | QVGDETWTDTDGTTEKY | 219 | LDGVGVPISSYKIIEPN | 432 |
| Ad41 | QVGQTQWNSEVGAAQKV | 198 | LGGSA-ATDTYSGIKAN | 408 |
| Ad4  | QVGND SWVDTNGAEEKY | 204 | LNGVG-LTDTYQGVKVK | 415 |
| Ad3  | QVGEESWTDTDVTNEKF | 210 | LDGIG-PGNRYQGIKVK | 425 |
| Ad35 | QVGDETWTDLDGKTEEY | 222 | LDGIGVPTTSYKSIVPN | 434 |
| Ad51 | QVGEENWQETFN---FY | 205 | LDGSG-TNAAYQGVKVT | 423 |
| Ad9  | QVGEENLQDVEN---YY | 205 | LDGAG-TNATYQGVKVK | 421 |
| Ad50 | QVGEESWTDTDGTDEKY | 212 | LDGVGPRIDSYKGIETN | 422 |
|  | *** |  | *** |  |

Table 1. Affinity of FX binding to different viruses

| Virus | Immobilized RU | Kd, nM |
|---|---|---|
| Adenovirus | | |
| Ad5 | 384 | 0.229 |
| Ad16 | 470 | 1.67 |
| Ad2 | 352 | 52.9 |
| Ad21 | 615 | 410 |
| Ad41 | 347 | 630 |
| Ad4 | 2900 | 2480 |
| Ad3 | 2973 | 3000 |
| Ad35 | 315 | No binding |
| Ad51 | 667 | No binding |
| Ad9 | 311 | No binding |
| Ad50 | 266 | No binding |
| | | |
| Reovirus | | |
| T3D | 486 | No binding |
| | | |
| Ad5-sCAR+ | | 7.9 |
| Ad9-sCAR+ | | 6400 |
| Ad12-sCAR+ | | 15 |
| Ad41L-sCAR+ | | 7.3 |

FIG. 12D, continued

| | |
|---|---|
| Ad2 penton base | MQRAAMYE------EGPPPSYESVVSAAPVAAALGSPFDAPLDPPFVPPRYLRPTGGENSIRYSELAPLYDTTRVYLVDNKSTDV 79 |
| Ad3 penton base | MRRRAVLGGAVVYPEGPPPSYESVMQQQ--AAMI----QPPLEAPFVPPRYLAPTEGRNSIRYSDVSPLYDTTKLYLVDNKSADI 79 |
| Ad7 penton base | MRRRAVLGGAMVYPEGPPPSYESVMQQQ--AAMI----QPPLEAPFVPPRYLAPTEGRNSIRYSELSPLYDTTKLYLVDNKSADI 79 |
| Ad11 penton base | -MRRVVLGGAVVYPEGPPPSYESVMQQQQATAVM----QSPLEAPFVPPRYLAPTEGRNSIRYSELAPQYDTTRLYLVDNKSADI 80 |
| Ad41 penton base | MRRAVGVPPVMAYAEGPPPSYESVMGSADSPATL---------EALYVPPRYLGPTEGRNSIRYSELAPLYDTTRVYLVDNKSADI 77 |
| Ad12 penton base | -MRRAVELQTVAPPETPPPSYETVMAAA----------------PPYVPPRYLGPTEGRNSIRYSELSPLYDTTRVYLVDNKSSDI 69 |
| Ad17 penton base | -MRR-------AVVSSSPPPSYESVMAQA------------TLEVPFVPPRYMAPTEGRNSIRYSELAPLYDTTRVYLVDNKSADI 66 |
| Ad25 penton base | MMER-------AYPEGPPPSYESVMQQAMAAAAM----QPPLEAPYVPPRYLAPTEGRNSIRYSELAPLYDTTRLYLVDNKSADI 74 |
| Ad37 penton base | -MRR-------AVVSSSPPPSYESVMAQA------------TLEVPFVPPRYMAPTEGRNSIRYSELAPLYDTTRVYLVDNKSADI 66 |

Wild type Ad5 penton base RGD-containing loop

DAYQAS - LLKDDT EQGGGGAGGS NSSGSGAEENSNAAAAAMQPVEDM
NDHAIRGDTFATRAEEKRAEAEAAAEAAAPAAQPEV EKP - QKKPVIK PLTEDSKKRS

RGD-motif-deleted penton base

DAYQAS - LLKDDT EQGGGGAGGS NSSGSGAEENSNAAAAAMQPVEDM

NDHAI TFATRAEEKRAEAEAAAEAAAPAAQPEV EKP - QKKPVIK PLTEDSKKRS

Design of Ad5 Penton-modified Viruses

```
           323                                          356
Ad5-GFP    N A A A A A N Q P V E D R N D H A I R G D T F A T R A E - - - - - -
dRGD       N A A A A A N Q P V E D N N D H A I - - - T F A T R A E - - - - - -
Lam1       N A A A S G T K L L I S Q A R K Q A A S I K V A V S A G R G - - - -
Lam3       A A A A S G T R E L I Q A R D A A S E V A V P H R F N G K S G V E V
           357                                                          391
Ad5-GFP    - - - - - - E K R A E A E A A A E A A A P A A Q P E V E K P Q K K P V
dRGD       - - - - - - E K R A E A E A A A E A A A P A A Q P E V E K P Q K K P V
Lam1       - - - - - I R A V D P Q I S S T N Y N T L T G S T G G A K P Q K K P V
Lam3       R L P N D L E D L F G Y T S L S L G S T G G A P E V E K P Q K K P V
```

*FIG. 20*

Ad-3M
1. Penton RGD-loop Lam substitution
2. Hexon HVR1 deletion
3. Hexon HVR7 T425A IL-1α
IL-1β
MIP-2
KC
MCP-1
IL-6
TNF-α
IP-10
Pos.C

CD68 + PI

Wild type Ad5 penton base RGD-containing loop

DAYQAS - LLKDDT EQGGGGAGGS NSSGSGAEENSNAAAAAMQPVEDM
NDHAIRGDTFATRAEEKRAEAEAAAEAAAPAAQPEV EKP - QKKPVIK PLTEDSKKRS

↓ RGD-motif-deleted penton base

DAYQAS - LLKDDT EQGGGGAGGS NSSGSGAEENSNAAAAAMQPVEDM

NDHAI TFATRAEEKRAEAEAAAEAAAPAAQPEV EKP - QKKPVIK PLTEDSKKRS

*FIG. 25A*

Wild type Ad5 penton base RGD-containing loop

DAYQAS - LLKDDT EQGGGGAGGS NSSGSGAEENSNAAAAAMQPVEDM
NDHAIRGDTFATRAEEKRAEAEAAAEAAAPAAQPEV EKP - QKKPVIK PLTEDSKKRS

↓ RGD-Loop-mutated penton base

DAYQAS - LLKDDT EQGGGG EQGGGGAGGS NSSGSGAEEN
SNAAAAAMGSG CNGQGEQC AAAEAAAPAAQPEV EKP - QKKPVIK
PLTEDSKKRS
  └─► α3β1-integrin-binding peptide DAYQAS - LLKDDT EQGGGG EQGGGGAGGS NSSGSGAEEN
SNAAAAAMGSG RKKRRQRRR AAAEAAAPAAQPEV EKP - QKKPVIK
PLTEDSKKRS
  └─► αvβ5-integrin-binding peptide

*FIG. 25B*

SEQUENCE LISTING

```
<160> NUMBER OF SEQ ID NOS: 71

<210> SEQ ID NO 1
<211> LENGTH: 16
<212> TYPE: PRT
<213> ORGANISM: Human adenovirus serotype 5
<220> FEATURE:
<221> NAME/KEY: misc_feature
<223> OTHER INFORMATION: Adeno 5 WT fragment of HVR7

<400> SEQUENCE: 1

Leu Gly Gly Val Ile Asn Thr Glu Thr Leu Thr Lys Val Lys Pro Lys
1               5                   10                  15

<210> SEQ ID NO 2
<211> LENGTH: 16
<212> TYPE: PRT
<213> ORGANISM: Human adenovirus serotype 5
<220> FEATURE:
<221> NAME/KEY: misc_feature
<223> OTHER INFORMATION: Adeno 5-TEA mutant fragment of HVR7

<400> SEQUENCE: 2
```

```
Leu Gly Gly Val Ile Asn Thr Glu Ala Leu Thr Lys Val Lys Pro Lys
1               5                   10                  15
```

<210> SEQ ID NO 3
<211> LENGTH: 61
<212> TYPE: PRT
<213> ORGANISM: Artificial Sequence
<220> FEATURE:
<223> OTHER INFORMATION: Adeno 5 penton-human laminin 1 chimera

<400> SEQUENCE: 3

```
Asn Ala Ala Ala Ser Gly Thr Lys Leu Leu Ile Ser Gln Ala Arg Lys
1               5                   10                  15

Gln Ala Ala Ser Ile Lys Val Ala Val Ser Ala Asp Arg Asp Cys Ile
            20                  25                  30

Arg Ala Tyr Gln Pro Gln Ile Ser Ser Thr Asn Tyr Asn Thr Leu Thr
        35                  40                  45

Gly Ser Thr Gly Gly Ala Lys Pro Gln Lys Lys Pro Val
    50                  55                  60
```

<210> SEQ ID NO 4
<211> LENGTH: 68
<212> TYPE: PRT
<213> ORGANISM: Artificial Sequence
<220> FEATURE:
<223> OTHER INFORMATION: Adeno 5 penton-human laminin 3 chimera

<400> SEQUENCE: 4

```
Asn Ala Ala Ala Ser Gly Thr Arg Glu Leu Ile Gln Ala Arg Asp Ala
1               5                   10                  15

Ala Ser Lys Val Ala Val Pro Met Arg Phe Asn Gly Lys Ser Gly Val
            20                  25                  30

Glu Val Arg Leu Pro Asn Asp Leu Glu Asp Leu Lys Gly Tyr Thr Ser
        35                  40                  45

Leu Ser Leu Gly Ser Thr Gly Gly Ala Pro Glu Val Glu Lys Pro Gln
    50                  55                  60

Lys Lys Pro Val
65
```

<210> SEQ ID NO 5
<211> LENGTH: 14
<212> TYPE: PRT
<213> ORGANISM: Artificial Sequence
<220> FEATURE:
<223> OTHER INFORMATION: Adeno 5 hexon HVR1 mutation - 1

<400> SEQUENCE: 5

```
Glu Trp Asp Ser Ala Ala Thr Ser Thr Ala Gly Gly Thr His
1               5                   10
```

<210> SEQ ID NO 6
<211> LENGTH: 12
<212> TYPE: PRT
<213> ORGANISM: Artificial Sequence
<220> FEATURE:
<223> OTHER INFORMATION: Adeno 5 hexon HVR1 mutation - 2

<400> SEQUENCE: 6

```
Asp Glu Ala Ala Thr Gly Gly Ser Gly Gln Gln Lys
1               5                   10
```

<210> SEQ ID NO 7
<211> LENGTH: 6

```
<212> TYPE: PRT
<213> ORGANISM: Artificial Sequence
<220> FEATURE:
<223> OTHER INFORMATION: Adeno 5/41 hexon HVR1 chimera

<400> SEQUENCE: 7

Trp Lys Asp Asn Asn Lys
1               5

<210> SEQ ID NO 8
<211> LENGTH: 15
<212> TYPE: PRT
<213> ORGANISM: Artificial Sequence
<220> FEATURE:
<223> OTHER INFORMATION: Adeno 5/51 hexon HVR1 chimera

<400> SEQUENCE: 8

Trp Glu Gln Lys Lys Thr Thr Gly Gly Asn Asp Met Glu Thr His
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Adeno 5 penton chimera - 1

<400> SEQUENCE: 9

Met Gly Ser Gly Cys Asn Gly Gln Gly Glu Gln Cys Ala Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Adeno 5 penton chimera - 2

<400> SEQUENCE: 10

Met Gly Ser Gly Arg Lys Lys Arg Arg Gln Arg Arg Ala Ala Ala
1               5                   10                  15

<210> SEQ ID NO 11
<211> LENGTH: 609
<212> TYPE: PRT
<213> ORGANISM: Artificial Sequence
<220> FEATURE:
<223> OTHER INFORMATION: Synthetic: Ad5

<400> SEQUENCE: 11

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110
```

```
Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
130                 135                 140

Asn Leu Glu Glu Glu Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
                180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
        210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Asn Gly
                245                 250                 255

Lys Leu Glu Ser Gln Val Glu Met Gln Phe Phe Ser Thr Thr Glu Ala
        260                 265                 270

Ala Ala Gly Asn Gly Asp Asn Leu Thr Pro Lys Val Val Leu Tyr Ser
        275                 280                 285

Glu Asp Val Asp Ile Glu Thr Pro Asp Thr His Ile Ser Tyr Met Pro
290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
                340                 345                 350

Ser Gln Leu Asn Ala Val Val Asp Leu Gln Asp Arg Asn Thr Glu Leu
        355                 360                 365

Ser Tyr Gln Leu Leu Asp Ser Ile Gly Asp Arg Thr Arg Tyr Phe
        370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
                420                 425                 430

Thr Gly Gln Glu Asn Gly Trp Glu Lys Asp Ala Thr Glu Phe Ser Asp
                435                 440                 445

Lys Asn Glu Ile Arg Val Gly Asn Asn Phe Ala Met Glu Ile Asn Leu
450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
                500                 505                 510

Leu Val Asp Cys Tyr Ile Asn Leu Gly Ala Arg Trp Ser Leu Asp Tyr
                515                 520                 525
```

```
Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Lys
```

<210> SEQ ID NO 12
<211> LENGTH: 601
<212> TYPE: PRT
<213> ORGANISM: Artificial Sequence
<220> FEATURE:
<223> OTHER INFORMATION: Synthetic: Ad3

<400> SEQUENCE: 12

```
Met Ala Thr Pro Ser Met Met Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Met Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Asp Asn Ala
    130                 135                 140

Val Thr Thr Thr Thr Asn Thr Phe Gly Ile Ala Ser Met Lys Gly Asp
145                 150                 155                 160

Asn Ile Thr Lys Glu Gly Leu Gln Ile Gly Lys Asp Ile Thr Thr Thr
                165                 170                 175

Glu Gly Glu Glu Lys Pro Ile Tyr Ala Asp Lys Thr Tyr Gln Pro Glu
            180                 185                 190

Pro Gln Val Gly Glu Glu Ser Trp Thr Asp Thr Asp Gly Thr Asn Glu
        195                 200                 205

Lys Phe Gly Gly Arg Ala Leu Lys Pro Ala Thr Asn Met Lys Pro Cys
    210                 215                 220

Tyr Gly Ser Phe Ala Arg Pro Thr Asn Ile Lys Gly Gly Gln Ala Lys
225                 230                 235                 240

Asn Arg Lys Val Lys Pro Thr Thr Glu Gly Gly Val Glu Thr Glu Glu
                245                 250                 255

Pro Asp Ile Asp Met Glu Phe Phe Asp Gly Arg Asp Ala Val Ala Gly
            260                 265                 270

Ala Leu Ala Pro Glu Ile Val Leu Tyr Thr Glu Asn Val Asn Leu Glu
```

```
                275                 280                 285
Thr Pro Asp Ser His Val Val Tyr Lys Pro Glu Thr Ser Asn Asn Ser
290                 295                 300
His Ala Asn Leu Gly Gln Gln Ala Met Pro Asn Arg Pro Asn Tyr Ile
305                 310                 315                 320
Gly Phe Arg Asp Asn Phe Val Gly Leu Met Tyr Tyr Asn Ser Thr Gly
                325                 330                 335
Asn Met Gly Val Leu Ala Gly Gln Ala Ser Gln Leu Asn Ala Val Val
            340                 345                 350
Asp Leu Gln Asp Arg Asn Thr Glu Leu Ser Tyr Gln Leu Leu Leu Asp
        355                 360                 365
Ser Leu Gly Asp Arg Thr Arg Tyr Phe Ser Met Trp Asn Gln Ala Val
370                 375                 380
Asp Ser Tyr Asp Pro Asp Val Arg Ile Ile Glu Asn His Gly Ile Glu
385                 390                 395                 400
Asp Glu Leu Pro Asn Tyr Cys Phe Pro Leu Asn Gly Ile Gly Pro Gly
                405                 410                 415
His Thr Tyr Gln Gly Ile Lys Val Lys Thr Asp Asp Thr Asn Gly Trp
            420                 425                 430
Glu Lys Asp Ala Asn Val Ala Pro Ala Asn Glu Ile Thr Ile Gly Asn
        435                 440                 445
Asn Leu Ala Met Glu Ile Asn Ile Gln Ala Asn Leu Trp Arg Ser Phe
450                 455                 460
Leu Tyr Ser Asn Val Ala Leu Tyr Leu Pro Asp Val Tyr Lys Tyr Thr
465                 470                 475                 480
Pro Pro Asn Ile Thr Leu Pro Thr Asn Thr Asn Thr Tyr Glu Tyr Met
                485                 490                 495
Asn Gly Arg Val Val Ser Pro Ser Leu Val Asp Ser Tyr Ile Asn Ile
            500                 505                 510
Gly Ala Arg Trp Ser Leu Asp Pro Met Asp Asn Val Asn Pro Phe Asn
        515                 520                 525
His His Arg Asn Ala Gly Leu Arg Tyr Arg Ser Met Leu Leu Gly Asn
530                 535                 540
Gly Arg Tyr Val Pro Phe His Ile Gln Val Pro Gln Lys Phe Phe Ala
545                 550                 555                 560
Val Lys Asn Leu Leu Leu Leu Pro Gly Ser Tyr Thr Tyr Glu Trp Asn
                565                 570                 575
Phe Arg Lys Asp Val Asn Met Val Leu Gln Ser Ser Leu Gly Asn Asp
            580                 585                 590
Leu Arg Thr Asp Gly Ala Thr Ile Ser
        595                 600

<210> SEQ ID NO 13
<211> LENGTH: 597
<212> TYPE: PRT
<213> ORGANISM: Artificial Sequence
<220> FEATURE:
<223> OTHER INFORMATION: Synthetic: Ad16

<400> SEQUENCE: 13

Met Ala Thr Pro Ser Met Met Pro Gln Trp Ala Tyr Met His Ile Ala
1               5                   10                  15
Gly Gln Asp Ala Ser Glu Tyr Leu Ser Pro Gly Leu Val Gln Phe Ala
            20                  25                  30
Arg Ala Thr Asp Thr Tyr Phe Ser Met Gly Asn Lys Phe Arg Asn Pro
```

```
                35                  40                  45
Thr Val Ala Pro Thr His Asp Val Thr Thr Asp Arg Ser Gln Arg Leu
 50                  55                  60
Met Leu Arg Phe Val Pro Val Asp Arg Glu Asp Asn Thr Tyr Ser Tyr
 65                  70                  75                  80
Lys Val Arg Tyr Thr Leu Ala Val Gly Asp Asn Arg Val Leu Asp Met
                 85                  90                  95
Ala Ser Thr Phe Phe Asp Ile Arg Gly Val Leu Asp Arg Gly Pro Ser
                100                 105                 110
Phe Lys Pro Tyr Ser Gly Thr Ala Tyr Asn Ser Leu Ala Pro Lys Gly
            115                 120                 125
Ala Pro Asn Thr Cys Gln Trp Lys Asp Ser Asp Ser Lys Met His Thr
            130                 135                 140
Phe Gly Val Ala Ala Met Pro Gly Val Thr Gly Lys Lys Ile Glu Ala
145                 150                 155                 160
Asp Gly Leu Pro Ile Gly Ile Asp Ser Thr Ser Gly Thr Asp Thr Val
                165                 170                 175
Ile Tyr Ala Asp Lys Thr Phe Gln Pro Glu Pro Gln Val Gly Asn Ala
                180                 185                 190
Ser Trp Val Asp Ala Asn Gly Thr Glu Glu Lys Tyr Gly Gly Arg Ala
            195                 200                 205
Leu Lys Asp Thr Thr Lys Met Lys Pro Cys Tyr Gly Ser Phe Ala Lys
210                 215                 220
Pro Thr Asn Lys Glu Gly Gln Ala Asn Leu Lys Asp Ser Glu Thr
225                 230                 235                 240
Ala Ala Thr Thr Pro Asn Tyr Asp Ile Asp Leu Ala Phe Phe Asp Asn
                245                 250                 255
Lys Asn Ile Ala Ala Asn Tyr Asp Pro Asp Ile Val Met Tyr Thr Glu
                260                 265                 270
Asn Val Asp Leu Gln Thr Pro Asp Thr His Ile Val Tyr Lys Pro Gly
            275                 280                 285
Thr Glu Asp Thr Ser Ser Glu Ser Asn Leu Gly Gln Gln Ala Met Pro
290                 295                 300
Asn Arg Pro Asn Tyr Ile Gly Phe Arg Asp Asn Phe Ile Gly Leu Met
305                 310                 315                 320
Tyr Tyr Asn Ser Thr Gly Asn Met Gly Val Leu Ala Gly Gln Ala Ser
                325                 330                 335
Gln Leu Asn Ala Val Val Asp Leu Gln Asp Arg Asn Thr Glu Leu Ser
            340                 345                 350
Tyr Gln Leu Leu Leu Asp Ser Leu Gly Asp Arg Thr Arg Tyr Phe Ser
            355                 360                 365
Met Trp Asn Gln Ala Val Asp Ser Tyr Asp Pro Asp Val Arg Ile Ile
            370                 375                 380
Glu Asn His Gly Val Glu Asp Glu Leu Pro Asn Tyr Cys Phe Pro Leu
385                 390                 395                 400
Asn Gly Val Gly Phe Thr Asp Thr Tyr Gln Gly Val Lys Val Lys Thr
                405                 410                 415
Asp Ala Val Ala Gly Thr Ser Gly Thr Gln Trp Asp Lys Asp Asp Thr
            420                 425                 430
Thr Val Ser Thr Ala Asn Glu Ile His Gly Gly Asn Pro Phe Ala Met
            435                 440                 445
Glu Ile Asn Ile Gln Ala Asn Leu Trp Arg Ser Phe Leu Tyr Ser Asn
450                 455                 460
```

```
Val Ala Leu Tyr Leu Pro Asp Ser Tyr Lys Tyr Thr Pro Ser Asn Val
465                 470                 475                 480

Thr Leu Pro Glu Asn Lys Asn Thr Tyr Asp Tyr Met Asn Gly Arg Val
                485                 490                 495

Val Pro Pro Ser Leu Val Asp Thr Tyr Val Asn Ile Gly Ala Arg Trp
            500                 505                 510

Ser Leu Asp Ala Met Asp Asn Val Asn Pro Phe Asn His His Arg Asn
            515                 520                 525

Ala Gly Leu Arg Tyr Arg Ser Met Leu Leu Gly Asn Gly Arg Tyr Val
        530                 535                 540

Pro Phe His Ile Gln Val Pro Gln Lys Phe Phe Ala Val Lys Asn Leu
545                 550                 555                 560

Leu Leu Pro Gly Ser Tyr Thr Tyr Glu Trp Asn Phe Arg Lys Asp
                565                 570                 575

Val Asn Met Val Leu Gln Ser Ser Leu Gly Asn Asp Leu Arg Val Asp
                580                 585                 590

Gly Ala Ser Ile Ser
            595

<210> SEQ ID NO 14
<211> LENGTH: 601
<212> TYPE: PRT
<213> ORGANISM: Artificial Sequence
<220> FEATURE:
<223> OTHER INFORMATION: Synthetic: Ad14

<400> SEQUENCE: 14

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
                20                  25                  30

Arg Ala Thr Asp Thr Tyr Phe Asn Leu Gly Asn Lys Phe Arg Asn Pro
            35                  40                  45

Thr Val Ala Pro Thr His Asp Val Thr Thr Asp Arg Ser Gln Arg Leu
        50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ala Ser Gln Trp Leu Asp Lys Gly Val Glu Thr Thr Glu
    130                 135                 140

Glu Arg Gln Asn Glu Asp Gly Glu Asn Asp Glu Lys Ala Thr Tyr Thr
145                 150                 155                 160

Phe Gly Asn Ala Pro Val Lys Ala Asp Ala Asp Ile Thr Lys Asp Gly
                165                 170                 175

Leu Pro Ile Gly Leu Glu Val Pro Ala Glu Gly Asp Pro Lys Pro Ile
            180                 185                 190

Tyr Ala Asn Lys Leu Tyr Gln Pro Glu Pro Gln Val Gly Gln Glu Ser
        195                 200                 205

Trp Thr Asp Thr Asp Gly Thr Glu Glu Lys Tyr Gly Gly Arg Val Leu
    210                 215                 220
```

Lys Pro Asp Thr Lys Met Lys Pro Cys Tyr Gly Ser Phe Ala Lys Pro
225                 230                 235                 240

Thr Asn Val Lys Gly Gln Ala Lys Val Lys Thr Glu Glu Gly Asn
            245                 250                 255

Asn Ile Glu Tyr Asp Ile Asp Met Asn Phe Phe Asp Leu Arg Ser Gln
                260                 265                 270

Lys Gln Gly Leu Lys Pro Lys Ile Val Met Tyr Ala Glu Asn Val Asp
            275                 280                 285

Leu Glu Ser Pro Asp Thr His Val Val Tyr Lys Pro Glu Val Ser Asp
290                 295                 300

Ala Ser Ser Asn Ala Asn Leu Gly Gln Gln Ser Met Pro Asn Arg Pro
305                 310                 315                 320

Asn Tyr Ile Gly Phe Arg Asp Ile Tyr Gly Leu Met Tyr Tyr Asn Ser
                325                 330                 335

Thr Gly Asn Met Gly Val Leu Ala Gly Gln Ala Ser Gln Leu Asn Ala
            340                 345                 350

Val Val Asp Leu Gln Asp Arg Asn Thr Glu Leu Ser Tyr Gln Leu Leu
355                 360                 365

Leu Asp Ser Leu Gly Asp Arg Thr Arg Tyr Phe Ser Met Trp Asn Gln
370                 375                 380

Ala Val Asp Ser Tyr Asp Pro Asp Val Arg Val Ile Glu Asn His Gly
385                 390                 395                 400

Val Glu Asp Glu Leu Pro Asn Tyr Cys Phe Pro Leu Asp Gly Ile Gly
                405                 410                 415

Pro Arg Thr Asp Ser Tyr Lys Glu Ile Gln Leu Asn Gly Asp Gln Ala
            420                 425                 430

Trp Lys Asp Val Asn Pro Asn Gly Ile Ser Glu Leu Val Lys Gly Asn
435                 440                 445

Pro Phe Ala Met Glu Ile Asn Leu Gln Ala Asn Leu Trp Arg Ser Phe
450                 455                 460

Leu Tyr Ser Asn Val Ala Leu Tyr Leu Pro Asp Ser Tyr Lys Tyr Thr
465                 470                 475                 480

Pro Ser Asn Val Thr Leu Pro Glu Asn Lys Asn Thr Tyr Asp Tyr Met
                485                 490                 495

Asn Gly Arg Val Val Pro Pro Ser Leu Val Asp Thr Tyr Val Asn Ile
            500                 505                 510

Gly Ala Arg Trp Ser Leu Asp Ala Met Asp Asn Val Asn Pro Phe Asn
            515                 520                 525

His His Arg Asn Ala Gly Leu Arg Tyr Arg Ser Met Leu Leu Gly Asn
530                 535                 540

Gly Arg Tyr Val Pro Phe His Ile Gln Val Pro Gln Lys Phe Phe Ala
545                 550                 555                 560

Val Lys Asn Leu Leu Leu Leu Pro Gly Ser Tyr Thr Tyr Glu Trp Asn
                565                 570                 575

Phe Arg Lys Asp Val Asn Met Val Leu Gln Ser Ser Leu Gly Asn Asp
            580                 585                 590

Leu Arg Val Asp Gly Ala Ser Ile Ser
        595                 600

<210> SEQ ID NO 15
<211> LENGTH: 609
<212> TYPE: PRT
<213> ORGANISM: Artificial Sequence
<220> FEATURE:

<223> OTHER INFORMATION: Synthetic: Ad35

<400> SEQUENCE: 15

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Met Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ala Ser Gln Trp Ile Ala Lys Gly Val Pro Thr Ala Ala
    130                 135                 140

Ala Ala Gly Asn Gly Glu Glu His Glu Thr Glu Lys Thr Ala
145                 150                 155                 160

Thr Tyr Thr Phe Ala Asn Ala Pro Val Lys Ala Glu Ala Gln Ile Thr
                165                 170                 175

Lys Glu Gly Leu Pro Ile Gly Leu Glu Ile Ser Ala Glu Asn Glu Ser
            180                 185                 190

Lys Pro Ile Tyr Ala Asp Lys Leu Tyr Gln Pro Glu Pro Gln Val Gly
        195                 200                 205

Asp Glu Thr Trp Thr Asp Leu Asp Gly Lys Thr Glu Glu Tyr Gly Gly
    210                 215                 220

Arg Ala Leu Lys Pro Thr Thr Asn Met Lys Pro Cys Tyr Gly Ser Tyr
225                 230                 235                 240

Ala Lys Pro Thr Asn Leu Lys Gly Gly Gln Ala Lys Pro Lys Asn Ser
                245                 250                 255

Glu Pro Ser Ser Glu Lys Ile Glu Tyr Asp Ile Asp Met Glu Phe Phe
            260                 265                 270

Asp Asn Ser Ser Gln Arg Thr Asn Phe Ser Pro Lys Ile Val Met Tyr
        275                 280                 285

Ala Glu Asn Val Gly Leu Glu Thr Pro Asp Thr His Val Val Tyr Lys
    290                 295                 300

Pro Gly Thr Glu Asp Thr Ser Ser Glu Ala Asn Leu Gly Gln Gln Ser
305                 310                 315                 320

Met Pro Asn Arg Pro Asn Tyr Ile Gly Phe Arg Asp Asn Phe Ile Gly
                325                 330                 335

Leu Met Tyr Tyr Asn Ser Thr Gly Asn Met Gly Val Leu Ala Gly Gln
            340                 345                 350

Ala Ser Gln Leu Asn Ala Val Val Asp Leu Gln Asp Arg Asn Thr Glu
        355                 360                 365

Leu Ser Tyr Gln Leu Leu Leu Asp Ser Leu Gly Asp Arg Thr Arg Tyr
    370                 375                 380

Phe Ser Met Trp Asn Gln Ala Val Asp Ser Tyr Asp Pro Asp Val Arg
385                 390                 395                 400
```

```
Val Ile Glu Asn His Gly Val Glu Asp Glu Leu Pro Asn Tyr Cys Phe
                405                 410                 415

Pro Leu Asp Gly Ile Gly Val Pro Thr Thr Ser Tyr Lys Ser Ile Val
            420                 425                 430

Pro Asn Gly Glu Asp Asn Asn Trp Lys Glu Pro Glu Val Asn Gly
        435                 440                 445

Thr Ser Glu Ile Gly Gln Gly Asn Leu Phe Ala Met Glu Ile Asn Leu
    450                 455                 460

Gln Ala Asn Leu Trp Arg Ser Phe Leu Tyr Ser Asn Val Ala Leu Tyr
465                 470                 475                 480

Leu Pro Asp Ser Tyr Lys Tyr Thr Pro Ser Asn Val Thr Leu Pro Glu
            485                 490                 495

Asn Lys Asn Thr Tyr Asp Tyr Met Asn Gly Arg Val Val Pro Pro Ser
            500                 505                 510

Leu Val Asp Thr Tyr Val Asn Ile Gly Ala Arg Trp Ser Leu Asp Ala
            515                 520                 525

Met Asp Asn Val Asn Pro Phe Asn His His Arg Asn Ala Gly Leu Arg
    530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Val Lys Asn Leu Leu Leu Leu Pro
                565                 570                 575

Gly Ser Tyr Thr Tyr Glu Trp Asn Phe Arg Lys Asp Val Asn Met Val
            580                 585                 590

Leu Gln Ser Ser Leu Gly Asn Asp Leu Arg Val Asp Gly Ala Ser Ile
        595                 600                 605

Ser

<210> SEQ ID NO 16
<211> LENGTH: 343
<212> TYPE: PRT
<213> ORGANISM: Artificial Sequence
<220> FEATURE:
<223> OTHER INFORMATION: Synthetic: Ad5

<400> SEQUENCE: 16

Phe Asp Ser Ile Cys Leu Tyr Ala Thr Phe Phe Pro Met Ala His Asn
1               5                   10                  15

Thr Ala Ser Thr Leu Glu Ala Met Leu Arg Asn Asp Thr Asn Asp Gln
            20                  25                  30

Ser Phe Asn Asp Tyr Leu Ser Ala Ala Asn Met Leu Tyr Pro Ile Pro
        35                  40                  45

Ala Asn Ala Thr Asn Val Pro Ile Ser Ile Pro Ser Arg Asn Trp Ala
    50                  55                  60

Ala Phe Arg Gly Trp Ala Phe Thr Arg Leu Lys Thr Lys Glu Thr Pro
65                  70                  75                  80

Ser Leu Gly Ser Gly Tyr Asp Pro Tyr Tyr Thr Tyr Ser Gly Ser Ile
                85                  90                  95

Pro Tyr Leu Asp Gly Thr Phe Tyr Leu Asn His Thr Phe Lys Lys Val
            100                 105                 110

Ala Ile Thr Phe Asp Ser Ser Val Ser Trp Pro Gly Asn Asp Arg Leu
        115                 120                 125

Leu Thr Pro Asn Glu Phe Glu Ile Lys Arg Ser Val Asp Gly Glu Gly
    130                 135                 140

Tyr Asn Val Ala Gln Cys Asn Met Thr Lys Asp Trp Phe Leu Val Gln
```

```
            145                 150                 155                 160
Met Leu Ala Asn Tyr Asn Ile Gly Tyr Gln Gly Phe Tyr Ile Pro Glu
                165                 170                 175

Ser Tyr Lys Asp Arg Met Tyr Ser Phe Phe Arg Asn Phe Gln Pro Met
            180                 185                 190

Ser Arg Gln Val Val Asp Thr Lys Tyr Lys Asp Tyr Gln Gln Val
        195                 200                 205

Gly Ile Leu His Gln His Asn Asn Ser Gly Phe Val Gly Tyr Leu Ala
        210                 215                 220

Pro Thr Met Arg Glu Gly Gln Ala Tyr Pro Ala Asn Phe Pro Tyr Pro
225                 230                 235                 240

Leu Ile Gly Lys Thr Ala Val Asp Ser Ile Thr Gln Lys Lys Phe Leu
                245                 250                 255

Cys Asp Arg Thr Leu Trp Arg Ile Pro Phe Ser Ser Asn Phe Met Ser
            260                 265                 270

Met Gly Ala Leu Thr Asp Leu Gly Gln Asn Leu Leu Tyr Ala Asn Ser
        275                 280                 285

Ala His Ala Leu Asp Met Thr Phe Glu Val Asp Pro Met Asp Glu Pro
        290                 295                 300

Thr Leu Leu Tyr Val Leu Phe Glu Val Phe Asp Val Val Arg Val His
305                 310                 315                 320

Gln Pro His Arg Gly Val Ile Glu Thr Val Tyr Leu Arg Thr Pro Phe
                325                 330                 335

Ser Ala Gly Asn Ala Thr Thr
            340

<210> SEQ ID NO 17
<211> LENGTH: 343
<212> TYPE: PRT
<213> ORGANISM: Artificial Sequence
<220> FEATURE:
<223> OTHER INFORMATION: Synthetic: Ad3

<400> SEQUENCE: 17

Phe Thr Ser Ile Asn Leu Tyr Ala Thr Phe Phe Pro Met Ala His Asn
1               5                   10                  15

Thr Ala Ser Thr Leu Glu Ala Met Leu Arg Asn Asp Thr Asn Asp Gln
            20                  25                  30

Ser Phe Asn Asp Tyr Leu Ser Ala Ala Asn Met Leu Tyr Pro Ile Pro
        35                  40                  45

Ala Asn Ala Thr Asn Ile Pro Ile Ser Ile Pro Ser Arg Asn Trp Ala
50                  55                  60

Ala Phe Arg Gly Trp Ser Phe Thr Arg Leu Lys Thr Lys Glu Thr Pro
65                  70                  75                  80

Ser Leu Gly Ser Gly Phe Asp Pro Tyr Phe Val Tyr Ser Gly Ser Ile
                85                  90                  95

Pro Tyr Leu Asp Gly Thr Phe Tyr Leu Asn His Thr Phe Lys Lys Val
            100                 105                 110

Ser Ile Met Phe Asp Ser Ser Val Ser Trp Pro Gly Asn Asp Arg Leu
        115                 120                 125

Leu Ser Pro Asn Glu Phe Glu Ile Lys Arg Thr Val Asp Gly Glu Gly
    130                 135                 140

Tyr Asn Val Ala Gln Cys Asn Met Thr Lys Asp Trp Phe Leu Val Gln
145                 150                 155                 160

Met Leu Ala Asn Tyr Asn Ile Gly Tyr Gln Gly Phe Tyr Ile Pro Glu
```

```
            165                 170                 175
Gly Tyr Lys Asp Arg Met Tyr Ser Phe Phe Arg Asn Phe Gln Pro Met
        180                 185                 190

Ser Arg Gln Val Val Asp Glu Val Asn Tyr Thr Asp Tyr Lys Ala Val
    195                 200                 205

Thr Leu Pro Tyr Gln His Asn Asn Ser Gly Phe Val Gly Tyr Leu Ala
210                 215                 220

Pro Thr Met Arg Gln Gly Glu Pro Tyr Pro Ala Asn Tyr Pro Tyr Pro
225                 230                 235                 240

Leu Ile Gly Thr Thr Ala Val Lys Ser Val Thr Gln Lys Lys Phe Leu
            245                 250                 255

Cys Asp Arg Thr Met Trp Arg Ile Pro Phe Ser Ser Asn Phe Met Ser
            260                 265                 270

Met Gly Ala Leu Thr Asp Leu Gly Gln Asn Met Leu Tyr Ala Asn Ser
            275                 280                 285

Ala His Ala Leu Asp Met Thr Phe Glu Val Asp Pro Met Asp Glu Pro
        290                 295                 300

Thr Leu Leu Tyr Leu Leu Phe Glu Val Phe Asp Val Val Arg Val His
305                 310                 315                 320

Gln Pro His Arg Gly Val Ile Glu Ala Val Tyr Leu Arg Thr Pro Phe
                325                 330                 335

Ser Ala Gly Asn Ala Thr Thr
            340

<210> SEQ ID NO 18
<211> LENGTH: 343
<212> TYPE: PRT
<213> ORGANISM: Artificial Sequence
<220> FEATURE:
<223> OTHER INFORMATION: Synthetic: Ad16

<400> SEQUENCE: 18

Phe Thr Ser Ile Asn Leu Tyr Ala Thr Phe Pro Met Ala His Asn
1               5                  10                  15

Thr Ala Ser Thr Leu Glu Ala Met Leu Arg Asn Asp Thr Asn Asp Gln
            20                  25                  30

Ser Phe Asn Asp Tyr Leu Ser Ala Ala Asn Met Leu Tyr Pro Ile Pro
        35                  40                  45

Ala Asn Ala Thr Asn Ile Pro Ile Ser Ile Pro Ser Arg Asn Trp Ala
    50                  55                  60

Ala Phe Arg Gly Trp Ser Phe Thr Arg Leu Lys Thr Lys Glu Thr Pro
65                  70                  75                  80

Ser Leu Gly Ser Gly Phe Asp Pro Tyr Phe Val Tyr Ser Gly Ser Ile
                85                  90                  95

Pro Tyr Leu Asp Gly Thr Phe Tyr Leu Asn His Thr Phe Lys Lys Val
            100                 105                 110

Ser Ile Met Phe Asp Ser Ser Val Ser Trp Pro Gly Asn Asp Arg Leu
        115                 120                 125

Leu Ser Pro Asn Glu Phe Glu Ile Lys Arg Thr Val Asp Gly Glu Gly
    130                 135                 140

Tyr Asn Val Ala Gln Cys Asn Met Thr Lys Asp Trp Phe Leu Val Gln
145                 150                 155                 160

Met Leu Ala Asn Tyr Asn Ile Gly Tyr Gln Gly Phe Tyr Ile Pro Glu
                165                 170                 175

Gly Tyr Lys Asp Arg Met Tyr Ser Phe Phe Arg Asn Phe Gln Pro Met
```

```
                180             185             190
Ser Arg Gln Val Val Asp Glu Val Asn Tyr Thr Asp Tyr Lys Ala Val
            195                 200             205

Thr Leu Pro Tyr Gln His Asn Asn Ser Gly Phe Val Gly Tyr Leu Ala
        210                 215                 220

Pro Thr Met Arg Gln Gly Glu Pro Tyr Pro Ala Asn Tyr Pro Tyr Pro
225                 230                 235                 240

Leu Ile Gly Thr Thr Ala Val Lys Ser Val Thr Gln Lys Lys Phe Leu
            245                 250                 255

Cys Asp Arg Thr Met Trp Arg Ile Pro Phe Ser Ser Asn Phe Met Ser
        260                 265                 270

Met Gly Ala Leu Thr Asp Leu Gly Gln Asn Leu Leu Tyr Ala Asn Ser
            275                 280                 285

Ala His Ala Leu Asp Met Thr Phe Glu Val Asp Pro Met Asp Glu Pro
        290                 295                 300

Thr Leu Leu Tyr Leu Leu Phe Glu Val Phe Asp Val Val Arg Val His
305                 310                 315                 320

Gln Pro His Arg Gly Val Ile Glu Ala Val Tyr Leu Arg Thr Pro Phe
            325                 330                 335

Ser Ala Gly Asn Ala Thr Thr
            340

<210> SEQ ID NO 19
<211> LENGTH: 343
<212> TYPE: PRT
<213> ORGANISM: Artificial Sequence
<220> FEATURE:
<223> OTHER INFORMATION: Synthetic: Ad14

<400> SEQUENCE: 19

Phe Thr Ser Ile Asn Leu Tyr Ala Thr Phe Phe Pro Met Ala His Asn
1               5                   10                  15

Thr Ala Ser Thr Leu Glu Ala Met Leu Arg Asn Asp Thr Asn Asp Gln
            20                  25                  30

Ser Phe Asn Asp Tyr Leu Ser Ala Ala Asn Met Leu Tyr Pro Ile Pro
        35                  40                  45

Ala Asn Ala Thr Asn Ile Pro Ile Ser Ile Pro Ser Arg Asn Trp Ala
50                  55                  60

Ala Phe Arg Gly Trp Ser Phe Thr Arg Leu Lys Thr Lys Glu Thr Pro
65                  70                  75                  80

Ser Leu Gly Ser Gly Phe Asp Pro Tyr Phe Val Tyr Ser Gly Ser Ile
            85                  90                  95

Pro Tyr Leu Asp Gly Thr Phe Tyr Leu Asn His Thr Phe Lys Lys Val
            100                 105                 110

Ser Ile Met Phe Asp Ser Ser Val Ser Trp Pro Gly Asn Asp Arg Leu
        115                 120                 125

Leu Ser Pro Asn Glu Phe Glu Ile Lys Arg Thr Val Asp Gly Glu Gly
        130                 135                 140

Tyr Asn Val Ala Gln Cys Asn Met Thr Lys Asp Trp Phe Leu Val Gln
145                 150                 155                 160

Met Leu Ala Asn Tyr Asn Ile Gly Tyr Gln Gly Phe Tyr Ile Pro Glu
            165                 170                 175

Gly Tyr Lys Asp Arg Met Tyr Ser Phe Phe Arg Asn Phe Gln Pro Met
            180                 185                 190

Ser Arg Gln Val Val Asp Glu Val Asn Tyr Lys Asp Phe Lys Ala Val
```

```
                195                 200                 205
Ala Ile Pro Tyr Gln His Asn Asn Ser Gly Phe Val Gly Tyr Met Ala
            210                 215                 220

Pro Thr Met Arg Gln Gly Gln Pro Tyr Pro Ala Asn Tyr Pro Tyr Pro
225                 230                 235                 240

Leu Ile Gly Thr Thr Ala Val Asn Ser Val Thr Gln Lys Lys Phe Leu
                245                 250                 255

Cys Asp Arg Thr Met Trp Arg Ile Pro Phe Ser Ser Asn Phe Met Ser
            260                 265                 270

Met Gly Ala Leu Thr Asp Leu Gly Gln Asn Met Leu Tyr Ala Asn Ser
        275                 280                 285

Ala His Ala Leu Asp Met Thr Phe Glu Val Asp Pro Met Asp Glu Pro
        290                 295                 300

Thr Leu Leu Tyr Leu Leu Phe Glu Val Phe Asp Val Val Arg Val His
305                 310                 315                 320

Gln Pro His Arg Gly Ile Ile Glu Thr Val Tyr Leu Arg Thr Pro Phe
                325                 330                 335

Ser Ala Gly Asn Ala Thr Thr
            340

<210> SEQ ID NO 20
<211> LENGTH: 343
<212> TYPE: PRT
<213> ORGANISM: Artificial Sequence
<220> FEATURE:
<223> OTHER INFORMATION: Synthetic: Ad35

<400> SEQUENCE: 20

Phe Thr Ser Ile Asn Leu Tyr Ala Thr Phe Phe Pro Met Ala His Asn
1               5                   10                  15

Thr Ala Ser Thr Leu Glu Ala Met Leu Arg Asn Asp Thr Asn Asp Gln
            20                  25                  30

Ser Phe Asn Asp Tyr Leu Ser Ala Ala Asn Met Leu Tyr Pro Ile Pro
        35                  40                  45

Ala Asn Ala Thr Asn Ile Pro Ile Ser Ile Pro Ser Arg Asn Trp Ala
    50                  55                  60

Ala Phe Arg Gly Trp Ser Phe Thr Arg Leu Lys Thr Lys Glu Thr Pro
65                  70                  75                  80

Ser Leu Gly Ser Gly Phe Asp Pro Tyr Phe Val Tyr Ser Gly Ser Ile
                85                  90                  95

Pro Tyr Leu Asp Gly Thr Phe Tyr Leu Asn His Thr Phe Lys Lys Val
            100                 105                 110

Ser Ile Met Phe Asp Ser Ser Val Ser Trp Pro Gly Asn Asp Arg Leu
        115                 120                 125

Leu Ser Pro Asn Glu Phe Glu Ile Lys Arg Thr Val Asp Gly Glu Gly
    130                 135                 140

Tyr Asn Val Ala Gln Cys Asn Met Thr Lys Asp Trp Phe Leu Val Gln
145                 150                 155                 160

Met Leu Ala Asn Tyr Asn Ile Gly Tyr Gln Gly Phe Tyr Ile Pro Glu
                165                 170                 175

Gly Tyr Lys Asp Arg Met Tyr Ser Phe Phe Arg Asn Phe Gln Pro Met
            180                 185                 190

Ser Arg Gln Val Val Asp Glu Val Asn Tyr Lys Asp Phe Lys Ala Val
        195                 200                 205

Ala Ile Pro Tyr Gln His Asn Asn Ser Gly Phe Val Gly Tyr Met Ala
```

```
                210                 215                 220
Pro Thr Met Arg Gln Gly Gln Pro Tyr Pro Ala Asn Tyr Pro Tyr Pro
225                 230                 235                 240

Leu Ile Gly Thr Thr Ala Val Asn Ser Val Thr Gln Lys Lys Phe Leu
                245                 250                 255

Cys Asp Arg Thr Met Trp Arg Ile Pro Phe Ser Ser Asn Phe Met Ser
            260                 265                 270

Met Gly Ala Leu Thr Asp Leu Gly Gln Asn Met Leu Tyr Ala Asn Ser
        275                 280                 285

Ala His Ala Leu Asp Met Thr Phe Glu Val Asp Pro Met Asp Glu Pro
    290                 295                 300

Thr Leu Leu Tyr Leu Leu Phe Glu Val Phe Asp Val Val Arg Val His
305                 310                 315                 320

Gln Pro His Arg Gly Ile Ile Glu Ala Val Tyr Leu Arg Thr Pro Phe
                325                 330                 335

Ser Ala Gly Asn Ala Thr Thr
            340
```

<210> SEQ ID NO 21
<211> LENGTH: 15
<212> TYPE: PRT
<213> ORGANISM: Artificial Sequence
<220> FEATURE:
<223> OTHER INFORMATION: Synthetic: Ad5

<400> SEQUENCE: 21

```
Gln Ile Gly Glu Ser Gln Trp Tyr Glu Thr Glu Ile Asn His Ala
1               5                   10                  15
```

<210> SEQ ID NO 22
<211> LENGTH: 17
<212> TYPE: PRT
<213> ORGANISM: Artificial Sequence
<220> FEATURE:
<223> OTHER INFORMATION: Synthetic: Ad16

<400> SEQUENCE: 22

```
Gln Val Gly Asn Ala Ser Trp Val Asp Ala Asn Gly Thr Glu Glu Lys
1               5                   10                  15

Tyr
```

<210> SEQ ID NO 23
<211> LENGTH: 15
<212> TYPE: PRT
<213> ORGANISM: Artificial Sequence
<220> FEATURE:
<223> OTHER INFORMATION: Synthetic: Ad2

<400> SEQUENCE: 23

```
Gln Ile Gly Glu Ser Gln Trp Asn Glu Ala Asp Ala Asn Ala Ala
1               5                   10                  15
```

<210> SEQ ID NO 24
<211> LENGTH: 17
<212> TYPE: PRT
<213> ORGANISM: Artificial Sequence
<220> FEATURE:
<223> OTHER INFORMATION: Synthetic: Ad21

<400> SEQUENCE: 24

```
Gln Val Gly Asp Glu Thr Trp Thr Asp Thr Asp Gly Thr Thr Glu Lys
1               5                   10                  15
```

Tyr

<210> SEQ ID NO 25
<211> LENGTH: 17
<212> TYPE: PRT
<213> ORGANISM: Artificial Sequence
<220> FEATURE:
<223> OTHER INFORMATION: Synthetic: Ad41

<400> SEQUENCE: 25

Gln Val Gly Gln Thr Gln Trp Asn Ser Glu Val Gly Ala Ala Gln Lys
1               5                   10                  15

Val

<210> SEQ ID NO 26
<211> LENGTH: 17
<212> TYPE: PRT
<213> ORGANISM: Artificial Sequence
<220> FEATURE:
<223> OTHER INFORMATION: Synthetic: Ad4

<400> SEQUENCE: 26

Gln Val Gly Asn Asp Ser Trp Val Asp Thr Asn Gly Ala Glu Glu Lys
1               5                   10                  15

Tyr

<210> SEQ ID NO 27
<211> LENGTH: 17
<212> TYPE: PRT
<213> ORGANISM: Artificial Sequence
<220> FEATURE:
<223> OTHER INFORMATION: Synthetic: Ad3

<400> SEQUENCE: 27

Gln Val Gly Glu Glu Ser Trp Thr Asp Thr Asp Val Thr Asn Glu Lys
1               5                   10                  15

Phe

<210> SEQ ID NO 28
<211> LENGTH: 17
<212> TYPE: PRT
<213> ORGANISM: Artificial Sequence
<220> FEATURE:
<223> OTHER INFORMATION: Synthetic: Ad35

<400> SEQUENCE: 28

Gln Val Gly Asp Glu Thr Trp Thr Asp Leu Asp Gly Lys Thr Glu Glu
1               5                   10                  15

Tyr

<210> SEQ ID NO 29
<211> LENGTH: 14
<212> TYPE: PRT
<213> ORGANISM: Artificial Sequence
<220> FEATURE:
<223> OTHER INFORMATION: Synthetic: Ad51

<400> SEQUENCE: 29

Gln Val Gly Glu Glu Asn Trp Gln Glu Thr Phe Asn Phe Tyr
1               5                   10

<210> SEQ ID NO 30
<211> LENGTH: 14

```
<212> TYPE: PRT
<213> ORGANISM: Artificial Sequence
<220> FEATURE:
<223> OTHER INFORMATION: Synthetic: Ad9

<400> SEQUENCE: 30

Gln Val Gly Glu Glu Asn Leu Gln Asp Val Glu Asn Tyr Tyr
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic: Ad50

<400> SEQUENCE: 31

Gln Val Gly Glu Glu Ser Trp Thr Asp Thr Asp Gly Thr Gly Glu Lys
1               5                   10                  15

Tyr

<210> SEQ ID NO 32
<211> LENGTH: 16
<212> TYPE: PRT
<213> ORGANISM: Artificial Sequence
<220> FEATURE:
<223> OTHER INFORMATION: Synthetic: Ad5

<400> SEQUENCE: 32

Leu Gly Gly Val Ile Asn Thr Glu Thr Leu Thr Lys Val Lys Pro Lys
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic: Ad16

<400> SEQUENCE: 33

Leu Asn Gly Val Gly Phe Thr Asp Thr Tyr Gln Gly Val Lys Val Lys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic: Ad2

<400> SEQUENCE: 34

Leu Gly Gly Ile Gly Val Thr Asp Thr Tyr Gln Ala Ile Lys Ala Asn
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: Synthetic: Ad21

<400> SEQUENCE: 35

Leu Asp Gly Val Gly Val Pro Ile Ser Ser Tyr Lys Ile Ile Glu Pro
1               5                   10                  15

Asn
```

-continued

<210> SEQ ID NO 36
<211> LENGTH: 16
<212> TYPE: PRT
<213> ORGANISM: Artificial Sequence
<220> FEATURE:
<223> OTHER INFORMATION: Synthetic: Ad41

<400> SEQUENCE: 36

Leu Gly Gly Ser Ala Ala Thr Asp Thr Tyr Ser Gly Ile Lys Ala Asn
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic: Ad4

<400> SEQUENCE: 37

Leu Asn Gly Val Gly Leu Thr Asp Thr Tyr Gln Gly Val Lys Val Lys
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic: Ad3

<400> SEQUENCE: 38

Leu Asp Gly Ile Gly Pro Gly Asn Arg Tyr Gln Gly Ile Lys Val Lys
1               5                   10                  15

<210> SEQ ID NO 39
<211> LENGTH: 17
<212> TYPE: PRT
<213> ORGANISM: Artificial Sequence
<220> FEATURE:
<223> OTHER INFORMATION: Synthetic: Ad35

<400> SEQUENCE: 39

Leu Asp Gly Ile Gly Val Pro Thr Thr Ser Tyr Lys Ser Ile Val Pro
1               5                   10                  15
Asn

<210> SEQ ID NO 40
<211> LENGTH: 16
<212> TYPE: PRT
<213> ORGANISM: Artificial Sequence
<220> FEATURE:
<223> OTHER INFORMATION: Synthetic: Ad51

<400> SEQUENCE: 40

Leu Asp Gly Ser Gly Thr Asn Ala Ala Tyr Gln Gly Val Lys Val Thr
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic: Ad9

<400> SEQUENCE: 41

Leu Asp Gly Ala Gly Thr Asn Ala Thr Tyr Gln Gly Val Lys Val Lys
1               5                   10                  15

<210> SEQ ID NO 42
<211> LENGTH: 17
<212> TYPE: PRT
<213> ORGANISM: Artificial Sequence
<220> FEATURE:
<223> OTHER INFORMATION: Synthetic: Ad50

<400> SEQUENCE: 42

Leu Asp Gly Val Gly Pro Arg Ile Asp Ser Tyr Lys Gly Ile Glu Thr
1               5                   10                  15

Asn

<210> SEQ ID NO 43
<211> LENGTH: 16
<212> TYPE: PRT
<213> ORGANISM: Artificial Sequence
<220> FEATURE:
<223> OTHER INFORMATION: Synthetic: T423G;E424A

<400> SEQUENCE: 43

Leu Gly Gly Val Ile Asn Gly Ala Thr Leu Thr Lys Val Lys Pro Lys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic: E424A

<400> SEQUENCE: 44

Leu Gly Gly Val Ile Asn Thr Ala Thr Leu Thr Lys Val Lys Pro Lys
1               5                   10                  15

<210> SEQ ID NO 45
<211> LENGTH: 571
<212> TYPE: PRT
<213> ORGANISM: Artificial Sequence
<220> FEATURE:
<223> OTHER INFORMATION: Synthetic: Ad2 penton base

<400> SEQUENCE: 45

Met Gln Arg Ala Ala Met Tyr Glu Glu Gly Pro Pro Pro Ser Tyr Glu
1               5                   10                  15

Ser Val Val Ser Ala Ala Pro Val Ala Ala Leu Gly Ser Pro Phe
            20                  25                  30

Asp Ala Pro Leu Asp Pro Pro Phe Val Pro Pro Arg Tyr Leu Arg Pro
            35                  40                  45

Thr Gly Gly Arg Asn Ser Ile Arg Tyr Ser Glu Leu Ala Pro Leu Phe
    50                  55                  60

Asp Thr Thr Arg Val Tyr Leu Val Asp Asn Lys Ser Thr Asp Val Ala
65                  70                  75                  80

Ser Leu Asn Tyr Gln Asn Asp His Ser Asn Phe Leu Thr Thr Val Ile
                85                  90                  95

Gln Asn Asn Asp Tyr Ser Pro Gly Glu Ala Ser Thr Gln Thr Ile Asn
            100                 105                 110

Leu Asp Asp Arg Ser His Trp Gly Gly Asp Leu Lys Thr Ile Leu His
            115                 120                 125

Thr Asn Met Pro Asn Val Asn Glu Phe Met Phe Thr Asn Lys Phe Lys
    130                 135                 140

```
Ala Arg Val Met Val Ser Arg Ser Leu Thr Lys Asp Lys Gln Val Glu
145                 150                 155                 160

Leu Lys Tyr Glu Trp Val Glu Phe Thr Leu Pro Glu Gly Asn Tyr Ser
            165                 170                 175

Glu Thr Met Thr Ile Asp Leu Met Asn Asn Ala Ile Val Glu His Tyr
        180                 185                 190

Leu Lys Val Gly Arg Gln Asn Gly Val Leu Glu Ser Asp Ile Gly Val
    195                 200                 205

Lys Phe Asp Thr Arg Asn Phe Arg Leu Gly Phe Asp Pro Val Thr Gly
210                 215                 220

Leu Val Met Pro Gly Val Tyr Thr Asn Glu Ala Phe His Pro Asp Ile
225                 230                 235                 240

Ile Leu Leu Pro Gly Cys Gly Val Asp Phe Thr His Ser Arg Leu Ser
                245                 250                 255

Asn Leu Leu Gly Ile Arg Lys Arg Gln Pro Phe Gln Glu Gly Phe Arg
            260                 265                 270

Ile Thr Tyr Asp Asp Leu Glu Gly Gly Asn Ile Pro Ala Leu Leu Asp
        275                 280                 285

Val Asp Ala Tyr Gln Ala Ser Leu Lys Asp Asp Thr Glu Gln Gly Gly
    290                 295                 300

Gly Gly Ala Gly Gly Gly Asn Asn Ser Gly Ser Gly Ala Glu Glu Asn
305                 310                 315                 320

Ser Asn Ala Ala Ala Ala Met Gln Pro Val Glu Asp Met Asn Asp
                325                 330                 335

His Ala Ile Arg Gly Asp Thr Phe Ala Thr Arg Ala Glu Glu Lys Arg
            340                 345                 350

Ala Glu Ala Glu Ala Ala Glu Ala Ala Pro Ala Ala Gln Pro
                355                 360                 365

Glu Val Glu Lys Pro Gln Lys Lys Pro Val Ile Lys Pro Leu Thr Glu
        370                 375                 380

Asp Ser Lys Lys Arg Ser Tyr Asn Leu Ile Ser Asn Asp Ser Thr Phe
385                 390                 395                 400

Thr Gln Tyr Arg Ser Trp Tyr Leu Ala Tyr Asn Tyr Gly Asp Pro Gln
                405                 410                 415

Thr Gly Ile Arg Ser Trp Thr Leu Leu Cys Thr Pro Asp Val Thr Cys
            420                 425                 430

Gly Ser Glu Gln Val Tyr Trp Ser Leu Pro Asp Met Met Gln Asp Pro
        435                 440                 445

Val Thr Phe Arg Ser Thr Ser Gln Ile Ser Asn Phe Pro Val Val Gly
    450                 455                 460

Ala Glu Leu Leu Pro Val His Ser Lys Ser Phe Tyr Asn Asp Gln Ala
465                 470                 475                 480

Val Tyr Ser Gln Leu Ile Arg Gln Phe Thr Ser Leu Thr His Val Phe
                485                 490                 495

Asn Arg Phe Pro Glu Asn Gln Ile Leu Ala Arg Pro Ala Pro Thr
            500                 505                 510

Ile Thr Thr Val Ser Glu Asn Val Pro Ala Leu Thr Asp His Gly Thr
        515                 520                 525

Leu Pro Leu Arg Asn Ser Ile Gly Gly Val Gln Arg Val Thr Ile Thr
    530                 535                 540

Asp Ala Arg Arg Thr Cys Pro Tyr Val Tyr Lys Ala Leu Gly Ile
545                 550                 555                 560

Val Ser Pro Arg Val Leu Ser Ser Arg Thr Phe
```

<210> SEQ ID NO 46
<211> LENGTH: 544
<212> TYPE: PRT
<213> ORGANISM: Artificial Sequence
<220> FEATURE:
<223> OTHER INFORMATION: Synthetic: Ad3 penton base

<400> SEQUENCE: 46

```
Met Arg Arg Arg Ala Val Leu Gly Gly Ala Val Val Tyr Pro Glu Gly
1               5                   10                  15

Pro Pro Pro Ser Tyr Glu Ser Val Met Gln Gln Gln Ala Ala Met Leu
            20                  25                  30

Gln Pro Pro Leu Glu Ala Pro Phe Val Pro Pro Arg Tyr Leu Ala Pro
        35                  40                  45

Thr Glu Gly Arg Asn Ser Ile Arg Tyr Ser Glu Leu Ser Pro Leu Tyr
    50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
            100                 105                 110

Phe Asp Glu Arg Ser Arg Trp Gly Gly Gln Leu Lys Thr Ile Met His
        115                 120                 125

Thr Asn Met Pro Asn Val Asn Glu Tyr Met Phe Ser Asn Lys Phe Lys
    130                 135                 140

Ala Arg Val Met Val Ser Arg Lys Ala Pro Glu Gly Val Ile Val Asn
145                 150                 155                 160

Asp Thr Tyr Asp His Lys Glu Asp Ile Leu Lys Tyr Glu Trp Phe Glu
                165                 170                 175

Phe Thr Leu Pro Glu Gly Asn Phe Ser Ala Thr Met Thr Ile Asp Leu
            180                 185                 190

Met Asn Asn Ala Ile Ile Asp Asn Tyr Leu Glu Ile Gly Arg Gln Asn
        195                 200                 205

Gly Val Leu Glu Ser Asp Ile Gly Val Lys Phe Asp Thr Arg Asn Phe
    210                 215                 220

Arg Leu Gly Trp Asp Pro Glu Thr Lys Leu Ile Met Pro Gly Val Tyr
225                 230                 235                 240

Thr Tyr Glu Ala Phe His Pro Asp Ile Val Leu Leu Pro Gly Cys Gly
                245                 250                 255

Val Asp Phe Thr Glu Ser Arg Leu Ser Asn Leu Leu Gly Ile Arg Lys
            260                 265                 270

Arg His Pro Phe Gln Glu Gly Phe Lys Ile Met Tyr Glu Asp Leu Glu
        275                 280                 285

Gly Gly Asn Ile Pro Ala Leu Leu Asp Val Thr Ala Tyr Glu Glu Ser
    290                 295                 300

Lys Lys Asp Thr Thr Thr Glu Thr Thr Thr Leu Ala Val Ala Glu Glu
305                 310                 315                 320

Thr Ser Glu Asp Asp Asn Ile Thr Arg Gly Asp Thr Tyr Ile Thr Glu
                325                 330                 335

Lys Gln Lys Arg Glu Ala Ala Ala Glu Val Lys Lys Glu Leu Lys
            340                 345                 350

Ile Gln Pro Leu Glu Lys Asp Ser Lys Ser Arg Ser Tyr Asn Val Leu
```

```
            355                 360                 365
Glu Asp Lys Ile Asn Thr Ala Tyr Arg Ser Trp Tyr Leu Ser Tyr Asn
370                 375                 380

Tyr Gly Asn Pro Glu Lys Gly Ile Arg Ser Trp Thr Leu Leu Thr Thr
385                 390                 395                 400

Ser Asp Val Thr Cys Gly Ala Glu Gln Val Tyr Trp Ser Leu Pro Asp
                405                 410                 415

Met Met Gln Asp Pro Val Thr Phe Arg Ser Thr Arg Gln Val Asn Asn
                420                 425                 430

Tyr Pro Val Val Gly Ala Glu Leu Met Pro Val Phe Ser Lys Ser Phe
                435                 440                 445

Tyr Asn Glu Gln Ala Val Tyr Ser Gln Gln Leu Arg Gln Ala Thr Ser
                450                 455                 460

Leu Thr His Val Phe Asn Arg Phe Pro Glu Asn Gln Ile Leu Ile Arg
465                 470                 475                 480

Pro Pro Ala Pro Thr Ile Thr Thr Val Ser Glu Asn Val Pro Ala Leu
                485                 490                 495

Thr Asp His Gly Thr Leu Pro Leu Arg Ser Ser Ile Arg Gly Val Gln
                500                 505                 510

Arg Val Thr Val Thr Asp Ala Arg Arg Thr Cys Pro Tyr Val Tyr
                515                 520                 525

Lys Ala Leu Gly Ile Val Ala Pro Arg Val Leu Ser Ser Arg Thr Phe
530                 535                 540

<210> SEQ ID NO 47
<211> LENGTH: 544
<212> TYPE: PRT
<213> ORGANISM: Artificial Sequence
<220> FEATURE:
<223> OTHER INFORMATION: Synthetic: Ad7 penton base

<400> SEQUENCE: 47

Met Arg Arg Arg Ala Val Leu Gly Gly Ala Met Val Tyr Pro Glu Gly
1               5                   10                  15

Pro Pro Pro Ser Tyr Glu Ser Val Met Gln Gln Gln Ala Ala Met Ile
                20                  25                  30

Gln Pro Pro Leu Glu Ala Pro Phe Val Pro Pro Arg Tyr Leu Ala Pro
                35                  40                  45

Thr Glu Gly Arg Asn Ser Ile Arg Tyr Ser Glu Leu Ser Pro Leu Tyr
            50                  55                  60

Asp Thr Thr Lys Leu Tyr Leu Val Asp Asn Lys Ser Ala Asp Ile Ala
65                  70                  75                  80

Ser Leu Asn Tyr Gln Asn Asp His Ser Asn Phe Leu Thr Thr Val Val
                85                  90                  95

Gln Asn Asn Asp Phe Thr Pro Thr Glu Ala Ser Thr Gln Thr Ile Asn
                100                 105                 110

Phe Asp Glu Arg Ser Arg Trp Gly Gly Gln Leu Lys Thr Ile Met His
                115                 120                 125

Thr Asn Met Pro Asn Val Asn Glu Tyr Met Phe Ser Asn Lys Phe Lys
                130                 135                 140

Ala Arg Val Met Val Ser Arg Lys Ala Pro Glu Gly Val Ile Val Asn
145                 150                 155                 160

Asp Thr Tyr Asp His Lys Glu Asp Ile Leu Lys Tyr Glu Trp Phe Glu
                165                 170                 175

Phe Thr Leu Pro Glu Gly Asn Phe Ser Ala Thr Met Thr Ile Asp Leu
```

-continued

```
                180                 185                 190
Met Asn Asn Ala Ile Ile Asp Asn Tyr Leu Glu Ile Gly Arg Gln Asn
                195                 200                 205
Gly Val Leu Glu Ser Asp Ile Gly Val Lys Phe Asp Thr Arg Asn Phe
            210                 215                 220
Arg Leu Gly Trp Asp Pro Glu Thr Lys Leu Ile Met Pro Gly Val Tyr
225                 230                 235                 240
Thr Tyr Glu Ala Phe His Pro Asp Ile Val Leu Leu Pro Gly Cys Gly
                245                 250                 255
Val Asp Phe Thr Glu Ser Arg Leu Ser Asn Leu Leu Gly Ile Arg Lys
            260                 265                 270
Arg His Pro Phe Gln Glu Gly Phe Lys Ile Met Tyr Glu Asp Leu Glu
        275                 280                 285
Gly Gly Asn Ile Pro Ala Leu Leu Asp Val Thr Ala Tyr Glu Glu Ser
        290                 295                 300
Lys Lys Asp Thr Thr Thr Glu Thr Thr Thr Leu Ala Val Ala Glu Glu
305                 310                 315                 320
Thr Ser Glu Asp Asp Asn Ile Thr Arg Gly Asp Thr Tyr Ile Thr Glu
                325                 330                 335
Lys Gln Lys Arg Glu Ala Ala Ala Glu Val Lys Lys Glu Leu Lys
            340                 345                 350
Ile Gln Pro Leu Glu Lys Asp Ser Lys Ser Arg Ser Tyr Asn Val Leu
        355                 360                 365
Glu Asp Lys Ile Asn Thr Ala Tyr Arg Ser Trp Tyr Leu Ser Tyr Asn
    370                 375                 380
Tyr Gly Asn Pro Glu Lys Gly Ile Arg Ser Trp Thr Leu Leu Thr Thr
385                 390                 395                 400
Ser Asp Val Thr Cys Gly Ala Glu Gln Val Tyr Trp Ser Leu Pro Asp
                405                 410                 415
Met Met Gln Asp Pro Val Thr Phe Arg Ser Thr Arg Gln Val Asn Asn
            420                 425                 430
Tyr Pro Val Val Gly Ala Glu Leu Met Pro Val Phe Ser Lys Ser Phe
        435                 440                 445
Tyr Asn Glu Gln Ala Val Tyr Ser Gln Gln Leu Arg Gln Ala Thr Ser
    450                 455                 460
Leu Thr His Val Phe Asn Arg Phe Pro Glu Asn Gln Ile Leu Ile Arg
465                 470                 475                 480
Pro Pro Ala Pro Thr Ile Thr Thr Val Ser Glu Asn Val Pro Ala Leu
                485                 490                 495
Thr Asp His Gly Thr Leu Pro Leu Arg Ser Ser Ile Arg Gly Val Gln
            500                 505                 510
Arg Val Thr Val Thr Asp Ala Arg Arg Thr Cys Pro Tyr Val Tyr
        515                 520                 525
Lys Ala Leu Gly Ile Val Ala Pro Arg Val Leu Ser Ser Arg Thr Phe
    530                 535                 540
```

<210> SEQ ID NO 48
<211> LENGTH: 561
<212> TYPE: PRT
<213> ORGANISM: Artificial Sequence
<220> FEATURE:
<223> OTHER INFORMATION: Synthetic: Ad11 penton base

<400> SEQUENCE: 48

Met Arg Arg Val Val Leu Gly Gly Ala Val Val Tyr Pro Glu Gly Pro

-continued

```
1               5                   10                  15
Pro Pro Ser Tyr Glu Ser Val Met Gln Gln Gln Ala Thr Ala Val
                20                  25                  30
Met Gln Ser Pro Leu Glu Ala Pro Phe Val Pro Pro Arg Tyr Leu Ala
                35                  40                  45
Pro Thr Glu Gly Arg Asn Ser Ile Arg Tyr Ser Glu Leu Ala Pro Gln
 50                 55                  60
Tyr Asp Thr Thr Arg Leu Tyr Leu Val Asp Asn Lys Ser Ala Asp Ile
 65                 70                  75                  80
Ala Ser Leu Asn Tyr Gln Asn Asp His Ser Asn Phe Leu Thr Thr Val
                85                  90                  95
Val Gln Asn Asn Asp Phe Thr Pro Thr Glu Ala Ser Thr Gln Thr Ile
                100                 105                 110
Asn Phe Asp Glu Arg Ser Arg Trp Gly Gly Gln Leu Lys Thr Ile Met
                115                 120                 125
His Thr Asn Met Pro Asn Val Asn Glu Tyr Met Phe Ser Asn Lys Phe
 130                135                 140
Lys Ala Arg Val Met Val Ser Arg Lys Pro Pro Asp Gly Ala Ala Val
145                 150                 155                 160
Gly Asp Thr Tyr Asp His Lys Gln Asp Ile Leu Lys Tyr Glu Trp Phe
                165                 170                 175
Glu Phe Thr Leu Pro Glu Gly Asn Phe Ser Val Thr Met Thr Ile Asp
                180                 185                 190
Leu Met Asn Asn Ala Ile Ile Asp Asn Tyr Leu Lys Val Gly Arg Gln
                195                 200                 205
Asn Gly Val Leu Glu Ser Asp Ile Gly Val Lys Phe Asp Thr Arg Asn
 210                215                 220
Phe Lys Leu Gly Trp Asp Pro Glu Thr Lys Leu Ile Met Pro Gly Val
225                 230                 235                 240
Tyr Thr Tyr Glu Ala Phe His Pro Asp Ile Val Leu Leu Pro Gly Cys
                245                 250                 255
Gly Val Asp Phe Thr Glu Ser Arg Leu Ser Asn Leu Leu Gly Ile Arg
                260                 265                 270
Lys Lys Gln Pro Phe Gln Glu Gly Phe Lys Ile Leu Tyr Glu Asp Leu
                275                 280                 285
Glu Gly Gly Asn Ile Pro Ala Leu Leu Asp Val Asp Ala Tyr Glu Asn
                290                 295                 300
Ser Lys Lys Glu Gln Lys Ala Lys Ile Glu Ala Ala Thr Ala Ala Ala
305                 310                 315                 320
Glu Ala Lys Ala Asn Ile Val Ala Ser Asp Ser Thr Arg Val Ala Asn
                325                 330                 335
Ala Gly Glu Val Arg Gly Asp Asn Phe Ala Pro Thr Pro Val Pro Thr
                340                 345                 350
Ala Glu Ser Leu Leu Ala Asp Val Ser Glu Gly Thr Asp Val Lys Leu
                355                 360                 365
Thr Ile Gln Pro Val Glu Lys Asp Ser Lys Asn Arg Ser Tyr Asn Val
 370                375                 380
Leu Glu Asp Lys Ile Asn Thr Ala Tyr Arg Ser Trp Tyr Leu Ser Tyr
385                 390                 395                 400
Asn Tyr Gly Asp Pro Glu Lys Gly Val Arg Ser Trp Thr Leu Leu Thr
                405                 410                 415
Thr Ser Asp Val Thr Cys Gly Ala Glu Gln Val Tyr Trp Ser Leu Pro
                420                 425                 430
```

```
Asp Met Met Lys Asp Pro Val Thr Phe Arg Ser Thr Arg Gln Val Ser
        435                 440                 445

Asn Tyr Pro Val Val Gly Ala Glu Leu Met Pro Val Phe Ser Lys Ser
    450                 455                 460

Phe Tyr Asn Glu Gln Ala Val Tyr Ser Gln Gln Leu Arg Gln Ser Thr
465                 470                 475                 480

Ser Leu Thr His Val Phe Asn Arg Phe Pro Glu Asn Gln Ile Leu Ile
                485                 490                 495

Arg Pro Pro Ala Pro Thr Ile Thr Thr Val Ser Glu Asn Val Pro Ala
            500                 505                 510

Leu Thr Asp His Gly Thr Leu Pro Leu Arg Ser Ser Ile Arg Gly Val
        515                 520                 525

Gln Arg Val Thr Val Thr Asp Ala Arg Arg Thr Cys Pro Tyr Val
        530                 535                 540

Tyr Lys Ala Leu Gly Ile Val Ala Pro Arg Val Leu Ser Ser Arg Thr
545                 550                 555                 560

Phe
```

<210> SEQ ID NO 49
<211> LENGTH: 508
<212> TYPE: PRT
<213> ORGANISM: Artificial Sequence
<220> FEATURE:
<223> OTHER INFORMATION: Synthetic: Ad41 penton base

<400> SEQUENCE: 49

```
Met Arg Arg Ala Val Gly Val Pro Pro Val Met Ala Tyr Ala Glu Gly
1               5                   10                  15

Pro Pro Pro Ser Tyr Glu Ser Val Met Gly Ser Ala Asp Ser Pro Ala
            20                  25                  30

Thr Leu Glu Ala Leu Tyr Val Pro Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Gln Thr Thr Val Val Gln Asn
                85                  90                  95

Asn Asp Phe Thr Pro Ala Glu Ala Gly Thr Gln Thr Ile Asn Phe Asp
            100                 105                 110

Glu Arg Ser Arg Trp Gly Ala Asp Leu Lys Thr Ile Leu Arg Thr Asn
        115                 120                 125

Met Pro Asn Ile Asn Glu Phe Met Ser Thr Asn Lys Phe Lys Ala Arg
    130                 135                 140

Leu Met Val Glu Lys Lys Asn Lys Glu Thr Gly Leu Pro Arg Tyr Glu
145                 150                 155                 160

Trp Phe Glu Phe Thr Leu Pro Glu Gly Asn Tyr Ser Glu Thr Met Thr
                165                 170                 175

Ile Asp Leu Met Asn Asn Ala Ile Val Asp Asn Tyr Leu Glu Val Gly
            180                 185                 190

Arg Gln Asn Gly Val Leu Glu Ser Asp Ile Gly Val Lys Phe Asp Thr
        195                 200                 205

Arg Asn Phe Arg Leu Gly Trp Asp Pro Val Thr Lys Leu Val Met Pro
    210                 215                 220
```

```
Gly Val Tyr Thr Asn Glu Ala Phe His Pro Asp Ile Val Leu Leu Pro
225                 230                 235                 240

Gly Cys Gly Val Asp Phe Thr Gln Ser Arg Leu Ser Asn Leu Leu Gly
            245                 250                 255

Ile Arg Lys Arg Leu Pro Phe Gln Glu Gly Phe Gln Ile Met Tyr Glu
            260                 265                 270

Asp Leu Glu Gly Gly Asn Ile Pro Ala Leu Leu Asp Val Ala Lys Tyr
            275                 280                 285

Glu Ala Ser Ile Gln Lys Ala Lys Glu Glu Gly Lys Glu Ile Gly Asp
            290                 295                 300

Asp Thr Phe Ala Thr Arg Pro Gln Asp Leu Val Ile Glu Pro Val Ala
305                 310                 315                 320

Lys Asp Ser Lys Asn Arg Ser Tyr Asn Leu Leu Pro Asn Asp Gln Asn
            325                 330                 335

Asn Thr Ala Tyr Arg Ser Trp Phe Leu Ala Tyr Asn Tyr Gly Asp Pro
            340                 345                 350

Lys Lys Gly Val Gln Ser Trp Thr Leu Leu Thr Thr Ala Asp Val Thr
            355                 360                 365

Cys Gly Ser Gln Gln Val Tyr Trp Ser Leu Pro Asp Met Met Gln Asp
            370                 375                 380

Pro Val Thr Phe Arg Pro Ser Thr Gln Val Ser Asn Tyr Pro Val Val
385                 390                 395                 400

Gly Val Glu Leu Leu Pro Val His Ala Lys Ser Phe Tyr Asn Glu Gln
            405                 410                 415

Ala Val Tyr Ser Gln Leu Ile Arg Gln Ser Thr Ala Leu Thr His Val
            420                 425                 430

Phe Asn Arg Phe Pro Glu Asn Gln Ile Leu Val Arg Pro Pro Ala Pro
            435                 440                 445

Thr Ile Thr Thr Val Ser Glu Asn Val Pro Ala Leu Thr Asp His Gly
            450                 455                 460

Thr Leu Pro Leu Arg Ser Ser Ile Ser Gly Val Gln Arg Val Thr Ile
465                 470                 475                 480

Thr Asp Ala Arg Arg Thr Cys Pro Tyr Val His Lys Ala Leu Gly
            485                 490                 495

Ile Val Ala Pro Lys Val Leu Ser Ser Arg Thr Phe
            500                 505

<210> SEQ ID NO 50
<211> LENGTH: 497
<212> TYPE: PRT
<213> ORGANISM: Artificial Sequence
<220> FEATURE:
<223> OTHER INFORMATION: Synthetic: Ad12 penton base

<400> SEQUENCE: 50

Met Arg Arg Ala Val Glu Leu Gln Thr Val Ala Phe Pro Glu Thr Pro
1               5                   10                  15

Pro Pro Ser Tyr Glu Thr Val Met Ala Ala Pro Tyr Val Pro
            20                  25                  30

Pro Arg Tyr Leu Gly Pro Thr Glu Gly Arg Asn Ser Ile Arg Tyr Ser
            35                  40                  45

Glu Leu Ser Pro Leu Tyr Asp Thr Thr Arg Val Tyr Leu Val Asp Asn
            50                  55                  60

Lys Ser Ser Asp Ile Ala Ser Leu Asn Tyr Gln Asn Asp His Ser Asn
65                  70                  75                  80
```

Phe Leu Thr Thr Val Gln Asn Asn Asp Tyr Ser Pro Ile Glu Ala
            85                  90                  95

Gly Thr Gln Thr Ile Asn Phe Asp Glu Arg Ser Arg Trp Gly Gly Asp
        100                 105                 110

Leu Lys Thr Ile Leu His Thr Asn Met Pro Asn Val Asn Asp Phe Met
        115                 120                 125

Phe Thr Thr Lys Phe Lys Ala Arg Val Met Val Ala Arg Lys Thr Asn
        130                 135                 140

Asn Glu Gly Gln Thr Ile Leu Glu Tyr Glu Trp Ala Glu Phe Val Leu
145                 150                 155                 160

Pro Glu Gly Asn Tyr Ser Glu Thr Met Thr Ile Asp Leu Met Asn Asn
                165                 170                 175

Ala Ile Ile Glu His Tyr Leu Arg Val Gly Arg Gln His Gly Val Leu
                180                 185                 190

Glu Ser Asp Ile Gly Val Lys Phe Asp Thr Arg Asn Phe Arg Leu Gly
            195                 200                 205

Trp Asp Pro Glu Thr Gln Leu Val Thr Pro Gly Val Tyr Thr Asn Glu
210                 215                 220

Ala Phe His Pro Asp Ile Val Leu Leu Pro Gly Cys Gly Val Asp Phe
225                 230                 235                 240

Thr Glu Ser Arg Leu Ser Asn Ile Leu Gly Ile Arg Lys Arg Gln Pro
                245                 250                 255

Phe Gln Glu Gly Phe Val Ile Met Tyr Glu His Leu Glu Gly Gly Asn
            260                 265                 270

Ile Pro Ala Leu Leu Asp Val Lys Lys Tyr Glu Asn Ser Leu Gln Asp
            275                 280                 285

Gln Asn Thr Val Arg Gly Asp Asn Phe Ile Ala Leu Asn Lys Ala Ala
        290                 295                 300

Arg Ile Glu Pro Val Glu Thr Asp Pro Lys Gly Arg Ser Tyr Asn Leu
305                 310                 315                 320

Leu Pro Asp Lys Lys Asn Thr Lys Tyr Arg Ser Trp Tyr Leu Ala Tyr
                325                 330                 335

Asn Tyr Gly Asp Pro Glu Lys Gly Val Arg Ser Trp Thr Leu Leu Thr
            340                 345                 350

Thr Pro Asp Val Thr Gly Gly Ser Glu Gln Val Tyr Trp Ser Leu Pro
        355                 360                 365

Asp Met Met Gln Asp Pro Val Thr Phe Arg Ser Ser Arg Gln Val Ser
        370                 375                 380

Asn Tyr Pro Val Val Ala Ala Glu Leu Leu Pro Val His Ala Lys Ser
385                 390                 395                 400

Phe Tyr Asn Glu Gln Ala Val Tyr Ser Gln Leu Ile Arg Gln Ser Thr
                405                 410                 415

Ala Leu Thr Arg Val Phe Asn Arg Phe Pro Glu Asn Gln Ile Leu Val
            420                 425                 430

Arg Pro Pro Ala Ala Thr Ile Thr Thr Val Ser Glu Asn Val Pro Ala
        435                 440                 445

Leu Thr Asp His Gly Thr Leu Pro Leu Arg Ser Ser Ile Ser Gly Val
        450                 455                 460

Gln Arg Val Thr Ile Thr Asp Ala Arg Arg Arg Thr Cys Pro Tyr Val
465                 470                 475                 480

Tyr Lys Ala Leu Gly Ile Val Ser Pro Arg Val Leu Ser Ser Arg Thr
                485                 490                 495

Phe

<210> SEQ ID NO 51
<211> LENGTH: 517
<212> TYPE: PRT
<213> ORGANISM: Artificial Sequence
<220> FEATURE:
<223> OTHER INFORMATION: Synthetic: Ad17 penton base

<400> SEQUENCE: 51

```
Met Arg Arg Ala Val Ser Ser Pro Pro Ser Tyr Glu Ser
1               5                   10                  15

Val Met Ala Gln Ala Thr Leu Glu Val Pro Phe Val Pro Pro Arg Tyr
                20                  25                  30

Met Ala Pro Thr Glu Gly Arg Asn Ser Ile Arg Tyr Ser Glu Leu Ala
            35                  40                  45

Pro Leu Tyr Asp Thr Thr Arg Val Tyr Leu Val Asp Asn Lys Ser Ala
50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
            115                 120                 125

Lys Phe Lys Ala Arg Val Met Val Ala Arg Lys His Pro Gln Gly Val
    130                 135                 140

Glu Ala Thr Asp Leu Ser Lys Asp Ile Leu Glu Tyr Glu Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Lys Leu Gly Trp Asp Pro Val Thr Lys Leu Val Met Pro Gly Val Tyr
    210                 215                 220

Thr Tyr Glu Ala Phe His Pro Asp Val Val Leu Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Glu
            260                 265                 270

Gly Gly Asn Ile Pro Ala Leu Leu Asp Val Pro Lys Tyr Leu Glu Ser
        275                 280                 285

Lys Lys Lys Leu Glu Glu Ala Leu Glu Asn Ala Ala Lys Ala Asn Gly
    290                 295                 300

Pro Ala Arg Gly Asp Ser Ser Val Ser Arg Glu Val Glu Lys Ala Ala
305                 310                 315                 320

Glu Lys Glu Leu Val Ile Glu Pro Ile Lys Gln Asp Asp Ser Lys Arg
                325                 330                 335

Ser Tyr Asn Leu Ile Glu Gly Thr Met Asp Thr Leu Tyr Arg Ser Trp
            340                 345                 350

Tyr Leu Ser Tyr Thr Tyr Gly Asp Pro Glu Lys Gly Val Gln Ser Trp
        355                 360                 365
```

```
Thr Leu Leu Thr Thr Pro Asp Val Thr Cys Gly Ala Glu Gln Val Tyr
        370                 375                 380

Trp Ser Leu Pro Asp Leu Met Gln Asp Pro Val Thr Phe Arg Ser Thr
385                 390                 395                 400

Gln Gln Val Ser Asn Tyr Pro Val Val Gly Ala Glu Leu Met Pro Phe
                405                 410                 415

Arg Ala Lys Ser Phe Tyr Asn Asp Leu Ala Val Tyr Ser Gln Leu Ile
            420                 425                 430

Arg Ser Tyr Thr Ser Leu Thr His Val Phe Asn Arg Phe Pro Asp Asn
        435                 440                 445

Gln Ile Leu Cys Arg Pro Pro Ala Pro Thr Ile Thr Val Ser Glu
    450                 455                 460

Asn Val Pro Ala Leu Thr Asp His Gly Thr Leu Pro Leu Arg Ser Ser
465                 470                 475                 480

Ile Arg Gly Val Gln Arg Val Thr Val Thr Asp Ala Arg Arg Thr
                485                 490                 495

Cys Pro Tyr Val Tyr Lys Ala Leu Gly Ile Val Ala Pro Arg Val Leu
                500                 505                 510

Ser Ser Arg Thr Phe
            515

<210> SEQ ID NO 52
<211> LENGTH: 520
<212> TYPE: PRT
<213> ORGANISM: Artificial Sequence
<220> FEATURE:
<223> OTHER INFORMATION: Synthetic: Ad25 penton base

<400> SEQUENCE: 52

Met Arg Arg Ala Val Val Ser Ser Ser Pro Pro Pro Ser Tyr Glu Ser
1               5                   10                  15

Val Met Ala Gln Ala Thr Leu Glu Val Pro Phe Val Pro Pro Arg Tyr
            20                  25                  30

Met Ala Pro Thr Glu Gly Arg Asn Ser Ile Arg Tyr Ser Glu Leu Ala
        35                  40                  45

Pro Gln Tyr Asp Thr Thr Arg Val Tyr Leu Val Asp Asn Lys Ser Ala
    50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
        115                 120                 125

Lys Phe Lys Ala Arg Val Met Val Ala Arg Lys His Pro Glu Asn Val
    130                 135                 140

Asp Lys Thr Asp Leu Ser Gln Asp Lys Leu Glu Tyr Glu Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205
```

```
Lys Leu Gly Trp Asp Pro Val Thr Lys Leu Val Met Pro Gly Val Tyr
    210                 215                 220

Thr Tyr Glu Ala Phe His Pro Asp Val Val Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Glu
                260                 265                 270

Gly Gly Asn Ile Pro Ala Leu Leu Asp Thr Lys Lys Tyr Leu Asp Ser
                275                 280                 285

Lys Lys Glu Leu Glu Asp Ala Ala Lys Glu Ala Lys Gln Gln Gly
    290                 295                 300

Asp Gly Ala Val Thr Arg Gly Asp Thr His Leu Thr Val Ala Gln Glu
305                 310                 315                 320

Lys Ala Ala Glu Lys Glu Leu Val Ile Val Pro Ile Glu Lys Asp Glu
                325                 330                 335

Ser Asn Arg Ser Tyr Asn Leu Ile Lys Asp Thr His Asp Thr Met Tyr
                340                 345                 350

Arg Ser Trp Tyr Leu Ser Tyr Thr Tyr Gly Asp Pro Glu Lys Gly Val
    355                 360                 365

Gln Ser Trp Thr Leu Leu Thr Thr Pro Asp Val Thr Cys Gly Ala Glu
    370                 375                 380

Gln Val Tyr Trp Ser Leu Pro Asp Leu Met Gln Asp Pro Val Thr Phe
385                 390                 395                 400

Arg Ser Thr Gln Gln Val Ser Asn Tyr Pro Val Val Gly Ala Glu Leu
                405                 410                 415

Met Pro Phe Arg Ala Lys Ser Phe Tyr Asn Asp Leu Ala Val Tyr Ser
                420                 425                 430

Gln Leu Ile Arg Ser Tyr Thr Ser Leu Thr His Val Phe Asn Arg Phe
    435                 440                 445

Pro Asp Asn Gln Ile Leu Cys Arg Pro Pro Ala Pro Thr Ile Thr Thr
    450                 455                 460

Val Ser Glu Asn Val Pro Ala Leu Thr Asp His Gly Thr Leu Pro Leu
465                 470                 475                 480

Arg Ser Ser Ile Arg Gly Val Gln Arg Val Thr Val Thr Asp Ala Arg
                485                 490                 495

Arg Arg Thr Cys Pro Tyr Val Tyr Lys Ala Leu Gly Ile Val Ala Pro
                500                 505                 510

Arg Val Leu Ser Ser Arg Thr Phe
        515                 520

<210> SEQ ID NO 53
<211> LENGTH: 519
<212> TYPE: PRT
<213> ORGANISM: Artificial Sequence
<220> FEATURE:
<223> OTHER INFORMATION: Synthetic: Ad37 penton base

<400> SEQUENCE: 53

Met Arg Arg Ala Val Val Ser Ser Pro Pro Pro Tyr Glu Ser
1               5                   10                  15

Val Met Ala Gln Ala Thr Leu Glu Val Pro Phe Val Pro Pro Arg Tyr
                20                  25                  30

Met Ala Pro Thr Glu Gly Arg Asn Ser Ile Arg Tyr Ser Glu Leu Ala
            35                  40                  45
```

```
Pro Leu Tyr Asp Thr Thr Arg Val Tyr Leu Val Asp Asn Lys Ser Ala
    50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
                100                 105                 110

Ile Leu His Thr Asn Met Pro Asn Val Asn Glu Tyr Met Phe Thr Ser
            115                 120                 125

Lys Phe Lys Ala Arg Val Met Val Ala Arg Lys Lys Ala Glu Gly Ala
        130                 135                 140

Asp Ala Asn Asp Arg Ser Lys Asp Ile Leu Glu Tyr Gln Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Lys Leu Gly Trp Asp Pro Val Thr Lys Leu Val Met Pro Gly Val Tyr
    210                 215                 220

Thr Tyr Glu Ala Phe His Pro Asp Val Val Leu Leu Pro Gly Cys Gly
225                 230                 235                 240

Val Asp Phe Thr Glu Ser Arg Leu Ser Asn Leu Leu Gly Ile Arg Lys
                245                 250                 255

Lys Gln Pro Phe Gln Glu Gly Phe Arg Ile Met Tyr Glu Asp Leu Val
            260                 265                 270

Gly Gly Asn Ile Pro Ala Leu Leu Asn Val Lys Glu Tyr Leu Lys Asp
        275                 280                 285

Lys Glu Glu Ala Gly Lys Ala Asp Ala Asn Thr Ile Lys Ala Gln Asn
    290                 295                 300

Asp Ala Val Pro Arg Gly Asp Asn Tyr Ala Ser Ala Glu Ala Lys
305                 310                 315                 320

Ala Ala Gly Lys Glu Ile Glu Leu Lys Ala Ile Leu Lys Asp Asp Ser
                325                 330                 335

Asp Arg Ser Tyr Asn Val Ile Glu Gly Thr Thr Asp Thr Leu Tyr Arg
            340                 345                 350

Ser Trp Tyr Leu Ser Tyr Thr Tyr Gly Asp Pro Glu Lys Gly Val Gln
        355                 360                 365

Ser Trp Thr Leu Leu Thr Thr Pro Asp Val Thr Cys Gly Ala Glu Gln
    370                 375                 380

Val Tyr Trp Ser Leu Pro Asp Leu Met Gln Asp Pro Val Thr Phe Arg
385                 390                 395                 400

Ser Thr Gln Gln Val Ser Asn Tyr Pro Val Val Gly Ala Glu Leu Met
                405                 410                 415

Pro Phe Arg Ala Lys Ser Phe Tyr Asn Asp Leu Ala Val Tyr Ser Gln
            420                 425                 430

Leu Ile Arg Ser Tyr Thr Ser Leu Thr His Val Phe Asn Arg Phe Pro
        435                 440                 445

Asp Asn Gln Ile Leu Cys Arg Pro Pro Ala Pro Thr Ile Thr Thr Val
    450                 455                 460
```

```
Ser Glu Asn Val Pro Ala Leu Thr Asp His Gly Thr Leu Pro Leu Arg
465                 470                 475                 480

Ser Ser Ile Arg Gly Val Gln Arg Val Thr Val Thr Asp Ala Arg Arg
                485                 490                 495

Arg Thr Cys Pro Tyr Val Tyr Lys Ala Leu Gly Ile Val Ala Pro Arg
            500                 505                 510

Val Leu Ser Ser Arg Thr Phe
            515
```

<210> SEQ ID NO 54
<211> LENGTH: 101
<212> TYPE: PRT
<213> ORGANISM: Artificial Sequence
<220> FEATURE:
<223> OTHER INFORMATION: Synthetic: Wild type Ad5 penton base

<400> SEQUENCE: 54

```
Asp Ala Tyr Gln Ala Ser Leu Lys Asp Asp Thr Glu Gln Gly Gly Gly
1               5                   10                  15

Gly Ala Gly Gly Ser Asn Ser Ser Gly Ser Gly Ala Glu Glu Asn Ser
                20                  25                  30

Asn Ala Ala Ala Ala Ala Met Gln Pro Val Glu Asp Met Asn Asp His
            35                  40                  45

Ala Ile Arg Gly Asp Thr Phe Ala Thr Arg Ala Glu Glu Lys Arg Ala
        50                  55                  60

Glu Ala Glu Ala Ala Ala Glu Ala Ala Ala Pro Ala Ala Gln Pro Glu
65                  70                  75                  80

Val Glu Lys Pro Gln Lys Lys Pro Val Ile Lys Pro Leu Thr Glu Asp
                85                  90                  95

Ser Lys Lys Arg Ser
            100
```

<210> SEQ ID NO 55
<211> LENGTH: 98
<212> TYPE: PRT
<213> ORGANISM: Artificial Sequence
<220> FEATURE:
<223> OTHER INFORMATION: Synthetic: RGD-motif-deleted penton base

<400> SEQUENCE: 55

```
Asp Ala Tyr Gln Ala Ser Leu Lys Asp Asp Thr Glu Gln Gly Gly Gly
1               5                   10                  15

Gly Ala Gly Gly Ser Asn Ser Ser Gly Ser Gly Ala Glu Glu Asn Ser
                20                  25                  30

Asn Ala Ala Ala Ala Ala Met Gln Pro Val Glu Asp Met Asn Asp His
            35                  40                  45

Ala Ile Thr Phe Ala Thr Arg Ala Glu Glu Lys Arg Ala Glu Ala Glu
        50                  55                  60

Ala Ala Ala Glu Ala Ala Ala Pro Ala Ala Gln Pro Glu Val Glu Lys
65                  70                  75                  80

Pro Gln Lys Lys Pro Val Ile Lys Pro Leu Thr Glu Asp Ser Lys Lys
                85                  90                  95

Arg Ser
```

<210> SEQ ID NO 56
<211> LENGTH: 57
<212> TYPE: PRT
<213> ORGANISM: Artificial Sequence
<220> FEATURE:

<223> OTHER INFORMATION: Synthetic: Ad5-GFP

<400> SEQUENCE: 56

Asn Ala Ala Ala Ala Met Gln Pro Val Glu Asp Met Asn Asp His
1               5                   10                  15

Ala Ile Arg Gly Asp Thr Phe Ala Thr Arg Ala Glu Glu Lys Arg Ala
            20                  25                  30

Glu Ala Glu Ala Ala Ala Glu Ala Ala Ala Pro Ala Ala Gln Pro Glu
        35                  40                  45

Val Glu Lys Pro Gln Lys Lys Pro Val
    50                  55

<210> SEQ ID NO 57
<211> LENGTH: 54
<212> TYPE: PRT
<213> ORGANISM: Artificial Sequence
<220> FEATURE:
<223> OTHER INFORMATION: Synthetic: dRGD

<400> SEQUENCE: 57

Asn Ala Ala Ala Ala Met Gln Pro Val Glu Asp Met Asn Asp His
1               5                   10                  15

Ala Ile Thr Phe Ala Thr Arg Ala Glu Glu Lys Arg Ala Glu Ala Glu
            20                  25                  30

Ala Ala Ala Glu Ala Ala Ala Pro Ala Ala Gln Pro Glu Val Glu Lys
        35                  40                  45

Pro Gln Lys Lys Pro Val
    50

<210> SEQ ID NO 58
<211> LENGTH: 12
<212> TYPE: PRT
<213> ORGANISM: Artificial Sequence
<220> FEATURE:
<223> OTHER INFORMATION: Synthetic: HVR1-deletion in Ad3M

<400> SEQUENCE: 58

Glu Trp Asp Ser Ala Ala Thr Ser Thr Ala Gly Gly
1               5                   10

<210> SEQ ID NO 59
<211> LENGTH: 67
<212> TYPE: PRT
<213> ORGANISM: Artificial Sequence
<220> FEATURE:
<223> OTHER INFORMATION: Synthetic: Ad5

<400> SEQUENCE: 59

Asn Pro Cys Glu Trp Asp Glu Ala Ala Thr Ala Leu Glu Ile Asn Leu
1               5                   10                  15

Glu Glu Glu Asp Asp Asp Asn Glu Asp Glu Val Asp Glu Gln Ala Glu
            20                  25                  30

Gln Gln Lys Thr His Val Phe Gly Gln Ala Pro Tyr Ser Gly Ile Asn
        35                  40                  45

Ile Thr Lys Glu Gly Ile Gln Ile Gly Val Glu Gly Gln Thr Pro Lys
    50                  55                  60

Tyr Ala Asp
65

<210> SEQ ID NO 60
<211> LENGTH: 78

```
<212> TYPE: PRT
<213> ORGANISM: Artificial Sequence
<220> FEATURE:
<223> OTHER INFORMATION: Synthetic: Ad2

<400> SEQUENCE: 60

Asn Ser Cys Glu Trp Glu Gln Thr Glu Asp Ser Gly Arg Ala Val Ala
1               5                   10                  15

Glu Asp Glu Glu Glu Glu Asp Glu Asp Glu Glu Glu Glu Glu Glu Glu
            20                  25                  30

Gln Asn Ala Arg Asp Gln Ala Thr Lys Lys Thr His Val Tyr Ala Gln
        35                  40                  45

Ala Pro Leu Ser Gly Glu Thr Ile Thr Lys Ser Gly Leu Gln Ile Gly
    50                  55                  60

Ser Asp Asn Ala Glu Thr Gln Ala Lys Pro Val Tyr Ala Asp
65                  70                  75

<210> SEQ ID NO 61
<211> LENGTH: 50
<212> TYPE: PRT
<213> ORGANISM: Artificial Sequence
<220> FEATURE:
<223> OTHER INFORMATION: Synthetic: Ad16

<400> SEQUENCE: 61

Asn Thr Cys Gln Trp Lys Asp Ser Asp Ser Lys Met His Thr Phe Gly
1               5                   10                  15

Val Ala Ala Met Pro Gly Val Thr Gly Lys Lys Ile Glu Ala Asp Gly
            20                  25                  30

Leu Pro Ile Gly Ile Asp Ser Thr Ser Gly Thr Asp Thr Val Ile Tyr
        35                  40                  45

Ala Asp
    50

<210> SEQ ID NO 62
<211> LENGTH: 50
<212> TYPE: PRT
<213> ORGANISM: Artificial Sequence
<220> FEATURE:
<223> OTHER INFORMATION: Synthetic: Ad4

<400> SEQUENCE: 62

Asn Thr Cys Gln Trp Lys Asp Ser Asp Ser Lys Met His Thr Phe Gly
1               5                   10                  15

Ala Ala Ala Met Pro Gly Val Thr Gly Lys Lys Ile Glu Ala Asp Gly
            20                  25                  30

Leu Pro Ile Arg Ile Asp Ser Thr Ser Gly Thr Asp Thr Val Ile Tyr
        35                  40                  45

Ala Asp
    50

<210> SEQ ID NO 63
<211> LENGTH: 56
<212> TYPE: PRT
<213> ORGANISM: Artificial Sequence
<220> FEATURE:
<223> OTHER INFORMATION: Synthetic: Ad3

<400> SEQUENCE: 63

Asn Thr Ser Gln Trp Ile Val Thr Thr Asn Gly Asp Asn Ala Val Thr
1               5                   10                  15
```

```
Thr Thr Thr Asn Thr Phe Gly Ile Ala Ser Met Lys Gly Asp Asn Ile
            20                  25                  30

Thr Lys Glu Gly Leu Gln Ile Gly Lys Asp Ile Thr Thr Thr Glu Gly
        35                  40                  45

Glu Glu Lys Pro Ile Tyr Ala Asp
    50                  55

<210> SEQ ID NO 64
<211> LENGTH: 65
<212> TYPE: PRT
<213> ORGANISM: Artificial Sequence
<220> FEATURE:
<223> OTHER INFORMATION: Synthetic: Ad21

<400> SEQUENCE: 64

Asn Thr Ser Gln Trp Ile Ala Glu Gly Val Lys Lys Glu Asp Gly Gly
1               5                   10                  15

Ser Asp Glu Glu Glu Glu Lys Asn Leu Thr Thr Tyr Thr Phe Gly Asn
            20                  25                  30

Ala Pro Val Lys Ala Glu Gly Gly Asp Ile Thr Lys Asp Lys Gly Leu
        35                  40                  45

Pro Ile Gly Ser Glu Ile Thr Asp Gly Glu Ala Lys Pro Ile Tyr Ala
    50                  55                  60

Asp
65

<210> SEQ ID NO 65
<211> LENGTH: 68
<212> TYPE: PRT
<213> ORGANISM: Artificial Sequence
<220> FEATURE:
<223> OTHER INFORMATION: Synthetic: Ad35

<400> SEQUENCE: 65

Asn Ala Ser Gln Trp Ile Ala Lys Gly Val Pro Thr Ala Ala Ala Ala
1               5                   10                  15

Gly Asn Gly Glu Glu Glu His Glu Thr Glu Glu Lys Thr Ala Thr Tyr
            20                  25                  30

Thr Phe Ala Asn Ala Pro Val Lys Ala Glu Ala Gln Ile Thr Lys Glu
        35                  40                  45

Gly Leu Pro Ile Gly Leu Glu Ile Ser Ala Glu Asn Glu Ser Lys Pro
    50                  55                  60

Ile Tyr Ala Asp
65

<210> SEQ ID NO 66
<211> LENGTH: 58
<212> TYPE: PRT
<213> ORGANISM: Artificial Sequence
<220> FEATURE:
<223> OTHER INFORMATION: Synthetic: Ad50

<400> SEQUENCE: 66

Asn Thr Ser Gln Trp Leu Asn Lys Gly Asp Glu Glu Asp Gly Glu Asp
1               5                   10                  15

Asp Gln Gln Ala Thr Tyr Thr Phe Gly Asn Ala Pro Val Lys Ala Glu
            20                  25                  30

Ala Glu Ile Thr Lys Glu Gly Leu Pro Ile Gly Leu Glu Val Pro Ser
        35                  40                  45

Glu Gly Gly Pro Lys Pro Ile Tyr Ala Asp
    50                  55
```

<210> SEQ ID NO 67
<211> LENGTH: 54
<212> TYPE: PRT
<213> ORGANISM: Artificial Sequence
<220> FEATURE:
<223> OTHER INFORMATION: Synthetic: Ad51

<400> SEQUENCE: 67

Asn Ser Ser Gln Trp Glu Gln Lys Lys Thr Thr Gly Gly Gly Asn Asp
1               5                   10                  15

Met Glu Thr His Thr Phe Gly Val Ala Ala Met Gly Gly Glu Asn Ile
            20                  25                  30

Thr Lys Asp Gly Leu Gln Ile Gly Thr Asp Thr Thr Ala Asp Ala Asp
        35                  40                  45

Lys Pro Ile Tyr Ala Asp
    50

<210> SEQ ID NO 68
<211> LENGTH: 54
<212> TYPE: PRT
<213> ORGANISM: Artificial Sequence
<220> FEATURE:
<223> OTHER INFORMATION: Synthetic: Ad9

<400> SEQUENCE: 68

Asn Ser Ser Gln Trp Leu Ala Lys Asp Thr Asn Ala Gly Asp Gln Ala
1               5                   10                  15

Leu Lys Thr His Thr His Gly Val Ala Ala Met Gly Gly Thr Asp Ile
            20                  25                  30

Thr Ala Lys Gly Leu Gln Ile Gly Val Asp Thr Thr Glu Asn Lys Asn
        35                  40                  45

Glu Pro Ile Tyr Ala Asn
    50

<210> SEQ ID NO 69
<211> LENGTH: 44
<212> TYPE: PRT
<213> ORGANISM: Artificial Sequence
<220> FEATURE:
<223> OTHER INFORMATION: Synthetic: Ad41

<400> SEQUENCE: 69

Asn Pro Cys Glu Trp Lys Asp Asn Asn Lys Ile Lys Val Arg Gly Gln
1               5                   10                  15

Ala Pro Phe Ile Gly Thr Asn Ile Asn Lys Asp Asn Gly Ile Gln Ile
            20                  25                  30

Gly Thr Asp Thr Thr Asn Gln Pro Ile Tyr Ala Asp
        35                  40

<210> SEQ ID NO 70
<211> LENGTH: 69
<212> TYPE: PRT
<213> ORGANISM: Artificial Sequence
<220> FEATURE:
<223> OTHER INFORMATION: Synthetic: RGD-loop-mutated penton base -
     a3b1-integrin-binding peptide

<400> SEQUENCE: 70

Asp Ala Tyr Gln Ala Ser Leu Lys Asp Asp Thr Glu Gln Gly Gly Gly
1               5                   10                  15

-continued

```
Gly Ala Gly Gly Ser Asn Ser Ser Gly Ser Gly Cys Asn Gly Gln Gly
                20                  25                  30

Glu Gln Cys Ala Ala Ala Glu Ala Ala Pro Ala Ala Gln Pro Glu
            35                  40                  45

Val Glu Lys Pro Gln Lys Lys Pro Val Ile Lys Pro Leu Thr Glu Asp
        50                  55                  60

Ser Lys Lys Arg Ser
65

<210> SEQ ID NO 71
<211> LENGTH: 70
<212> TYPE: PRT
<213> ORGANISM: Artificial Sequence
<220> FEATURE:
<223> OTHER INFORMATION: Synthetic: RGD-loop-mutated penton base -
      a5b1-integrin-binding peptide

<400> SEQUENCE: 71

Asp Ala Tyr Gln Ala Ser Leu Lys Asp Asp Thr Glu Gln Gly Gly Gly
1               5                   10                  15

Gly Ala Gly Gly Ser Asn Ser Ser Gly Ser Gly Arg Lys Lys Arg Arg
                20                  25                  30

Gln Arg Arg Arg Ala Ala Ala Glu Ala Ala Ala Pro Ala Ala Gln Pro
            35                  40                  45

Glu Val Glu Lys Pro Gln Lys Lys Pro Val Ile Lys Pro Leu Thr Glu
        50                  55                  60

Asp Ser Lys Lys Arg Ser
65                  70
```

DETARGETED ADENOVIRUS VARIANTS AND RELATED METHODS

The present application is a continuation application of U.S. patent application Ser. No. 15/537,392, filed on Jun. 16, 2017, which is a National Stage Application of International Application No. PCT/US16/013765, filed on Jan. 17, 2016, which claims priority to U.S. Provisional Application No. 62/105,284, filed on Jan. 20, 2015. The entirety of the aforementioned application is incorporated herein by reference.

This invention was made with the U.S. government support under grant numbers AI064882 and AI065429 awarded by the National Institutes of Health. The government has certain rights in the invention.

I. FIELD OF THE INVENTION

This invention relates to the field of gene therapy, and in particular, to novel Adenovirus (Ad) vectors, which escape sequestration in the liver tissue at a physical particle level and induce diminished inflammatory response upon intravascular injection. These vectors can be a safe and useful tool for infecting cells in vivo for gene therapy, including for treatment of localized and disseminated metastatic cancers, in any organ of the body, including of the hematopoietic and non-hematopoietic origin.

II. BACKGROUND OF THE INVENTION

Adenoviruses (Ads) are promising vectors for therapeutic interventions in humans (Thomas et al., 2003). Despite significant knowledge regarding the biology of Ad interactions with cells in vitro, the molecular mechanisms governing in vivo Ad infectivity and bio-distribution remain poorly understood (Baker, 2007; Khare et al.). This poses significant risks for their intravascular administration and represents the major hindrance for safe, selective, and efficient Ad targeting to specific cell and tissue types in vivo.

Pharmacokinetic studies of Ad vectors after intravascular delivery demonstrate that the majority of an administered virus dose is rapidly sequestered from the circulation by the liver (Alemany and Curiel, 2001; Di Paolo et al., 2009b; Khare et al., 2011a). Through comprehensive in vivo analyses, it was found that the general molecular mechanisms that mediate Ad sequestration by liver tissue operate in a redundant and synergistic manner (Di Paolo et al., 2009b). Specifically, it is currently believed that Ad particles are distributed in liver tissue amongst three distinct cellular compartments, namely i) parenchymal liver cells—hepatocytes, ii) hepatic residential macrophages, Kupffer cells, and iii) hepatic sinusoid endothelial cells. Importantly, the ablation of Ad interaction with only one of these cellular compartments cannot prevent virus trapping the liver and results in compensatory re-distribution of the virus among two remaining cellular compartments, functionally ensuring the quantitative removal of the virus from the blood (Di Paolo et al., 2009b). Despite of this general understanding of the redundancy of mechanisms that may operate to remove Ad particles from the blood and trap them in the liver after intravascular virus administration, the exact molecular mechanisms guiding Ad interactions with liver cells in vivo remain controversial (Baker et al., 2013). This controversy and the lack of understanding of mechanisms that operate to trap Ad particles in the liver is ultimately manifested in the fact that to date, no Ad vector configurations were reported that would, based on purely genetic (and not chemical) modification of Ad capsid proteins, allow for generation of Ads, which would escape being sequestered in the liver at a physical particle level after intravascular virus delivery. Ad trapping in the liver is deleterious for gene therapy and cancer therapy applications, since Ad particles sequestered in the liver become destroyed, necessitating high virus doses to achieve transduction of any extra-hepatic cells. High Ad doses injected intravenously activate severe systemic inflammatory response that can be fatal (Brunetti-Pierri et al., 2004; Raper et al., 2003; Raper et al., 2002). What is needed are new Ad vectors that avoid liver sequestration and activation of inflammation and methods of accomplishing the same.

III. SUMMARY

The present invention provides for novel modified Ad vectors that contain simultaneous genetic modifications in Ad penton and hexon proteins, which are introduced to prevent virus binding to liver cells, including hepatocytes, endothelial cells, and Kupffer cells, and allow for virus to exhibit greatly reduced or completely eliminated trapping in the liver tissue and inflammatory responses after virus particles circulate in the blood.

The one embodiment of the invention are isolated Ads with a mutation in the RGD motif of the penton protein, wherein the mutation causes reduced binding of $\beta_3$ integrins of a host cell in vivo, such as macrophages or endothelial cells, and induce significantly reduced inflammatory responses after virus circulate in blood in vivo.

The preferred embodiment of the invention provide for novel Ad vectors where, as an example in a context of the most commonly used in gene therapy applications human species C serotype Ad5-based vectors, three simultaneous mutations are necessary and sufficient to prevent virus binding to liver cells in vivo—one mutation is in the Ad penton RGD loop and two mutations are in Ad hexon hypervariable loops, specifically in the loops HVR1 and HVR7.

Also the example of the embodiment of the invention is isolated nucleic acids encoding an Ad penton protein, the penton protein comprising a mutation in the RGD motif of the penton protein, wherein the mutation causes reduced binding of a host cell β3 integrin proteins in vivo, when expressed in an Ad.

The invention also provides methods of administering an Ad such that the Ad virions evade sequestration in a host's liver in vivo, wherein the method comprises the steps of: a) providing an Ad with a mutation in the RGD motif of the penton protein, wherein the mutation causes reduced binding of β3 integrins of a host normal liver cells; b) reducing the binding of the Ad with a vitamin K dependent clotting factor in the host; and, c) reducing the binding of the Ad to Kupffer cells.

The invention also provides methods of delivering a gene to a non-hepatic mammalian cell, including localized and disseminated metastatic cancer cells, wherein the method comprises the steps of: a) providing an Ad with a mutation in the RGD motif of the penton protein, wherein the mutation causes reduced binding of $\beta_3$ integrins of a host of the normal liver cell in vivo; b) providing an Ad with a mutation in Ad hexon protein hypervariable region 1, HVR1; c) providing an Ad with a mutation in Ad hexon protein hypervariable region 7, HVR7; and d) contacting the host cell with the Ad in vivo.

IV. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the sequestration of blood-borne Ad in the liver tissue after intravenous virus injection does not depend on the fiber structure. One hour after intravenous Ad injection, livers were recovered from mice and the total DNA was purified as described herein. Ten μg of total DNA, digested with HindIll enzyme, were loaded onto the agarose gel. Following transfer to a Nybond-N+ membrane, filters were hybridized with a mouse β-glucuronidase-specific probe to confirm equivalent loads (Gus). Subsequently, the membranes were stripped and rehybridized with an Ad-specific probe (Ad). Control—DNA purified from livers of mice injected with PBS only.

FIGS. 2A, 2B, and 2C show the sequestration of blood-borne Ad in the liver tissue after intravenous virus injection occurs independently of virus binding to blood coagulation factors. FIG. 2A shows that Ad5 vector was injected into mice mock treated (Ad5 lanes) or pre-treated with warfarin (Warfarin lanes) and livers were harvested 1 h after virus injection and processed for Southern blotting as described in FIG. 1. Each lane represents liver samples harvested from a mouse individually injected with Ad (biological replicates). FIG. 2B shows the association of Ad vectors with Kupffer cells (KCs) of mice treated with warfarin or mock-treated controls. Ad5 were injected into the tail vein of C57BL/6 mice. One hour later, livers were recovered and immediately frozen in an OCT compound. To visualize KCs, fixed liver sections were stained with anti-F4/80 antibody. Ad particles were visualized after staining the liver sections with Cy3-labeled anti-hexon polyclonal Abs. Images of representative fields were taken with red and green filters and were then superimposed to reveal Ad association with KCs. The overlapping of Kupffer cell-specific staining and Ad-specific staining is indicated by arrows. FIG. 2C shows Southern blot analysis of genomes of wild type human Ad present in the liver 1 h after intravenous virus injection. Affinity of FX binding for indicated serotypes is shown. Gus-mouse β-glucuronidase gene. Control—liver DNA from a mouse injected with virus dilution buffer (PBS) only.

FIGS. 3A and 3B show that inactivation of blood coagulation factors leads to Ad transduction of liver sinusoid endothelial cells. FIG. 3A shows in vivo transduction of hepatocytes with Ad5RFP after systemic vector application in control, mock-treated and warfarin-treated mice. Twenty-four hours after intravenous Ad injection, livers were recovered and serial sections of formalin-fixed tissues were prepared. To visualize RFP fluorescence, images of sections were taken under UV light. Representative fields are shown. Magnification, 200× on the two left sets of panels and 400× on the right sets of panels. Note that the treatment of mice with warfarin completely eliminates hepatocyte transduction. However, sinusoid endothelial cells express RFP (indicated by arrows) in warfarin-treated mice. Two representative fields are shown. FIG. 3B shows analysis of surface markers of RFP-expressing cells in warfarin-treated mice using flow cytometry. Note that the RFP expressing cells are stained positive with antibody for CD31, endothelial cell marker.

FIGS. 4A, 4B, 4C, and 4D show that Kupffer cell elimination does not prevent the sequestration of blood-borne Ad in the liver. FIG. 4A shows the association of Ad vectors with Kupffer cells of wild type mice (WT) or mice knockout for scavenger receptor-A (SR-A-KO) gene. One hour after intravenous virus injection, livers were recovered and immediately frozen in OCT compound. To visualize KCs, fixed liver sections were stained with anti-F4/80 antibody. Ad particles were visualized after staining liver sections with Cy3-labeled antihexon polyclonal Abs. Images of representative fields were taken with red and green filters and were then superimposed to reveal Ad association with KCs. The overlapping of Kupffer cell-specific staining and Ad-specific staining is indicated by arrows. FIG. 4B shows Southern blot analysis for Ad vector genomes associated with livers of wild type and SR-A-KO mice 1 h after intravenous virus injection. Biological duplicates are shown. Gus—mouse β-glucuronidase gene. Control—liver DNA from a mouse injected with virus dilution buffer (PBS) only. FIG. 4C shows wild type mice were treated with clodronate liposomes as described herein. One hour after intravenous virus injection, livers were recovered and immediately frozen in OCT compound. To visualize KCs, fixed liver sections were stained with anti-F4/80 antibody. Note, that the treatment of mice with clodronate liposomes completely eliminates Kupffer cells from the liver. FIG. 4D shows Southern blot analysis for Ad vector genomes associated with livers of wild type mice treated with clodronate liposomes 1 h after intravenous virus injection. Biological duplicates are shown. Gus—mouse β-glucuronidase gene. Control—liver DNA from a mouse injected with virus dilution buffer (PBS) only.

FIGS. 5A, 5B, and 5C show that the treatment of mice with warfarin and clodronate liposomes allows for a partial reduction of the amounts of Ad DNA sequestered by the liver after intravenous virus administration. FIG. 5A shows Southern blot analysis for Ad vector genomes associated with livers of wild type mice 1 h after intravenous virus injection. Mice were treated with warfarin only or with a combination of warfarin and clodronate liposomes. Duplicate samples for each group are shown. Gus—mouse β-glucuronidase gene. Control—liver DNA from a mouse injected with virus dilution buffer (PBS) only. FIG. 5B shows quantitative representation of Ad accumulation in livers determined by PhosphorImager analysis of Ad-specific bands shown in (A) after adjustment of Ad DNA signal intensities for the Gus gene signal intensities for corresponding vectors. *–P<0.05. FIG. 5C shows the distribution of Ad particles in the livers of mice treated with warfarin or with a combination of warfarin and clodronate liposomes 1 h after intravenous virus injection. Liver sections were stained with anti-F4/80 antibody to detect Kupffer cells and with anti-Ad hexon antibody to detect Ad particles. Note that the large number of Ad particles was colocalized with Kupffer cells in warfarin treated animals, while Ad particles were associated with liver sinusoids in mice treated with both of drugs.

FIGS. 6A, 6B show a visualization of Ad distribution in liver tissue 1 hour after intravenous virus injection. FIG. 6A shows Ad particles present in hepatic sinusoids in a space of Disse; Magnification of main image: 4,400×; enlarged image 21,000×. FIG. 6B shows a representative image showing distribution of free Ad particles in the Disse space (indicated by arrows). Magnification 7,500×. S—liver sinusoidal space; H—hepatocyte; D—Disse space.

FIGS. 7A, 7B, 7C, 7D show that Ad penton RGD motifs play a role in supporting the sequestration of the blood-borne Ad in the liver. FIG. 7A shows wild type (WT) or β3-integrin knockout mice (β3-KO) were treated with a combination of warfarin and liposomes and injected intravenously with Ad5 vector. In addition to drug treatment, WT mice were also injected with Ad5ΔRGD vector. One hour after virus injection, livers were harvested, total liver DNA was purified and then subjected to a Southern blot analysis as described in FIG. 1. Duplicate samples for each group are shown. Gus—mouse β-glucuronidase gene. Control—liver DNA from a mouse injected with virus dilution buffer (PBS) only. FIG. 7B shows quantitative representation of Ad accumulation in livers determined by PhosphorImager analysis of Ad-specific bands shown in (A) after adjustment of Ad DNA signal intensities for the Gus gene signal intensities for corresponding vectors. ~P<0.05. **–P<0.01. FIG. 7C shows distribution of Ad particles in the livers of wild type or β3-KO mice 1 h after intravenous virus injection. Liver sections were stained with anti-F4/80 antibody to detect Kupffer cells and with anti-Ad hexon antibody to detect Ad particles. Colocalization of Ad-specific staining with Kupffer cell staining appears in yellow (Merged) and is indicated by arrows. FIG. 7D shows distribution of Ad and Ad5ΔRGD particles in the livers of mice treated with a combination of warfarin and clodronate liposomes 1 h after intravenous injection. Liver sections were stained with anti-F4/80 antibody to ensure complete elimination of Kupffer cells with clodronate liposomes as well as with DAPI and anti-Ad hexon antibody to detect Ad particles.

FIGS. 8A and 8B show that sequestration of blood-borne Ad5ΔRGD vector in the liver is reduced only in mice treated with both warfarin and clodronate liposomes. FIG. 8A shows wild type mice were individually treated with a saline, warfarin, clodronate liposomes, or a combination of warfarin and liposomes and injected intravenously with Ad5ΔRGD vector. One hour after virus injection, livers were harvested, total liver DNA was purified and subjected to Southern blot analysis as described in FIG. 1. Duplicate samples for each group are shown. Gus—mouse β-glucuronidase gene. Control—liver DNA from a mouse injected with virus dilution buffer (PBS) only. FIG. 8B shows quantitative representation of Ad5ΔRGD accumulation in livers determined by PhosphorImager analysis of Ad-specific bands shown in (A) after adjustment of Ad DNA signal intensities for the Gus gene signal intensities for corresponding vectors. *P<0.05.

FIG. 9 shows a schematic representation of cellular compartment in the liver mediating the sequestration of blood-borne Ad and approaches to inactivate them. CL—clodronate liposomes; PI—polyinosinic acid; FX-bp—FX-binding protein.

FIGS. 10A-10B show an embodiment of the invention illustrating a single Ad genomic DNA FIG. 10A and virus particle capsid FIG. 10B possessing simultaneous mutations in both hexon (pII) and penton base (pIII) proteins, preventing virus trapping in the liver after intravascular injection and description of functional effects of the hexon and penton mutations.

FIGS. 11A and 11B show the amino acid sequence alignment for Ad5 and other representative human Ad serotypes Ad3, Ad16, Ad14, and Ad35, depicting consensus location and diversity of solvent-exposed surface-localized hyper-variable loops of the Ad hexon protein. Hypervariable exposed loops 1-9 (HVR1-HVR9) of hexons are underlined. The exact position of conservative coagulation factor binding motifs TDT and TET within HVR3 and HVR7 are boxed.

FIGS. 12A, 12B, 12C, 12D and 12D, continued show the determination of putative Factor X binding site on Ad5 hexon. FIG. 12A shows the CryoEM structure of the Ad5-FX complex together with the strongest FX density. The FX density was generated by subtracting a cryoEM reconstruction of the Ad5 capsid from that of the Ad5-FX complex. The strongest FX density appears in the central depression of each hexon trimer. Scale bar, 100 Å. FIG. 12B shows the crystal structure of Ad5 hexon (PDB 1P30) shown in a ribbon representation and as a density map filtered to 30 Å resolution (transparent gray). Both 45° tilt and top views are shown. FIG. 12C shows a top view of the hexon density with fitted crystal structure of the Ad5 hexon trimer as in (FIG. 12B) shown together with the strongest FX density (arrow). FIG. 12D shows the amino acid sequence alignment of the hexon HVR3 and HVR7 regions for the 11 human Ad serotypes tested for FX binding (FIG. 12D, Continued). The positions of the two alternative sites proposed for FX binding are indicated by asterisks. Nearby positively charged Arg residues that can ablate or reduce FX binding affinity are highlighted by the black box.. The ( )ines separate Ad serotypes that bind FX (above the line) from those that don't bind FX (below the line). FIG. 12D, continued shows FX binding affinity to selected human adenovirus serotype species.

FIGS. 13A, 13B, 13C, 13D, 13E, and 13F show the Cryo-EM structure of the FX-Ad5 complex and simulation of the FX-hexon interface using molecular dynamics flexible fitting (MDFF). FIG. 13A shows the cryo-EM structure of Ad5 in complex with FX. Scale bar, 100 Å. FIG. 13B shows an enlarged view of the FX-Ad5 complex showing the network of the FX density above the hexon capsid. FIG. 13C shows the best rigid-body fit orientation of the zymogenic FX model within FX cryo-EM density This FX density is selected from above a hexon near the icosahedral threefold axis of the capsid. FIG. 13D shows coordinates from a frame in the MDFF simulation that show hexon residues E424 and T425 surround residue K10 of the FX-GLA domain. The side chains of these three residues are shown in space-filling representation. FIG. 13E shows FX-GLA domain and associated $Ca_2^+$ ions (gray spheres) in the central depression of the hexon timer. FIG. 13F shows residue K10 in the FX-GLA domain is in dose enough proximity to E424 and T425 of hexon to engage in dectrostatic interactions (depicted by the dotted lines).

FIGS. 14A, 14B, 14C, 14D, 14E, 14F, 14G, 14H show that a single amino acid substitution, T425A, abrogates FX biding to Ad5. FIG. 14A shows the schematic diagram of a region of Ad5 hexon hypervariable loop 7 (HVR7) showing T423-E424-T425 amino acids and amino acid substitutions introduced in this region of individual viruses with mutated hexons (shown in solid black). FIG. 14B shows kinetic response data and dissociation constant (Kd) for FX binding to the indicated mutant viruses obtained by using surface plasmon resonance analysis (Biacore, GE Healthcare Biosciences, Pittsburgh, Pa.). Black indicates experimentally obtained data. Representative data obtained from four independent experiments are shown. FIG. 14C to 14F show in vitro and in vivo analyses of hexon-mutated viruses. FIG. 14C shows infection of CHO-K1 cells with indicated viruses with or without the addition of FX (8 μg ml-1). Cells were infected with a multiplicity of infection of 200 v.p. cell-1. Mean fluorescent intensity of virus-encoded GFP reporter protein was analyzed by flow cytometry 24 h after virus infection. N=6. *P<0.01. n.s.—not significant. FIG. 14D shows histological analysis of virus-encoded GFP expression in mouse hepatocytes 48 hours after intravenous infection of mice with WT Ad5 (WT) or mutated viruses. Representative fields are shown (n=5 biological replicates). GFP expression is observed as fluorescence on fixed liver sections. Corresponding fields in 4',6-diamidino-2-phenylindole channel are shown. Scale bar, 100 μm. FIG. 14E shows western blotting analysis and GFP signal quantification (FIG. 14F) of GFP expression in the livers of mice shown in (FIG. 14D). The biological duplicate samples for each virus are shown. FIG. 14G shows colocalization of virus particles with splenic CD169+ and MARCO+ marginal zone macrophages observed 1 hour after infection for indicated viruses analyzed by means of confocal microscopy. FIG. 14H shows high power images of Ad particles colocalized with marginal zone macrophages. Scale bar, 10 μm. Representative fields are shown. n=5 biological replicates.

FIGS. 15A, 15B, 15C, 15D, 15E, 15F show Ad5 binding to FX induces NF-κB1—dependent inflammatory cytokines and chemokines downstream of the TLR4-TRIF/MyD88-TRAF6 signaling axis in vivo. FIG. 15A shows a mouse cytokine array panel showing differences in inflammatory cytokines and chemokines in the spleens of WT mice 1 hour after infection with HAdv5 or TEA mutant, determined by means of proteome profiler antibody array. Representative blot from four independent experiments is shown. C, mouse was challenged with saline. FIG. 15B shows mRNA expression of IL-1β in the spleen of WT mice 30 min after challenge with indicated viruses. Graphs show mean±SD, n=4 biological replicates, P<0.01. AU, arbitrary units reflecting IL-1β to glyceraldehyde-3-phosphate dehydrogenase (GAPDH) mRNA ratios. FIGS. 15C and 15D show mRNA expression of IL-1β in the spleen of WT mice and mice deficient for indicated genes 30 min after challenge with HAdv5. Graphs show mean±SD, n=4 biological replicates, P<0.01. AU, arbitrary units reflecting IL-1β to GAPDH mRNA ratios. FIG. 15E shows mouse cytokine array panel showing differences in inflammatory cytokines and chemokines in the spleens of WT and Myd88$^{-/-}$, Ticam1$^{-/-}$, Tlr4$^{-/-}$, and Md2$^{-/-}$ mice 1 hour after challenge with HAdv5, determined by means of proteome profiler antibody array. Representative blot from four independent experiments is shown. C, mouse was challenged with saline. FIG. 15F shows mouse cytokine array panel showing differences in inflammatory cytokines and chemokines in the spleens of WT mice 1 hour after challenge with WT human Ads of indicated serotypes, determined by means of proteome profiler antibody array. Representative blot from four independent experiments is shown. C, mouse was mock infected with saline.

FIG. 16 shows amino acid sequence alignment of the penton base proteins (pIII) from different human Ad serotypes. The large hypervariable exposed RGD-motif containing loop is highlighted.

Figure 18A:
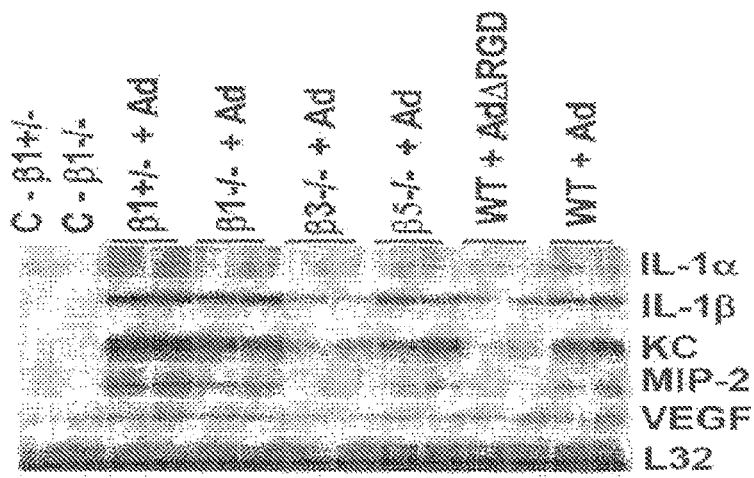
Figure 18B:
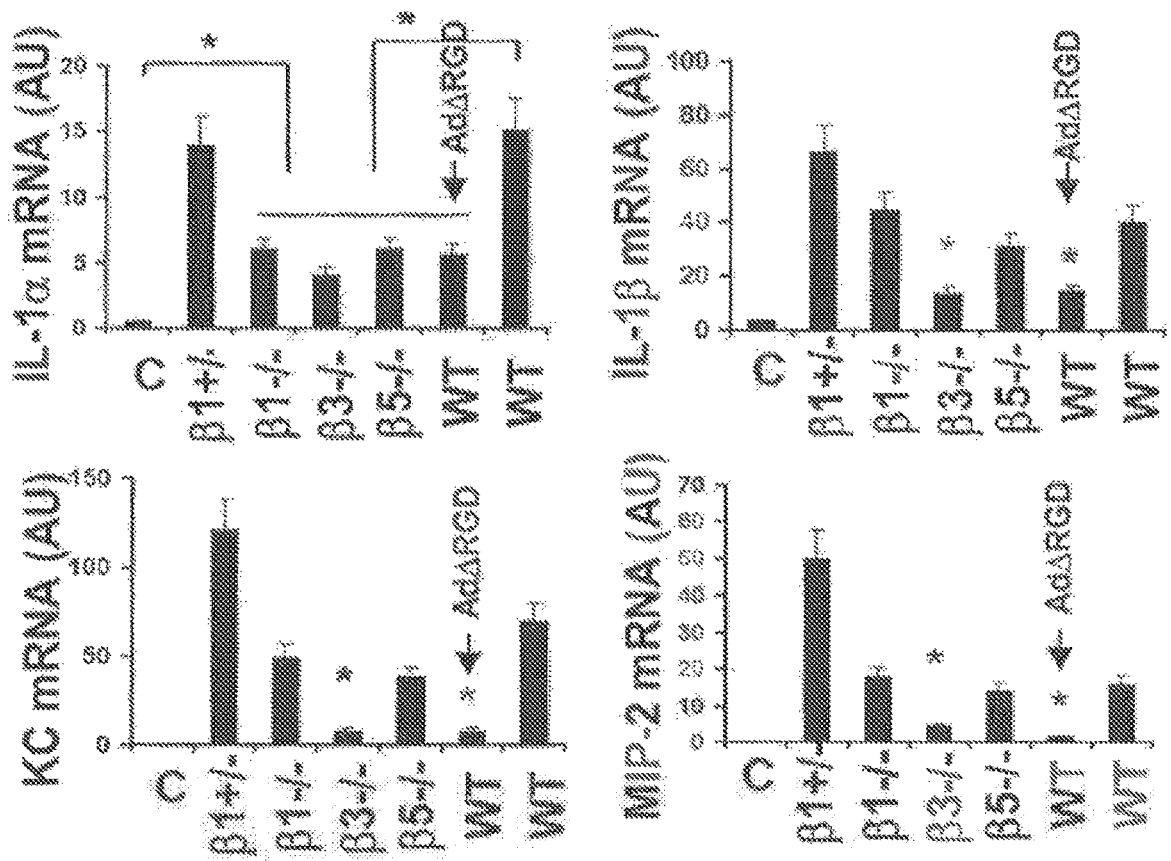
Figure 18C:
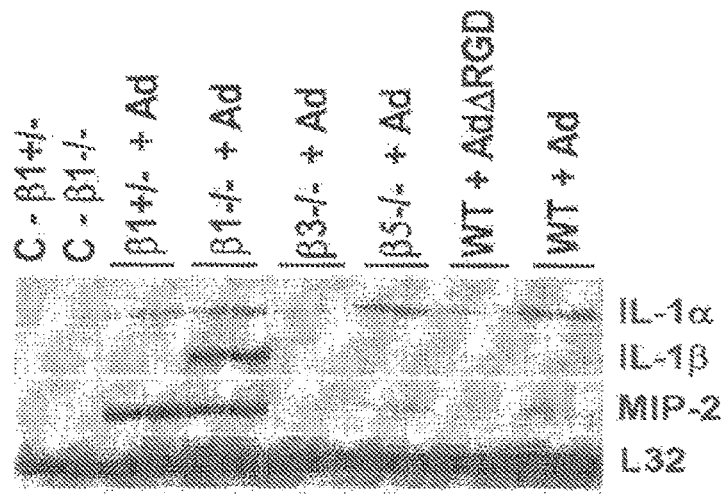
Figure 18D:
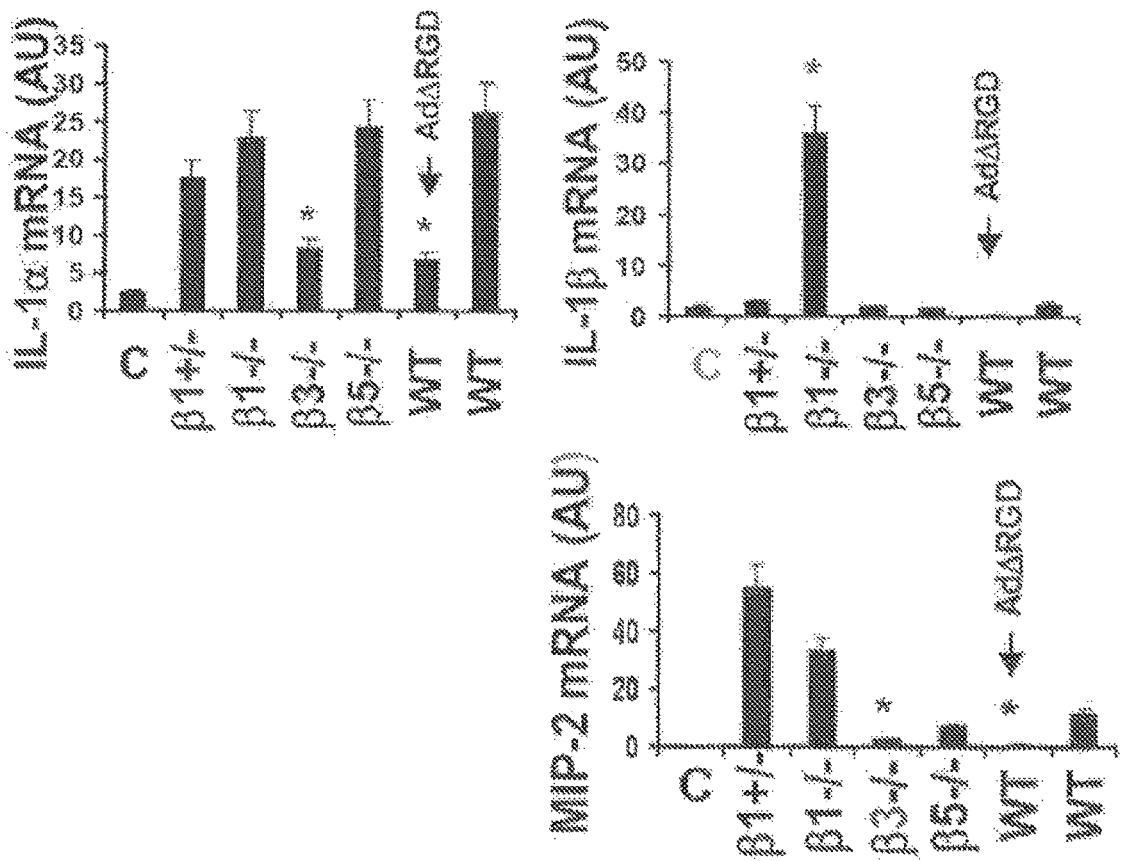
Figure 18E:
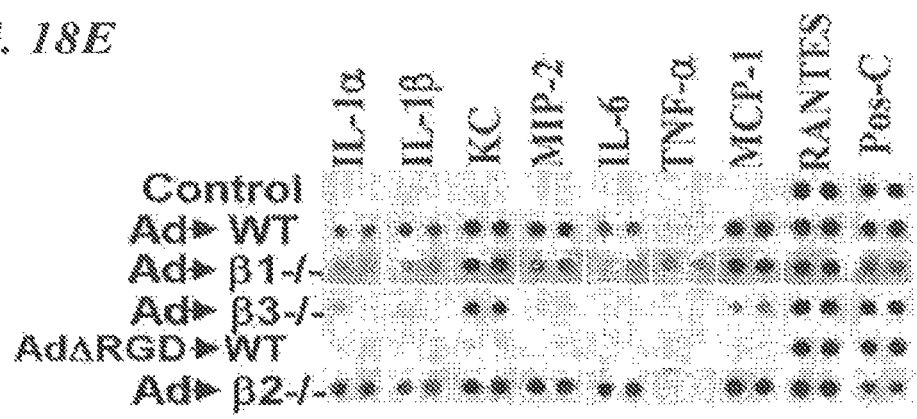
Figure 18F:
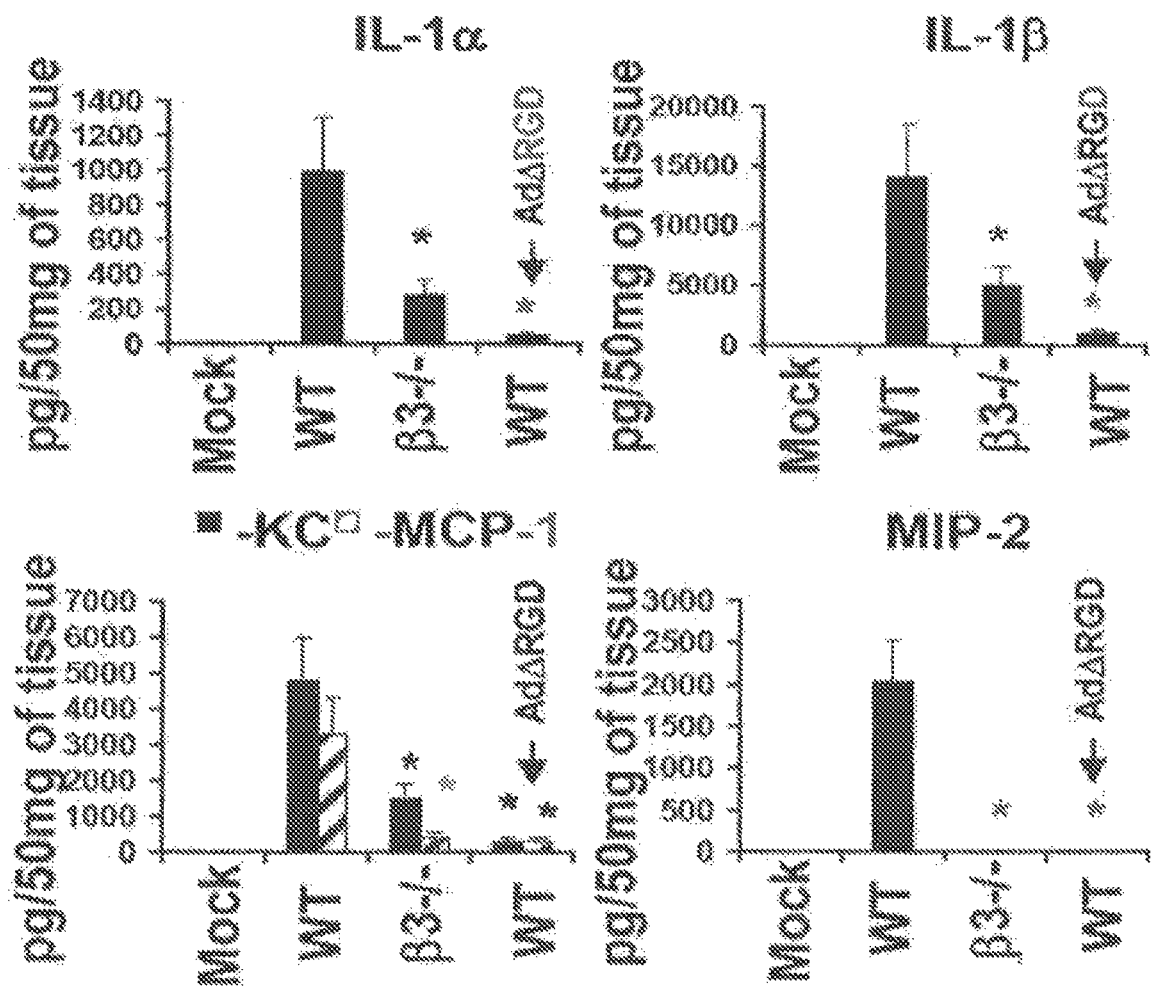

FIGS. 18A, 18B, 18C, 18D, 18E, and 18F show the engagement of β$_3$ integrins by Ad5 is involved in the initiation of the innate immune response. FIG. 18A shows the mRNA levels for IL-1α, IL-1β, KC and MIP-2 in spleens of wild type mice (WT) and mice knockout for β$_3$-, β$_5$-, or conditionally knockout for β$_1$-integrin in hematopoietic cells (β$_1^{-/-}$), as well as WT mice injected with Ad mutant lacking an RGD motif within its penton protein (Ad5ΔRGD) 30 min after virus injection. N=3. C—mock-infected mice, injected with saline. FIG. 18B shows quantitative representation mRNA levels from the gel shown in (18A) after phosphorimager analysis. N=6. Statistically significant differences between experimental groups and mock-injected controls [C] or WT injected with Ad are indicated by the star. *–P<0.01. WT mice injected with Ad5ΔRGD are indicated by the arrow. AU—arbitrary units. FIG. 18C shows IL-1α, IL-1β, and MIP-2 mRNA levels in livers of mice shown in (18A). N=3. FIG. 18D shows quantitative representation mRNA levels from the gel shown in (18C) after phosphorimager analysis. N=6. Statistically significant differences between experimental groups and WT mice injected with Ad are indicated by the star. *–P<0.01. FIG. 18E shows protein levels of cytokines and chemokines in spleens of mice knockout for integrins β$_1$, β$_2$, β$_3$, or WT mice injected with Ad or Ad5ΔRGD 1 hour after virus injection. N=4. Pos-C are dots that show the manufacturer's internal positive control samples on the membrane. Control—the spleen protein sample of a mouse injected with saline. FIG. 18F shows the amounts of cytokines and chemokines in the spleens of mice 1 hour after Ad injection. N=4. Mock—negative control mice injected with saline. Statistically significant differences between experimental groups and WT mice injected with Ad are indicated by the star. *–P<0.01.

Figure 19:
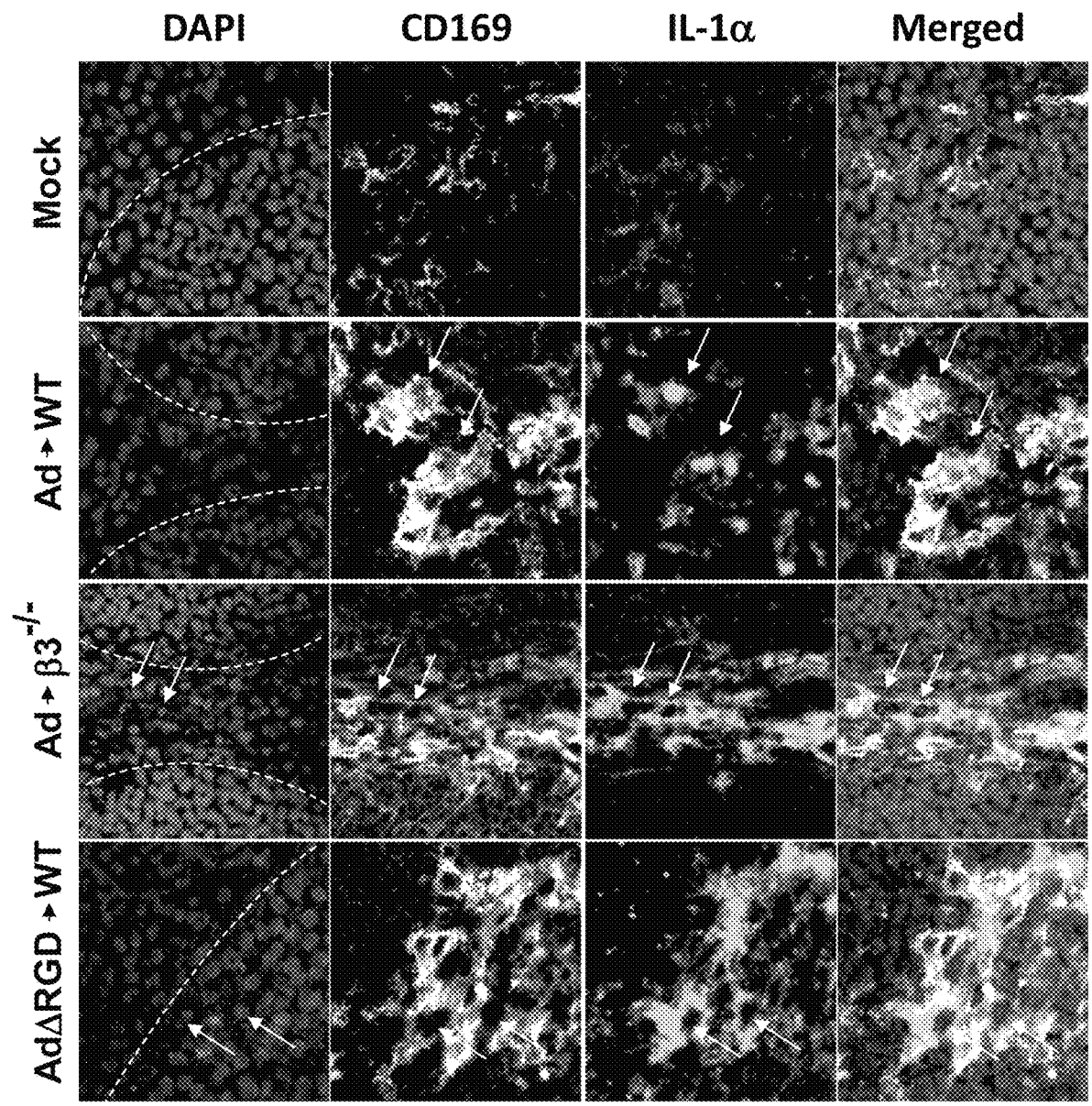

FIG. 19 shows confocal microscopy analysis of IL-1α translocation into the nuclei of marginal zone macrophages in WT mice and β$_3$ integrin knockout mice injected with Ad, or WT mice injected with AdΔRGD mutant. Mice were injected intravenously with a high dose of the indicated viruses (10$^{11}$ virus particles per mouse), and 3 hours later spleens were harvested and sections were prepared and stained with DAPI to detect nuclei of splenocytes, as well as Abs specific for CD169 or IL-1α. Confocal images were obtained using a Zeiss 510 Meta Confocal microscope. The physical borders of splenic germinal centers are indicated by punctuate lines. Marginal zone macrophages expressing IL-1α are indicated by arrows. Representative pictures are shown. N=4.

FIG. 20 shows a schematic representation of the design of Ad5 penton modified vectors and specific examples of large substitutions introduced in Ad5 penton RGD loop, containing substitutions of natural Ad5 penton amino acid sequences for amino acid sequences from human laminin 1 (50 amino acids-long) or laminin 3 (54 amino acids-long) and designation of the resultants vectors as Lam1 and Lam3 correspondingly. dRGD is Ad5ΔRGD virus containing RGD amino acids deleted in penton protein. The numbering of amino acids shown corresponds to amino acid numbering in wild type Ad5 penton.

Figure 21A:
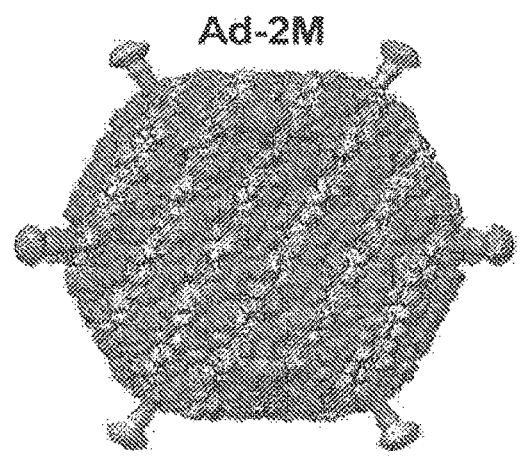
Figure 21B:
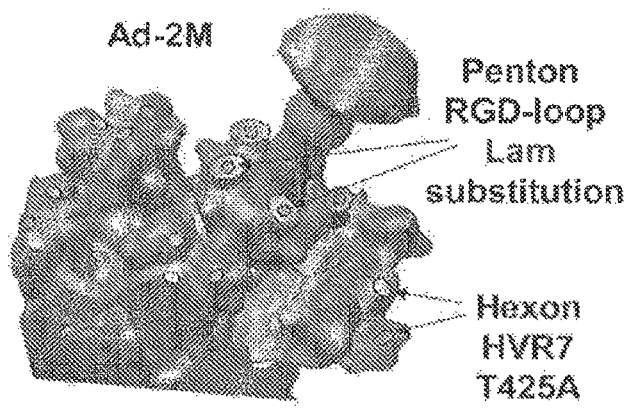
Figure 21C:
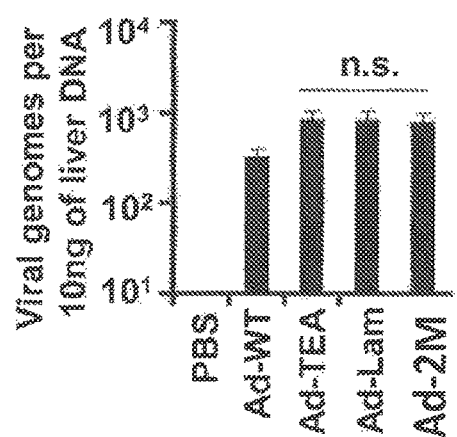
Figure 21D:
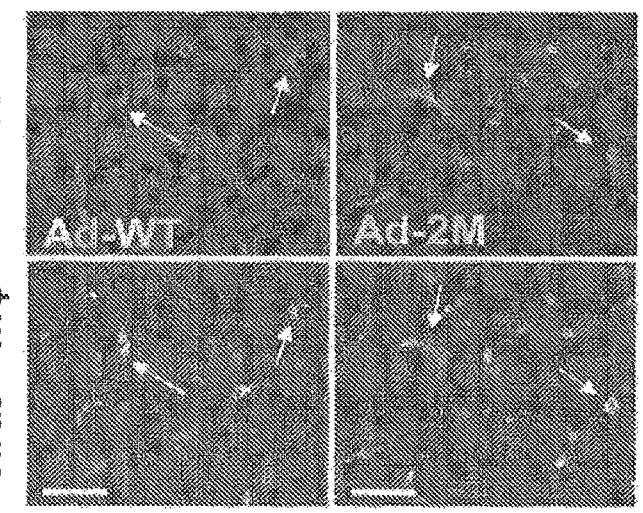

FIGS. 21A, 21B, 21C, and 21D show the introduction of simultaneous mutations in the penton and FX-binding site of the hexon does not prevent Ad sequestration in the liver after intravascular administration. FIGS. 21A and 21B show the structural determinants of Ad5-based vector Ad-2M, which contains mutations in both the penton (Lam3 substituting mutation, as shown in FIG. 20) and hexon HVR7 T425A substitution. The quantitative PCR analysis of the amounts of Ad genomic DNA in the liver 1 hour after intravenous injection of the indicated vectors at a dose of 2×10$^{10}$ virus particles per mouse. Ad-WT is Ad5-based vector containing no mutations in the capsid proteins. Ad-TEA is a vector containing single amino acid substitution in the hexon HVR7, T425A, which abrogates binding of blood coagulation factors. Ad-Lam is Ad vector containing Lam3 substitution within penton RGD loop as shown in FIG. 20. FIG. 21D shows the co-localization of virions of Ad-WT and Ad-2M (shown by arrows) with F-4/80-positive Kupffer cells in the liver 1 hour after intravenous virus injection. Virus was stained with anti-hexon Ab. Note that Kupffer cells efficiently accumulate both Ad-WT and Ad-2M vectors.

Figure 22:
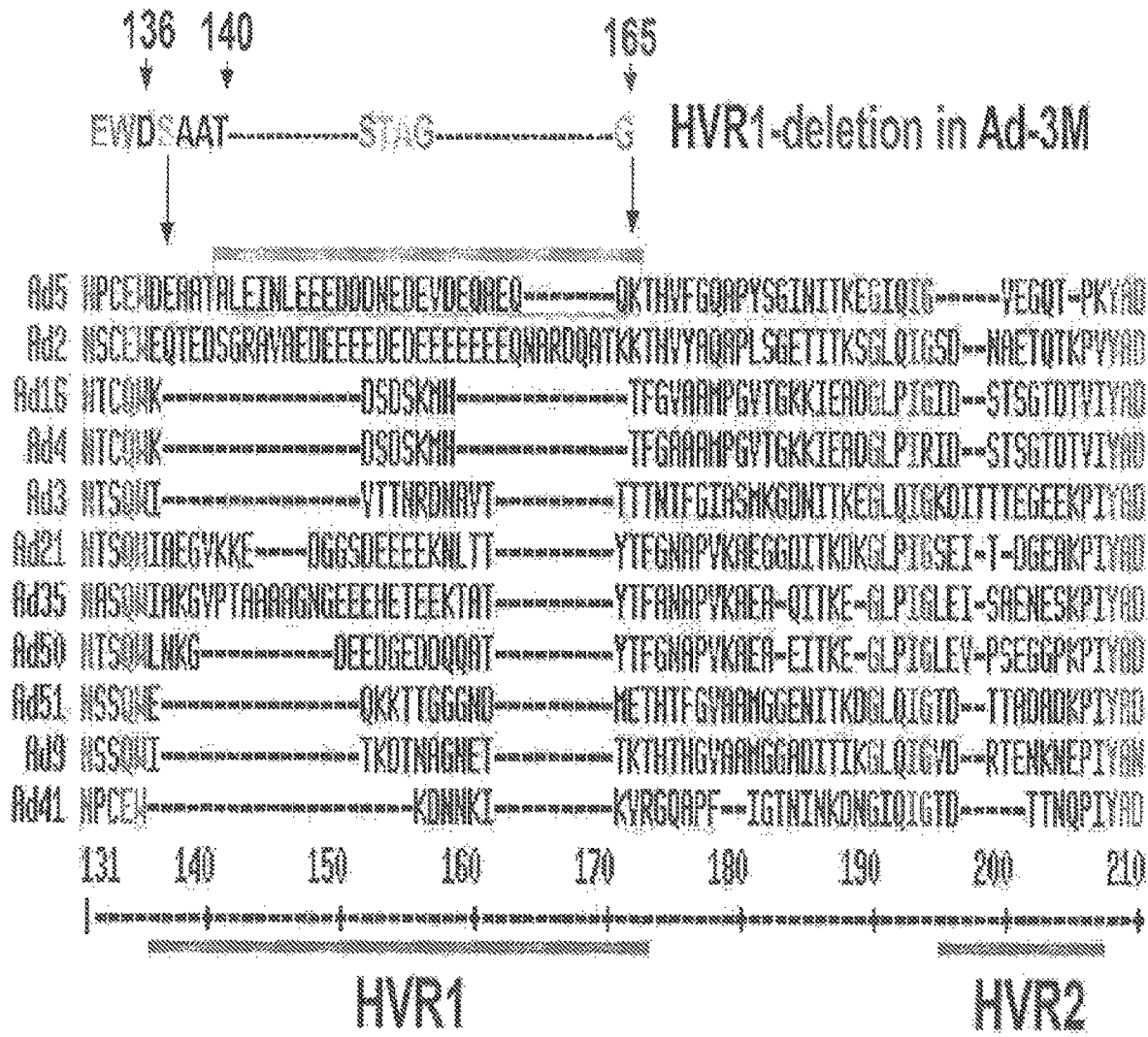

FIG. 22 shows natural variation of hexon hyper-variable loop 1 (HVR1) amino acid sequences and length among indicated representative human Ad serotypes and amino acid sequence of HVR1 deletion/substitution mutation 136-DSAATSTAGGT-165, introduced into Ad5 hexon HVR1 loop in place of the natural amino acid sequence, located between amino acids 136D and 165T. This HVR1 mutation was introduced into Ad5-based vector in ADDITION to T425A mutation in HVR7 and penton Lam3 mutation/ substitution, resulting in generation of a novel vector, Ad-3M, which contains three specific and discrete capsid protein mutations simultaneously and represents the preferred embodiment of the invention.

Figure 23A:
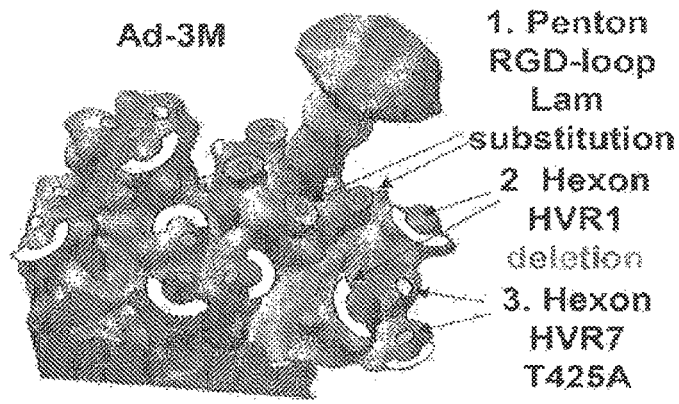
Figure 23B:
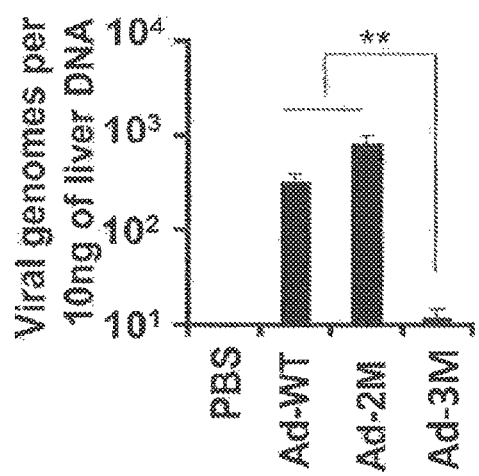
Figure 23C:
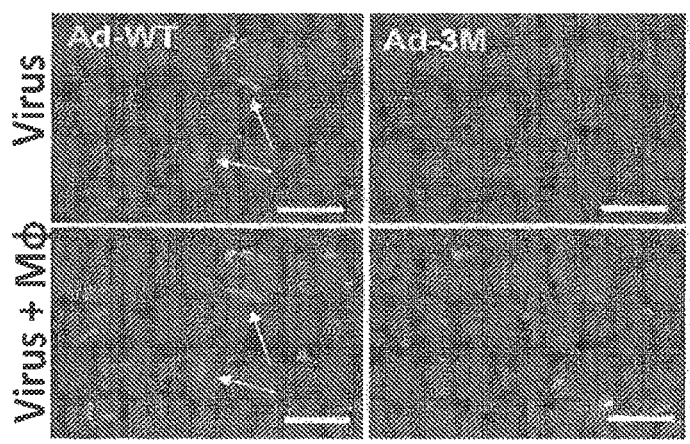
Figure 23D:
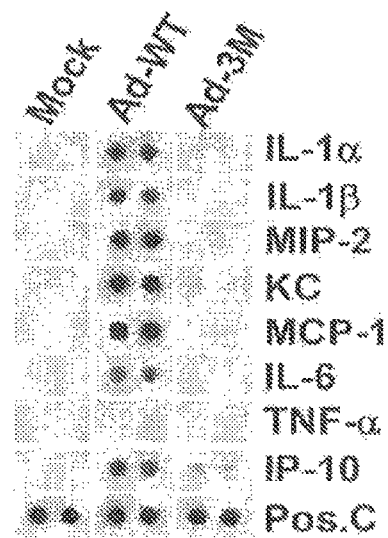
Figure 23E:
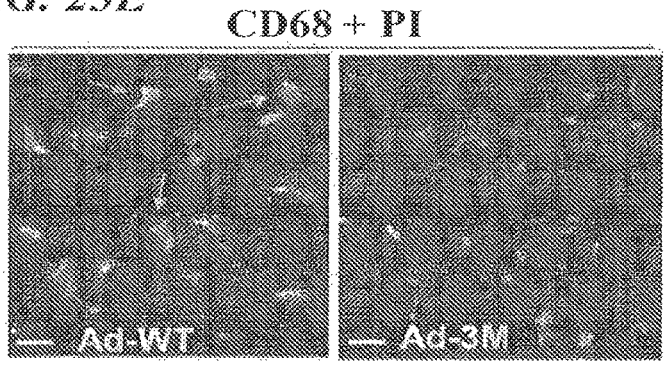

FIGS. 23A, 23B, 23C, 23D, and 23E show that the novel Ad5-based vector, Ad-3M, containing three specific and discrete mutations in capsid proteins, escapes sequestration in the liver and induces greatly attenuated inflammatory response after intravascular injection in mice. FIG. 23A shows the structural localization of mutations in capsid of Ad-3M vector that contains penton RGD-loop substitution for non-RGD containing amino acid sequences derived from human laminin-3 (as shown in FIG. 20), hexon HVR7 point mutation T425A, and HVR1 deletion/substitution (as shown in FIG. 22). FIG. 23B shows the quantitative PCR analysis of the amounts of Ad genomic DNA in the liver 1 hour after intravenous injection of the indicated vectors at a dose of $2 \times 10^{10}$ virus particles per mouse. Ad-WT is Ad5-based vector containing no mutations in the capsid proteins. Ad-2M contains single amino acid substitution in the hexon HVR7, T425A, that abrogates binding of blood coagulation factors and Lam3 substitution within penton RGD loop as shown in FIG. 20. Ad-3M contains three simultaneous mutations in capsid proteins—two mutations identical to Ad-2M and HVR1 deletion/substitution as shown in FIG. 22. Note significant reduction of accumulation of Ad-3M genomic DNA in the liver 1 hour after intravenous virus administration. FIG. 23C shows co-localization of virions of Ad-WT (shown by arrows) and the lack of co-localization of Ad-3M virions with F-4/80-positive Kupffer cells in the liver 1 hour after intravenous virus injection. Virus was stained with anti-hexon Ab. Note that Kupffer cells efficiently accumulate Ad-WT but do not accumulate Ad-3M virus particles. FIG. 23D shows in vivo inflammatory profile of control unmodified Ad-WT vector and Ad-3M vector with three mutations in the capsid, determined by mouse inflammatory antibody array profiling of the spleen 1 h after intravenous injection of $2 \times 10^{10}$ virus particles of indicated vectors. Mock—mice were injected with saline. Note major reduction in the amounts of all pro-inflammatory cytokines and chemokines analyzed observed in the spleens of mice injected with Ad-3M, compared to mice injected with control unmodified Ad-WT (Ad5) vector. N=3. Representative blots are shown. FIG. 23E shows intravenous administration of Ad-3M vector into mice does not trigger necrotic death of Kupffer cells in the liver. Propidium iodide-positive (PI) cells with nuclei are indicated by the arrows. Kupffer cells were determined by staining of liver sections with anti-CD68 macrophage-specific antibodies. Representative fields are shown. Scale bar is 50 μm.

Figure 24:
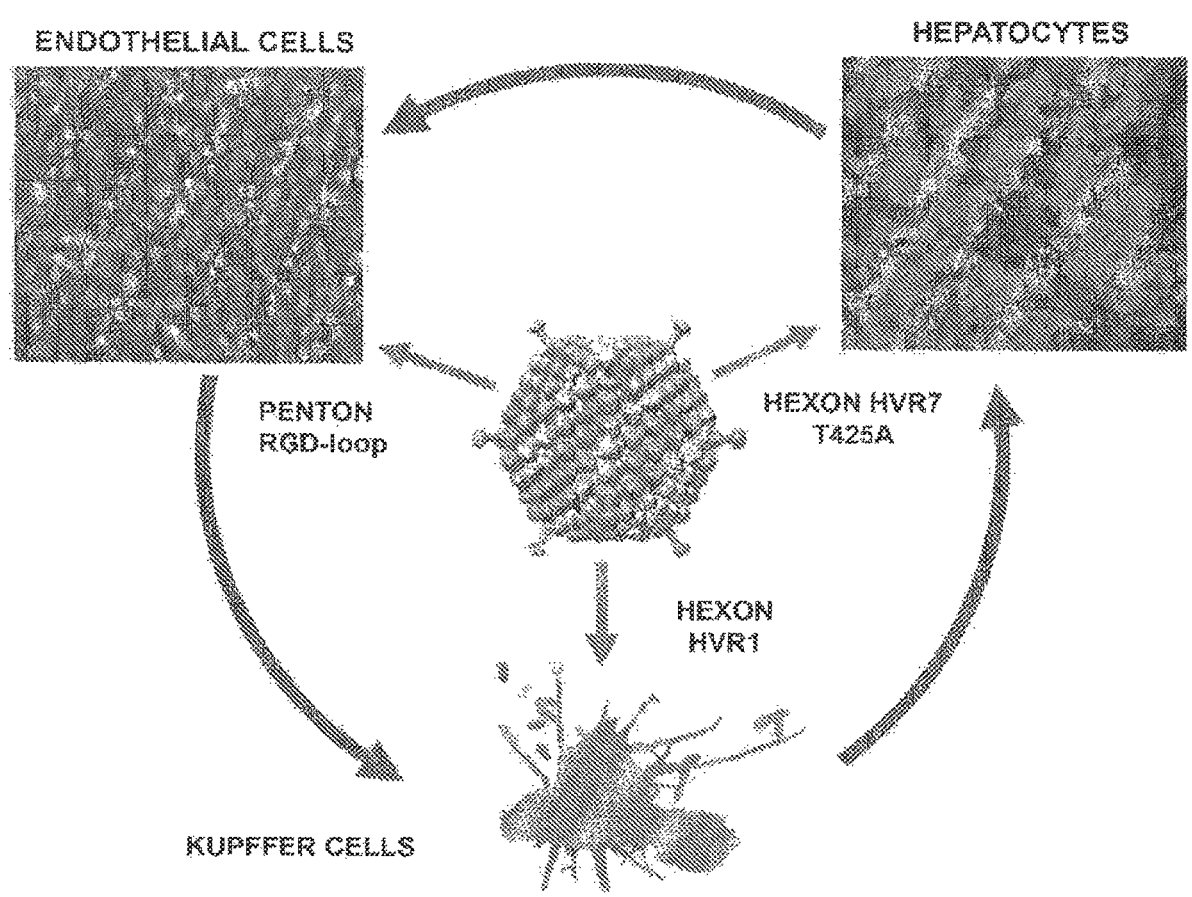

FIG. 24 shows the concept of equifunctional roles of different types of hepatic cells in trapping blood-borne Ads and associated mechanisms and strategies to prevent virus interaction with specific hepatic cells via introduction of mutations into Ad capsid proteins of a single virus, the preferred embodiment of this invention.

FIGS. 25A and 25B show additional examples of mutations introduced into Ad5 penton base RGD motif-containing loop, which modify penton binding to cellular integrins for in vivo virus targeting or de-targeting to host cells. FIG. 25A shows an example of deletion of an RGD-motif-containing loop. FIG. 25B shows an example of a substitution of an RGD motif for non-RGD motif-containing peptides, capable of selectively and iso-functionally to native RGD-containing amino acid sequences, to drive penton interactions with novel receptors in vivo, including but not limited to cellular integrins, present on tumor cells, but not abundantly expressed on the liver cells.

Figure 10A:
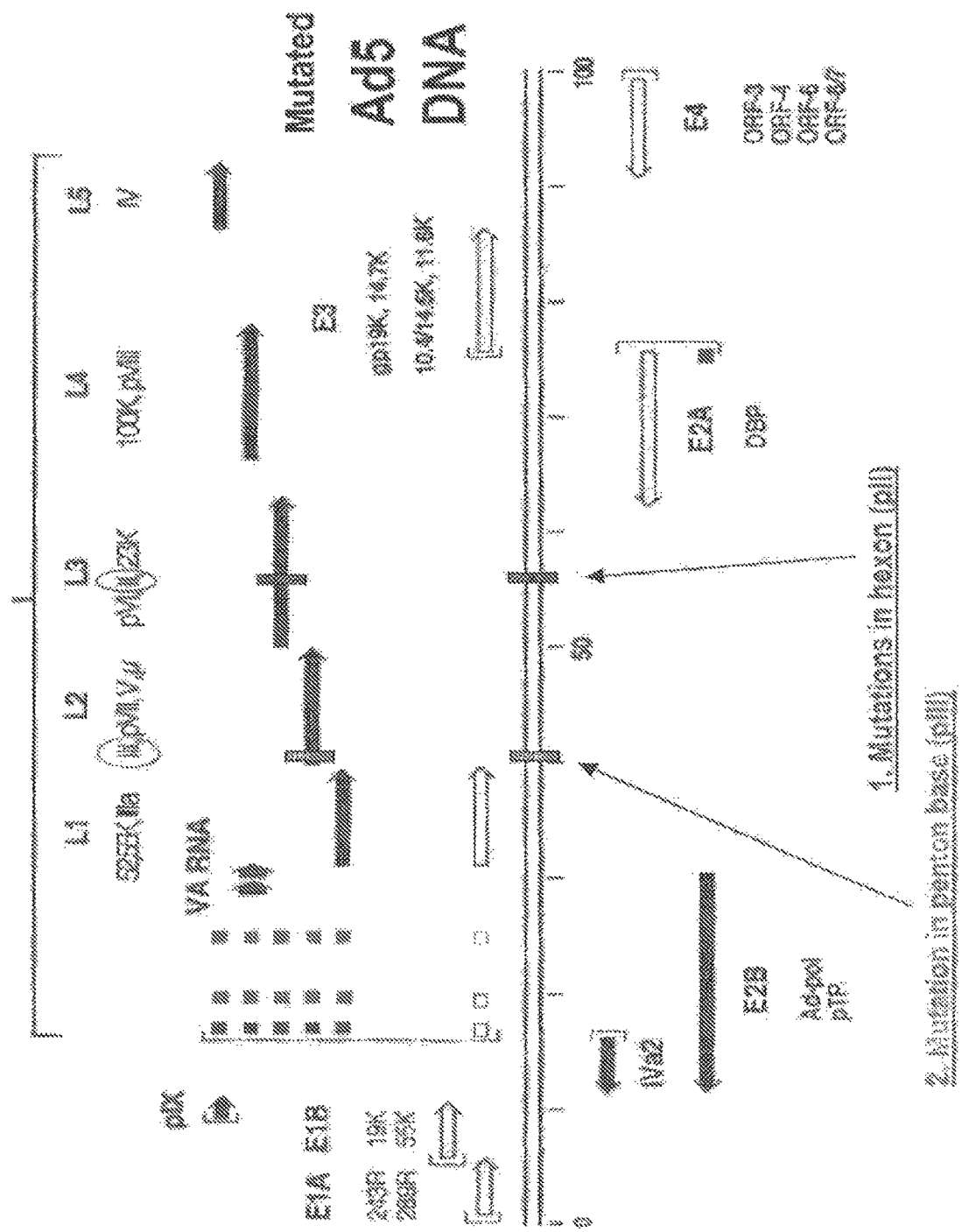
Figure 10B:
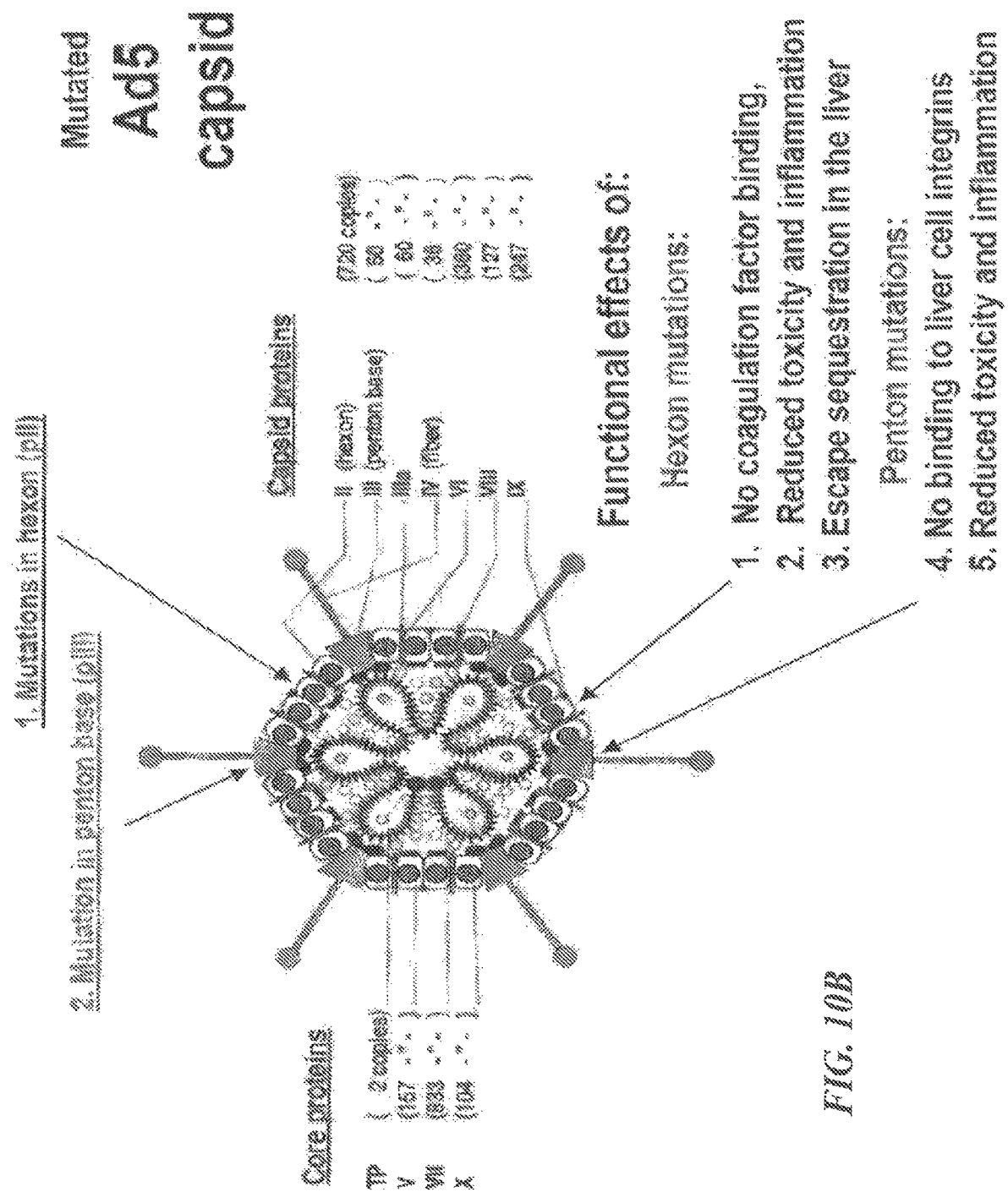
Figure 13A:
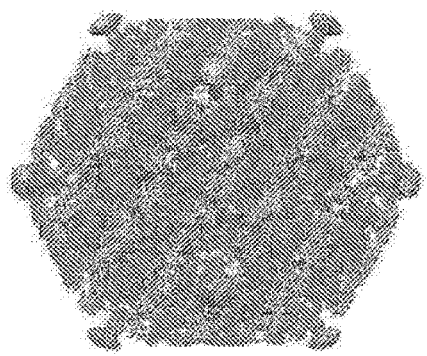
Figure 13B:
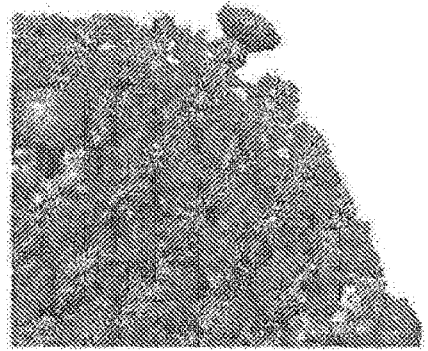
Figure 13C:
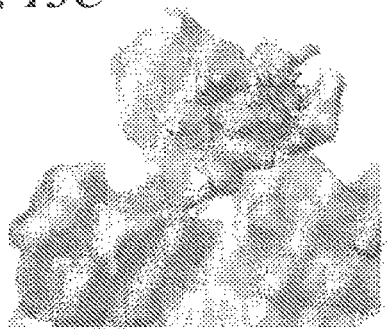
Figure 13D:
Figure 13E:
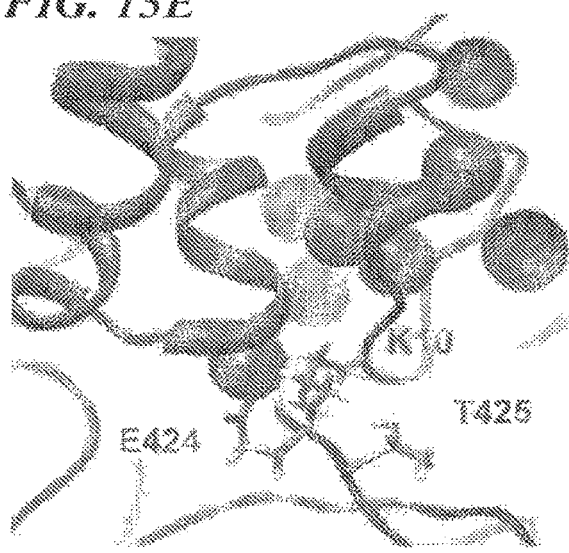
Figure 13F:
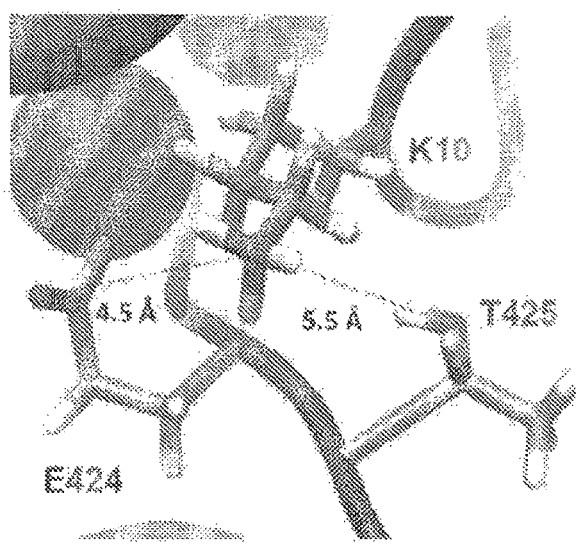
Figure 14A:
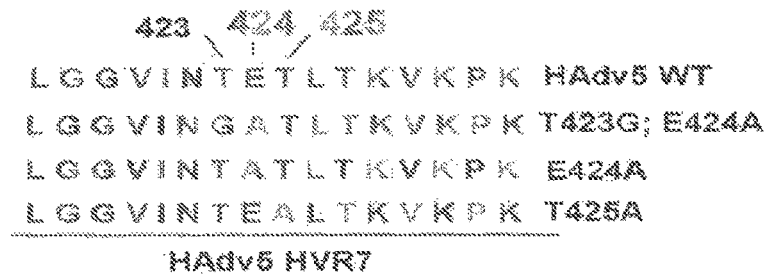
Figure 14B:
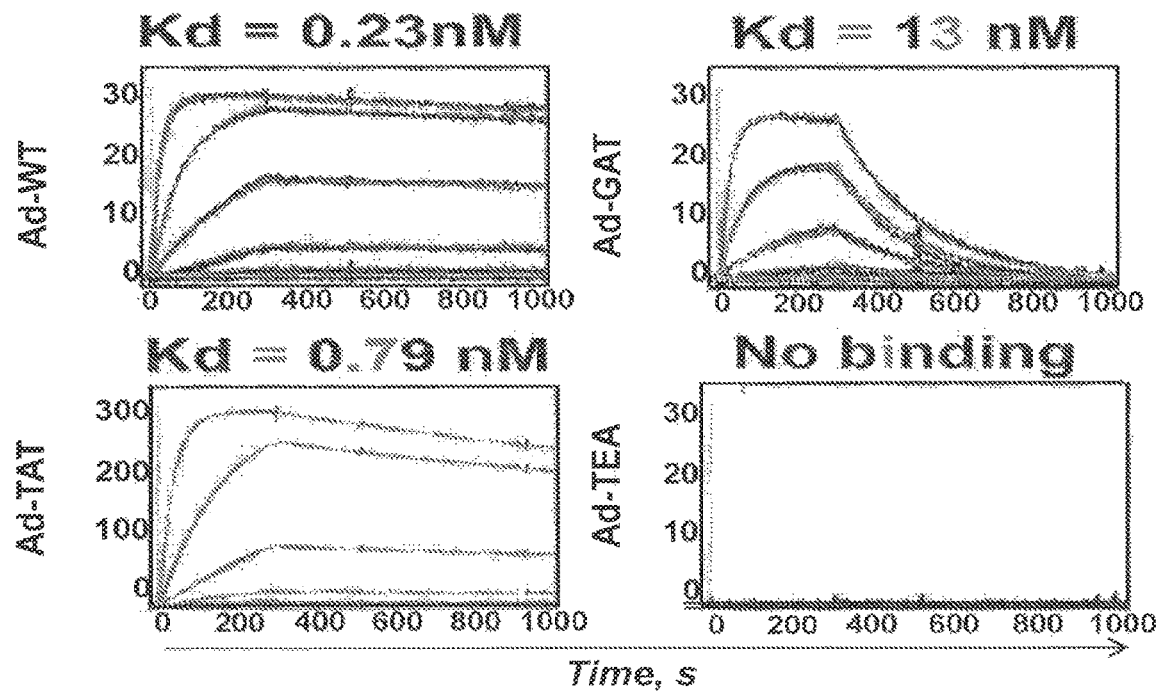
Figure 14C:
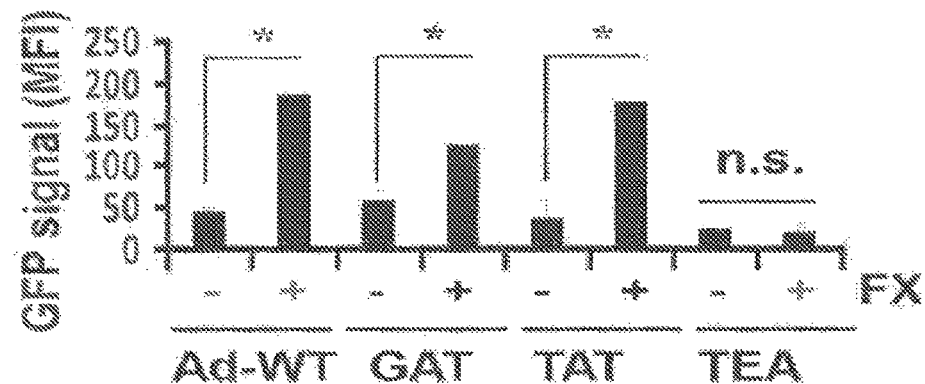
Figure 14D:
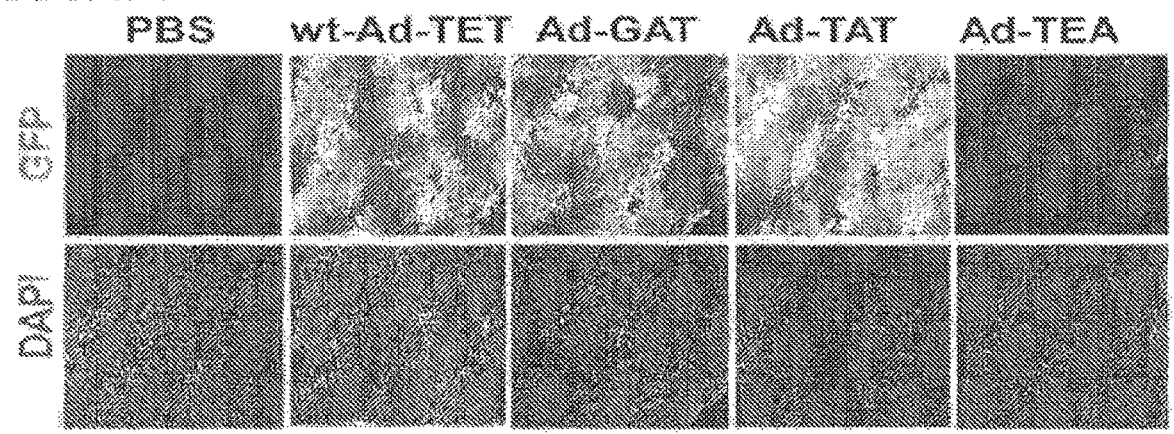
Figure 14E:
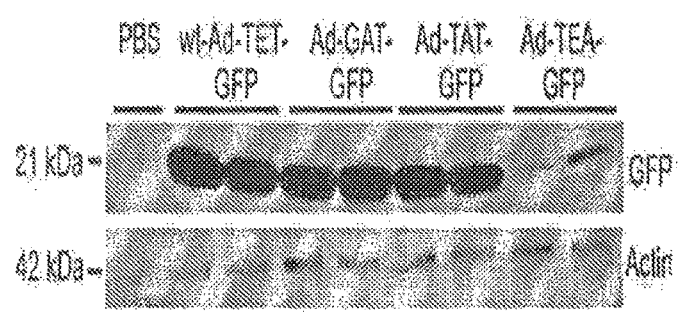
Figure 14F:
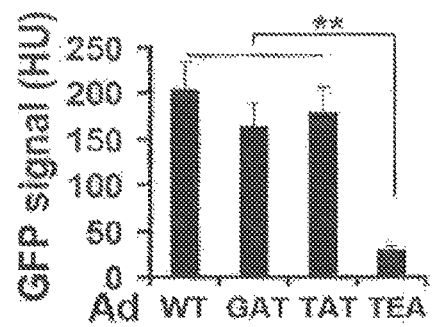
Figure 14G:
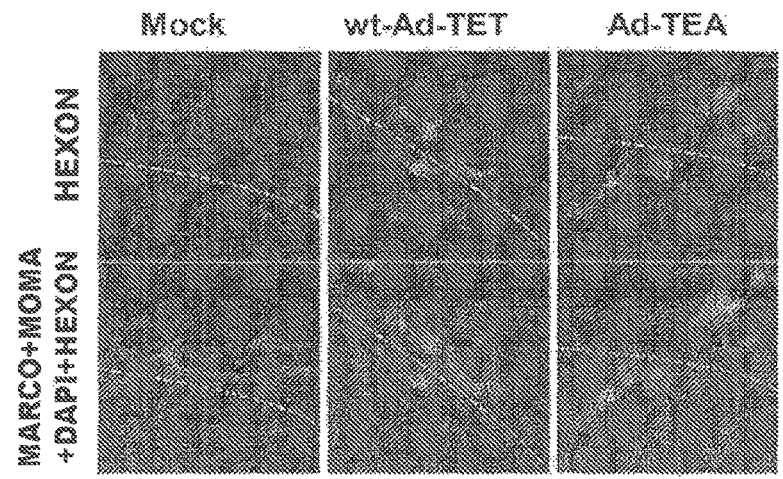
Figure 14H:
Figure 15A:
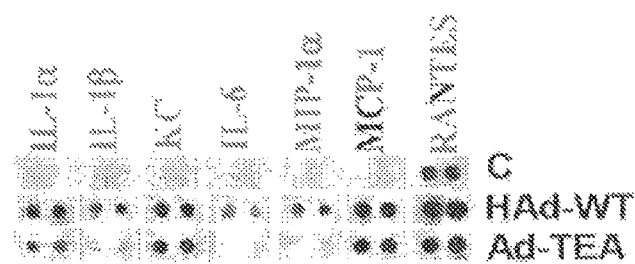
Figure 15B:
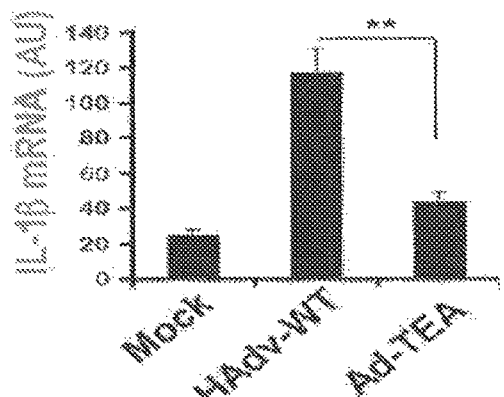
Figure 15C:
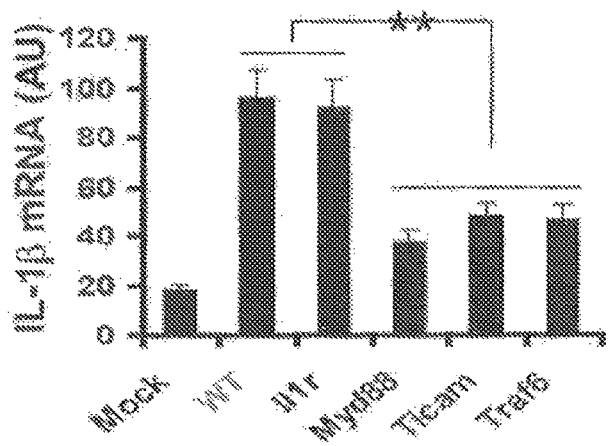
Figure 15D:
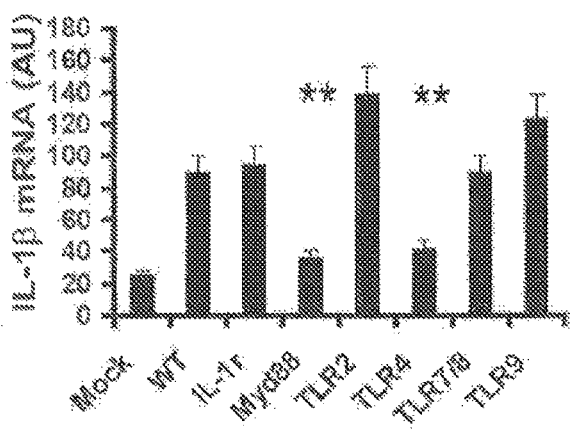
Figure 15E:
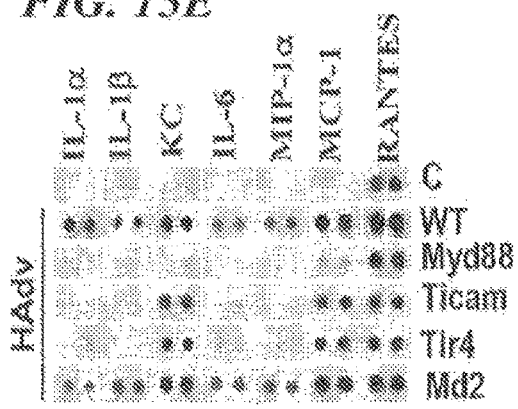
Figure 15F:
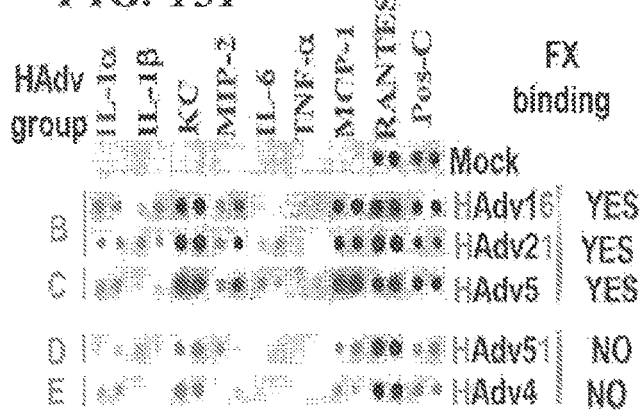
Figure 26:
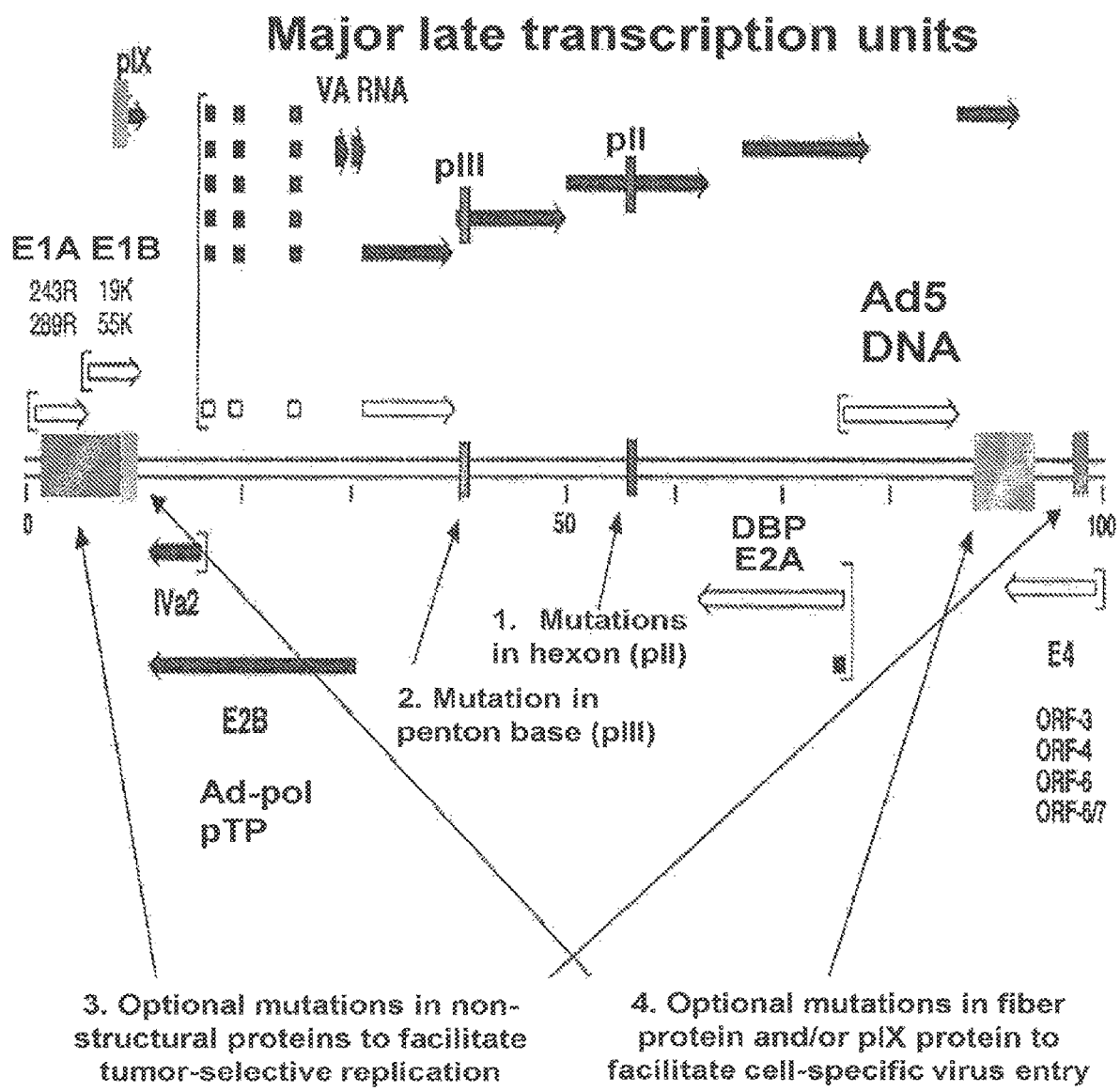

FIG. 26 shows modifications of Ad shown in FIG. 10 allowing it to replicate specifically in tumor cells, or to selectively infect tumor or other cell types and express foreign transgenes with anti-tumor or immune-stimulatory activity, after intravascular administration.

V. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

a. DEFINITIONS

Unless defined otherwise, all technical and scientific terms used herein have the same meaning as commonly understood by one of ordinary skill in the art to which this invention belongs. For purposes of the present invention, the following terms are defined below.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

b. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein.

In one aspect, the present invention provides for novel modified Ad vectors.

i. Adenovirus

Adenovirus (also referred to herein as "Ad") is a ubiquitous pathogen causing a wide range of human diseases, which include respiratory tract infections, conjunctivitis, hemonhagic cystitis, and gastrointestinal diseases (Shenk, 1996, 2001). In immunocompetent patients, Ad infection is self-limited, and after resolution of the acute infection, the virus remains latent in lymphoid and renal tissues. In contrast, in immunocompromized patients Ad may cause life threatening or even fatal fulminant hepatitis and disseminated infection of other tissues (Kojaoghlanian et al., 2003). There are currently 60 characterized human Ad serotypes which are divided into seven species (formally subgroups) from A to G (Alonso-Padilla et al., 2015). Eighty percent pediatric patients develop antibodies to at least one of many Ad serotypes by the age of 5 (Barouch et al., 2011; Bradley et al., 2012; Roberts et al., 2006) The prevalence of human Ad species C-specific antibodies in these populations reaches as high as 50 to 80% (Alonso-Padilla et al., 2015; Barouch et al., 2011). Although various Ad serotypes may initiate infection via different transmission routes, and by utilizing distinct virus attachment receptors, the host factors and cell types controlling tissue specificity of Ad infection in vivo remain insufficiently understood.

The Ad genome is a double-stranded linear DNA molecule of about 36 kilobases containing genes encoding the viral proteins. At the ends of the Ad genome, inverted repeats (also referred to as inverted terminal repeats or ITRs) contain replication and the encapsidation regions. The early genes are distributed in four regions dispersed in the Ad genome (designated El to E4). The early genes are expressed in six transcriptional units. The late genes (designated Li to L5) partly overlap with the early transcription units and are generally transcribed from the major late promoter (referred to as MLP) (Shenk, 2001).

The Ad infectious cycle occurs in two steps. The early phase precedes the initiation of replication and makes it possible to produce the early proteins regulating the replication and transcription of the viral DNA. The replication of the genome is followed by the late phase during which the structural proteins that constitute the viral particles are synthesized. The assembly of the new virions takes place in the host cell nucleus. In a first stage, the viral proteins assemble so as to form empty capsids of icosahedral structure into which the genome is encapsidated. The assembled virus includes a penton base and fiber. The Ads liberated are capable of infecting other permissive cells. The fiber and the penton base present at the surface of the capsids play a role in the cellular attachment of the virions and their internalization.

In vitro studies demonstrated that Ad infection starts with the virus binding to a high affinity primary attachment receptor on the cell surface (Nemerow, 2000). The trimeric Ad fiber protein mediates this interaction when its distal knob domain binds to a specific cellular receptor. For binding to cells, species A, C, D, E, and F human Ad may utilize the coxsackievirus and Ad receptor (CAR) (Roelvink et al., 1998); however, the majority of human species B Ad utilize CD46 as a high affinity cellular attachment receptor (Gaggar et al., 2003). In this regard, soluble Ad fiber or anti-fiber antibodies can inhibit infection by the Ad. Fiber-mediated binding of Ad to cells is followed by RGD motif-mediated binding of the viral penton base protein to cellular integrins (e.g., a433 and 45) (Nemerow and Stewart, 1999). This interaction induces integrin activation and cytoskeleton rearrangement that facilitates internalization of the virus particle into the cell. Based in part on this knowledge, previous disclosure provided Ad vectors that were designed to change Ad interactions with integrins in the in vitro cell culture systems. See, e.g., U.S. Pat. No. 5,712,136, which is incorporated by reference herein. However the patent above does not teach of constructing Ads for in vivo applications, capable of escaping liver sequestration after intravascular administration and triggering reduced inflammatory responses. Importantly, Ads vectors comprising only a mutated penton protein are trapped in the liver tissue at levels identical to the wild type virus and therefore cannot be used for efficient infecting of extra-hepatic cells.

Ads are used in an increasing number of applications for gene transfer. Ads have been identified in numerous animal species. They exhibit low pathogenicity in immune-competent individuals, and replicate in both in dividing and quiescent cells. Ads generally exhibit a broad host spectrum and are capable of infecting a very large number of cell types, such as epithelial cells, endothelial cells, myocytes, hepatocytes, nerve cells, and synoviocytes, among many other cell types.

Recombinant Ad vectors are derived from Ads and usually include cis acting regions that are necessary for the replication of the virus in the infected cell (e.g., the ITRs and encapsidation sequences). Recombinant Ad vectors can also contain substantial internal deletions designed to remove or modify viral genes, to allow for the insertion of a heterologous gene(s) for gene transfer. To accommodate heterologous genes, Ads used in gene transfer protocols can be made deficient for replication by deletion of at least the El region and are propagated in a complementation host cell line that provides the deleted viral function(s) in trans. One commonly used host cell line, the 293 line, was established from human embryonic kidney cells and provides the Ad El function in trans.

Gene delivery systems based on human species C Ad serotype 5 (Ad5) are among the most frequently used in clinical studies, which aim to correct human genetic and acquired diseases, including cancer. The extreme propensity of the virus for hepatocyte infection following its intravascular delivery has made Ad5 the vector of choice for applications requiring high level transgene expression in hepatocytes in vivo. However, the efficient interaction between Ad5 and liver cells, which sequester over 90% of the delivered vector dose (Alemany and Curiel, 2001; Alemany et al., 2000; Worgall et al., 1997), represents a significant hindrance if gene delivery to extra-hepatic cells and tissues, such as disseminated metastatic cancer cells and tissues, is required. From in vitro analyses it was found that Ad5 infection is initiated when the minor capsid protein, fiber, binds to CAR on the cell surface (Bergelson et al., 1997). Subsequent binding of the penton base protein to cellular integrins facilitates internalization of the attached particle into the cell (Wickham et al., 1993). Although both CAR and integrin binding are important for cell infection in vitro, neither of these interactions are essential for Ad5 entry into hepatocytes in vivo (Alemany and Curiel, 2001; Shayakhmetov et al., 2004).

Ad sequestration in liver resident macrophages, Kuppffer cells (Lieber et al., 1997), and macrophages residing in other organs of the body, such as spleen (Di Paolo et al., 2009a), leads to activation of inflammatory cytokines and chemokines, induction of pro-inflammatory-type of cell death (Manickan et al., 2006), rapid release on polymorphonuclear leukocytes from the bone marrow into the blood (Di Paolo N C, 2014) and systemic toxicity manifested by elevated levels of pro-inflammatory mediators in the blood, systemic complement activation, followed by leukocytopenia. Acute systemic inflammatory response associated with intravenous administration of Ad represents the key barrier for escalating Ad doses to a level that is therapeutic in gene transfer applications or transduction of metastatic tumors.

The transduction of hepatocytes and the sequestration of Ad virions in the liver tissue after intravascular virus injection are governed by distinct molecular mechanisms. The liver residential macrophages, Kupffer cells, were thought to play the dominant role amongst factors contributing to the sequestration of blood-born Ad virions in the liver. Indeed, when Ad is injected into mice intravenously, Kupffer cells rapidly accumulate large amounts of virus particles (Di Paolo et al., 2009b). Moreover, elimination of Kupffer cells from the liver after treatment of mice with ether clodronate liposomes or gadolinium chloride results in a marked increase in the levels of hepatocyte-specific Ad-mediated gene transfer (Wolff et al., 1997; Worgall et al., 1997), suggesting that significant amounts of infectious virus particles can be trapped by Kupffer cells.

Binding of blood coagulation factor X to Ad5 hexon leads to efficient hepatocyte transduction (Kalyuzhniy et al., 2008; Waddington et al., 2008). However, the sequestration in the liver of Ad5 hexon mutant, which was unable to bind coagulation factors and transduce hepatocytes, was relatively unchanged compared to control unmodified vectors (Kalyuzhniy et al., 2008).

This invention provides for novel genetically-modified Ad vectors that contain mutations, which simultaneously structurally and functionally diminish or abrogate specific virus interactions with liver cells in a host in vivo and also demonstrate greatly attenuated systemic toxicity and inflammation. One example comprises capsid-modified Ad vectors, wherein a hexon gene is mutated such that Ad interaction with blood factors, including vitamin K-dependent blood coagulation factors, is abrogated. In another example, a capsid-modified Ad vector comprises a mutated penton gene, such that the Ad interaction in vivo with classes of natural Ad-interacting cellular integrins is diminished or reduced. In another example, the hexon and penton mutations are combined in one vector, leading to the production of the vector suitable for intravascular administration and demonstrating greatly attenuated systemic toxicity and inflammation.

The best mode to carry the invention and as an ultimate and preferred example of embodiment of the novel vector, in addition to mutations in the penton and within the coagulation factor-binding site in the hexon, a third mutation is introduced in the hexon surface-exposed hyper-variable loop 1 (HVR1) that ablates virus interaction with Kupffer cells, resulting in generation of the vector containing three mutations simultaneously. This novel vector, possessing three mutations simultaneously (one in penton and two in hexon hyper variable loops to ablate coagulation factor binding and to prevent virus sequestration in Kupffer cells), escapes sequestration in the liver tissue and demonstrates greatly attenuated systemic toxicity after intravascular administration.

In addition to mutations in hexon and/or penton genes as described above, the Ad vectors described herein can comprise mutations in a gene that encodes for the fiber protein, protein IX, and/or other structural or non-structural proteins.

Further, the hexon and/or penton mutations can be employed along with administration of one or more substances that further reduce Ad targeting and sequestration in the liver of the host. In one example, warfarin can be used to reduce the interaction of blood cells and blood coagulation factors with the Ad vectors. In another example, the host can be clodronate liposome-treated such that Kupffer cells are killed and eliminated from the liver.

Additionally, the Ad vectors, as described herein, can carry one or more transgenes that, for example, exhibit anti-tumor, tumor-suppressor, and/or immune-stimulatory activities or one or more genetic mutations, which enable tumor-selective virus replication. Further, the recombinant Ads as described herein provide a novel design of functionally-distinct and defined sets of mutations, which enable the virus of escaping interaction with host proteins and factors and thereby avoid trapping of the virus in the liver after intravascular delivery.

Ads vectors based on non-Ad5 human serotypes or animal serotypes exhibit differential ability to interact with host proteins and factors, including but not limited to vitamin K-dependent blood coagulation factors, after intravascular administration (Kalyuzhniy et al., 2008). This disclosure and the molecular mechanisms and functional interactions described here in, provide rationale and methods for modification of non-human Ad5-based vectors to allow their escape from being sequestered in the liver after intravascular delivery. If the non-Ad5-based vector is naturally unable to interact with vitamin K-dependent blood coagulation factors (such as human Ad serotypes Ad9, Ad50, Ad26, Ad48, Ad51 (FIG. 12D, continued)), then their trapping in the liver after intravascular administration can be prevented via mutations in the penton and/or Kupffer-cell-targeting hexon hyper-variable loops (HVRs). When the non-Ad5-based vector naturally unable to interact with both, the blood factors and Kupffer cells due to natural variation in amino acid sequence of hexon HVRs, the introduction of mutation in penton only is sufficient to allow the virus to escape from the liver sequestration after intravascular administration.

The modified Ad vectors, as described herein, can be employed in one or more methods. In one such method, one or more of the Ad vectors are employed in a method for delivering a transgene or being designed as replicating oncolytic virus targeted to a non-liver cell or both, wherein the target cell can be present within the body of the host. One or more of the Ad vectors can be employed in a method of administering an Ad such that the Ad virions evade sequestration in a host's liver. Such liver detargeted replicating or non-replicating Ad vectors can be useful for use in delivering one or more predetermined transgenes to non-hepatic cells within the body of the host, wherein the transgene is configured to correct a genetic, biochemical, or physiological defect in the host cell or host body or they can be used for eliminating localized or metastatic cancer or treat both solid or hematologic malignancies.

As noted above, the present invention provides for novel modified Ad vectors for the generation and use of Ad vectors comprising modified hexon and/or penton capsid proteins, where the modifications are made to avoid the trapping of Ad in the liver after intravenous virus administration. Additionally, the Ad vectors described herein can comprise genetic mutations in virus-encoded structural and non-structural proteins to enable tumor cell-specific infection and replication of the virus.

In particular, the present invention provides for a recombinant, double-stranded, Ad vector where the single virus genomic DNA molecule comprising genetic mutations in a hexon gene and/or a penton gene. The first type of hexon mutations are configured to reduce or ablate virus interaction with blood coagulation factors, including coagulation factors (F) FX, FIX, FVII, Protein C and Protein S. The second type of hexon mutations are confined to reduce or ablate virus interaction with Kupffer cells, either directly or indirectly, when the virus is administered or reaches into the bloodstream and, therefore, can be present in a complex with blood proteins, other than coagulation factors. The penton mutations are configured to reduce or ablate Ad interactions with cellular integrins, in particular of β3 class. A schematic configuration of one example of a recombinant Ad vector having described mutations in both hexon and penton and their functional significance is depicted in FIG. 10 and FIG. 23A.

Figure 11A:
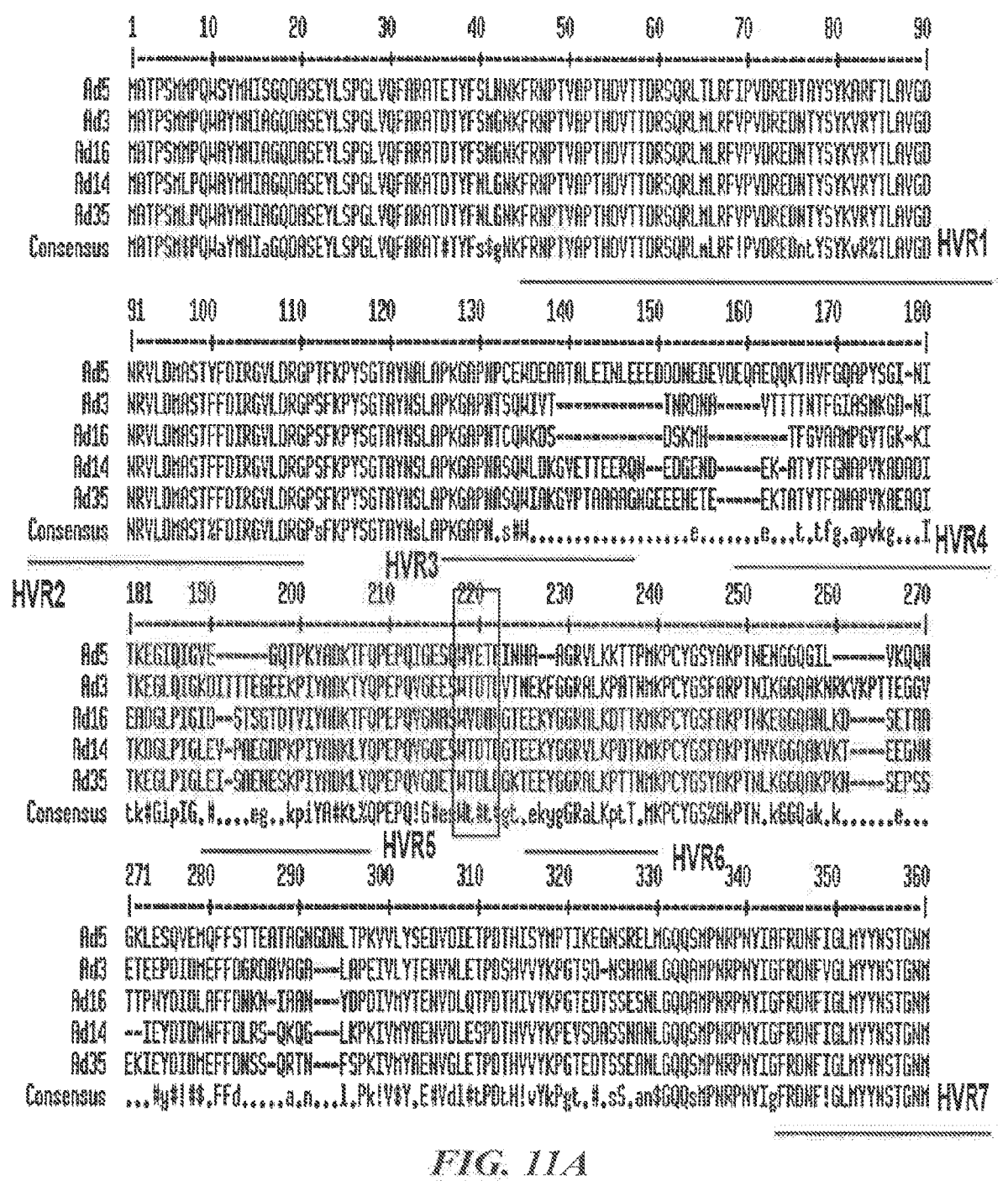

In addition to the above identified mutations, the Ads of the invention may further comprise additional mutations. Specific mutations ablating hexon interaction with blood coagulation factors, include mutation, deletion, or substitution of amino acids TET within human Ad5 hexon hypervariable region (HVR) 7 (FIGS. 11, 12). For human Ad5 serotype, a single amino acid substitution T425A in hexon HVR7 is sufficient to ablate interaction of the virus with blood coagulation factor X (FIGS. 13, 14) (Doronin et al., 2012). For other human and animal Ad serotypes, coagulation blood factor-ablating mutation can be introduced into either HVR3 or HVR7 (FIG. 12), depending on where the favorable amino acid sequence for coagulation factor binding is located (Kalyuzhniy et al., 2008). The Ad vector hexon sequence can be a hybrid and can comprise fragments of diverse origins. In certain embodiments, the hexon gene is derived from a human Ad, such as those of serotype C and, in particular, the type 2 or 5 Ads (Ad2 or Ad5). Thus, for example, described herein are Ads, wherein the Ad further comprises a mutation in the HVR3, HVR5, or HVR7 region of the hexon protein, wherein the mutation causes reduced binding of a vitamin K dependent clotting factor.

Specific mutations ablating hexon interaction with Kupffer cells include mutation, deletion, or substitution of amino acids comprising Ad5 HVR1 including but not limited to amino acid sequence shown in FIG. 22. For example, the Ads of the invention described herein are Ads further comprising a mutation in the HVR1 region of the hexon protein, wherein the mutation causes reduced virus interaction with Kupffer cells in the liver.

As noted above, the term "mutation" refers to a substitution, deletion, and/or insertion of one or more residues in the Ad hexon protein. The mutation of blood factor protein binding site can reduce the affinity or avidity of the hexon for the blood factor protein by a factor of about 10, of about 100, of about 1000, of about 10,000, or about 100,000, or of about 1,000,000, or more. In certain embodiments, the blood factor protein binding site is ablated, meaning that no biologically significant blood factor protein binding is retained.

In the context of hexon mutation to avoid virus interaction with Kupffer cells, the mutation comprises a substitution, deletion, and/or insertion of one or more residues in the Ad hexon protein in such a manner, that the virus accumulation in Kupffer cells is reduced or abrogated. When such a hexon mutation is combined in a single virus with mutations ablating blood coagulation factor binding and penton mutation preventing virus interaction with RGD-motif-binging integrins, the resultant virus escapes sequestration in the liver tissue after intravascular administration and induces little or no acute inflammatory response (FIG. 23). The Ad vector hexon sequence can be a hybrid and can comprise fragments of diverse origins, and can comprise naturally-occurring or non-naturally-occurring sequences. In certain embodiments, the hexon gene is derived from a human Ad, such as those of serotype C and, in particular, the type 2 or 5 Ads (Ad2 or Ad5).

Figure 17:
FIG. 17 shows an example of a mutation introduced into Ad5 penton base RGD motif-containing loop, which ablates penton binding to cellular integrins. An example of deletion of RGD tri-amino acid motif from the RGD-loop.

In one aspect present invention provides for penton-modified Ads having Ad penton protein mutated in the regions involved in binding the β3 and β5 class of integrins. Such mutations can include deletion, or substitution of an RGD motif containing penton base loop (FIGS. 17, 20, 25) such that penton protein interactions with cellular integrins in vivo, in particular of the β3 and β5 class, are reduced or eliminated. In other words, the one embodiment of the invention described herein are isolated Ads with a mutation in the RGD motif of the penton protein, wherein the mutation causes reduced binding of $β_3$ integrins of a host cell in vivo. In this context, the term "mutation" refers to a substitution, deletion, and/or insertion of one or more residues in the Ad penton protein. The mutation of integrin binding site can reduce the affinity or avidity of the penton for the integrin protein by a factor of about 10, of about 100, of about 1000, of about 10,000, or about 100,000, or of about 1,000,000, or more. In certain embodiments, the integrin protein binding site is ablated, meaning that no biologically significant integrin protein binding is retained. In one aspect, described herein are Ads wherein the RGD amino acid motif of penton loop is substituted for non-RGD motif-containing peptide, capable of binding to non-β3 cellular integrins in vivo. Also disclosed are Ads wherein the RGD amino acid motif of penton loop is substituted for non-RGD motif-containing peptide, capable of binding to plasma-membrane receptors of non-integrin class in vivo. The Ad vector penton sequence can be a hybrid and can comprise fragments of diverse origins, and can comprise naturally-occurring or non-naturally-occurring sequences. In certain embodiments, the penton gene is derived from a human Ad, such as those of serotype C and, in particular, the type 2 or 5 Ads (Ad2 or Ad5). Thus, in one aspect described herein are Ads wherein the Ad is a species C Ad and/or the Ad serotype is type 5 or 2.

Figure 9:
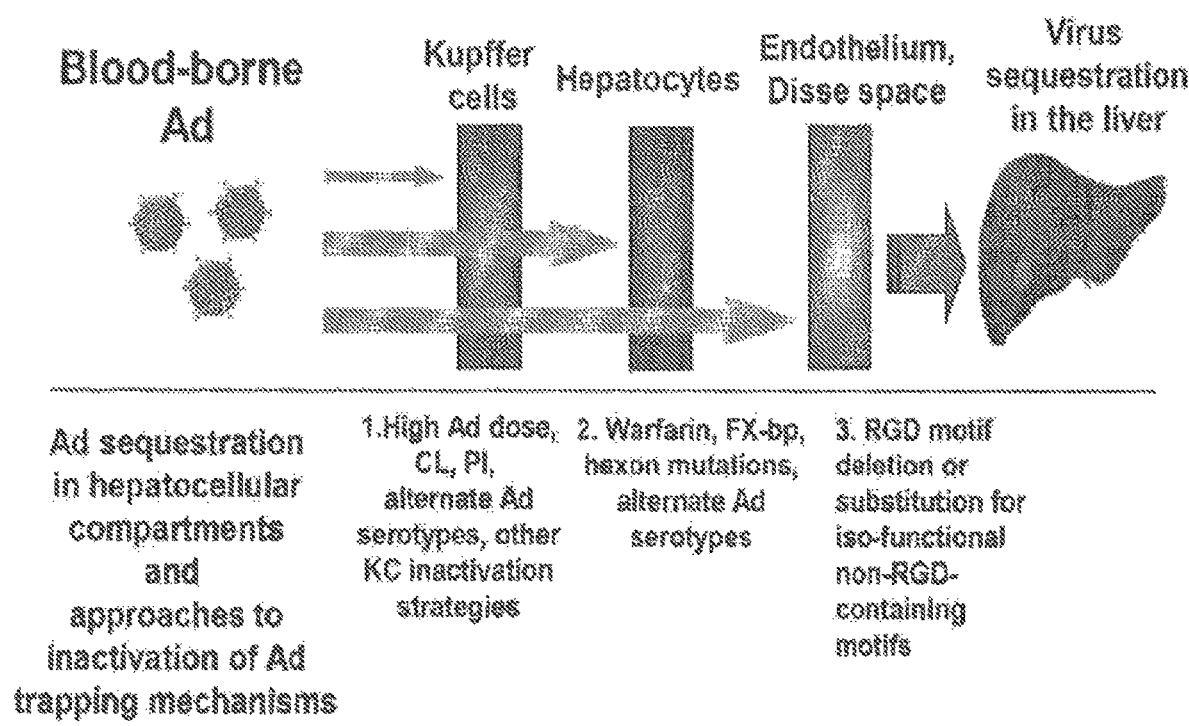
Figure 16:
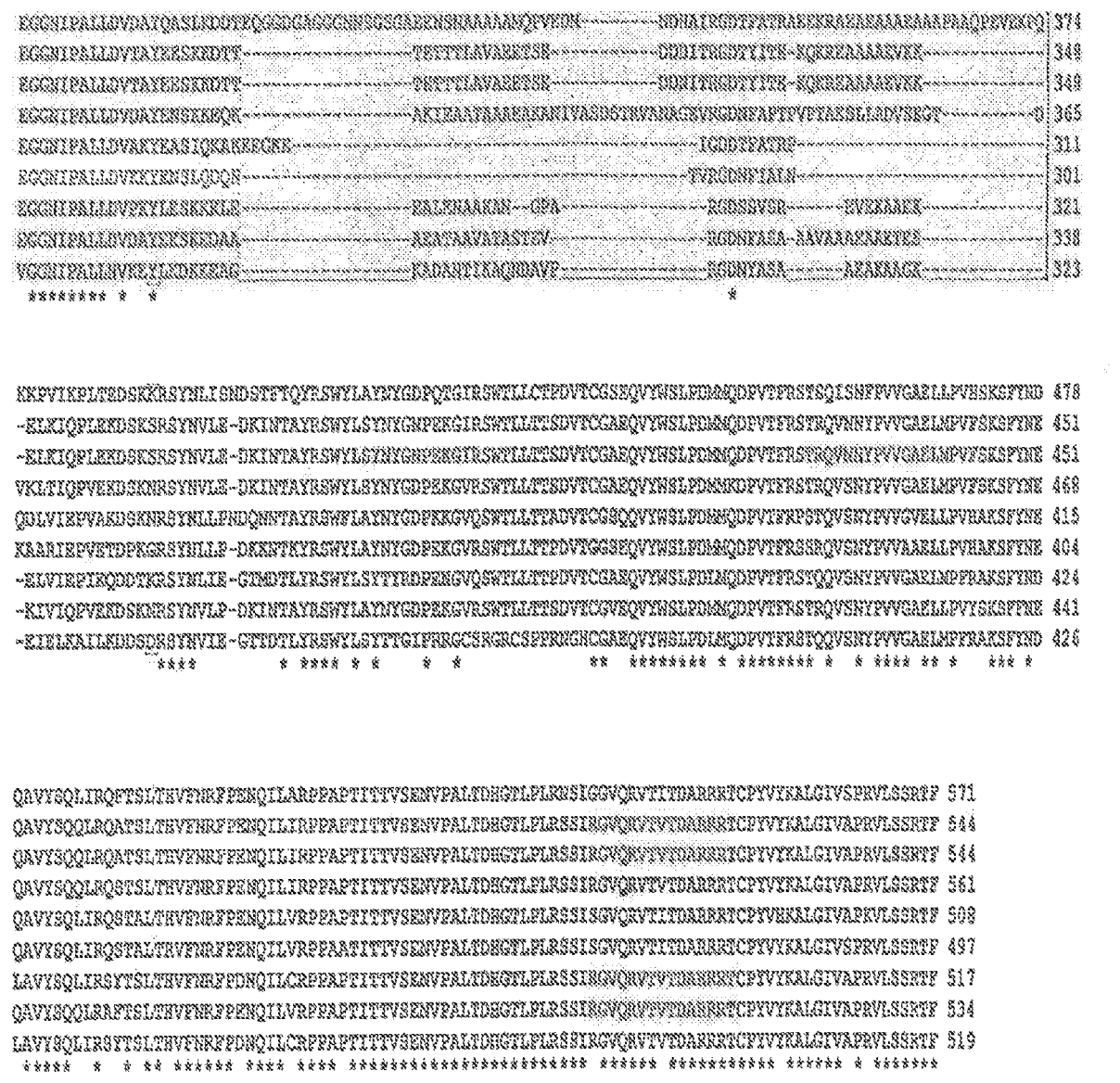

As noted above, the Ad vectors described herein can be based on human Ad serotype 5 (Ad5); however the Ad vectors can be based on any other human or animal Ad serotype. For example, non-human Ads can include canine, avian, bovine, murine, ovine, porcine or simian origin. If alternative to Ad5 serotypes are used for gene therapy after intravascular administration, the functional-inactivating mutation of only one of two proteins (either hexon or penton) can be necessary and sufficient to prevent virus trapping in the liver after intravascular injection, depending on the ability of non-Ad5 hexon to bind coagulation factors, interact with Kupffer cells, or non-Ad5 penton to bind cellular integrins (FIGS. 9, 24). For instance Ad serotype-9 (Ad9) hexon does not bind coagulation factors due to the lack of FX-binding motif in its hexon protein (FIG. 12D, continued). Therefore, to ablate Ad9 trapping in the liver, introduction of hexon mutation in HVR1 and penton mutation to ablate its binding to integrins can be carried out. Ad serotype-41 (Ad41) does not bind RGD motif interacting cellular integrins due to the lack of an RGD motif (FIG. 16). Therefore, introduction of mutation in FX-binding motif and HVR1 in the hexon can be carried out to prevent virus trapping in the liver.

Further, the Ad described herein can comprise additional mutations within its minor capsid proteins, including but not limited to fiber and/or pIX, to enable cell-type-specific virus targeting. The Ad described herein can further comprise genetic mutations in virus-encoded non-structural proteins to enable its tumor cell-specific replication. The fiber/pIX protein and/or non-structural protein mutations can be combined with hexon and/or penton mutations, such that a single Ad vector possess one or more mutations in each of genes that code for the hexon, penton, fiber, pIX, and non-structural proteins (as illustrated in FIG. 26).

"Tumor specific gene expression" and tumor specific" is intended to encompass vector gene expression in a tumor cell but it is understood that vector gene expression in normal cell may also occur, albeit at low levels, which may be considered negligible and background.

TABLE 1

Affinity of FX binding to different viruses.

| Virus | immobilized RU | Kd, nM |
|---|---|---|
| Adenovirus | | |
| Ad5 | 384 | 0.229 |
| Ad16 | 470 | 1.67 |
| Ad2 | 352 | 52.9 |
| Ad21 | 615 | 410 |
| Ad41 | 347 | 630 |
| Ad4 | 2900 | 2480 |
| Ad3 | 2973 | 3000 |
| Ad35 | 315 | No binding |
| Ad51 | 667 | No binding |
| Ad9 | 311 | No binding |
| Ad50 | 256 | No binding |
| Reovirus | | |
| T3D | 486 | No binding |
| Ad5-sCAR* | | 7.9 |
| Ad9-sCAR* | | 6400 |
| Ad12-sCAR* | | 15 |
| Ad41L-sCAR* | | 7.3 |

Figure 7A:
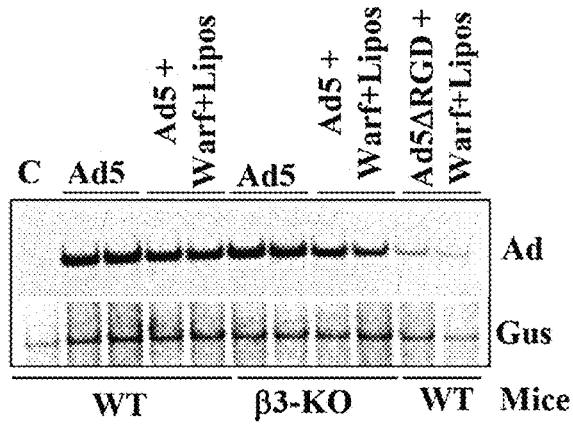
Figure 7B:
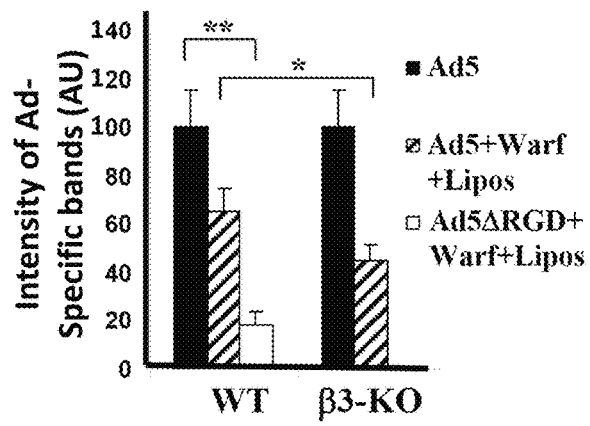
Figure 7C:
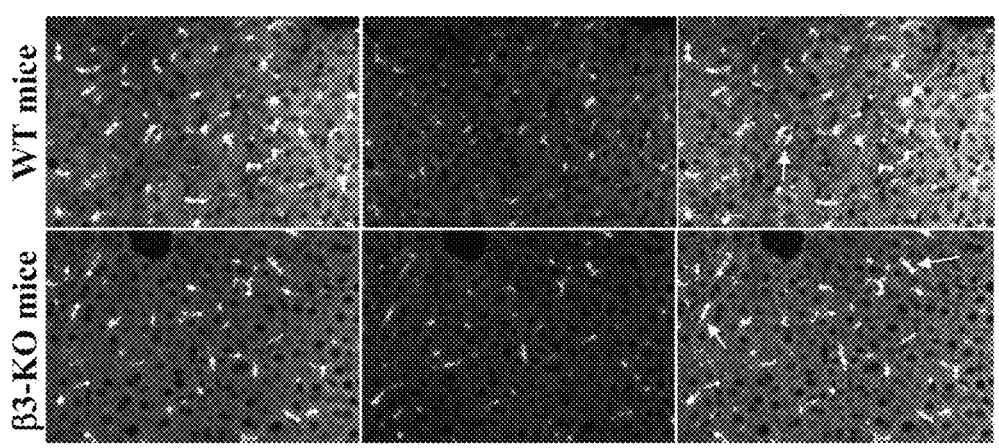
Figure 7D:
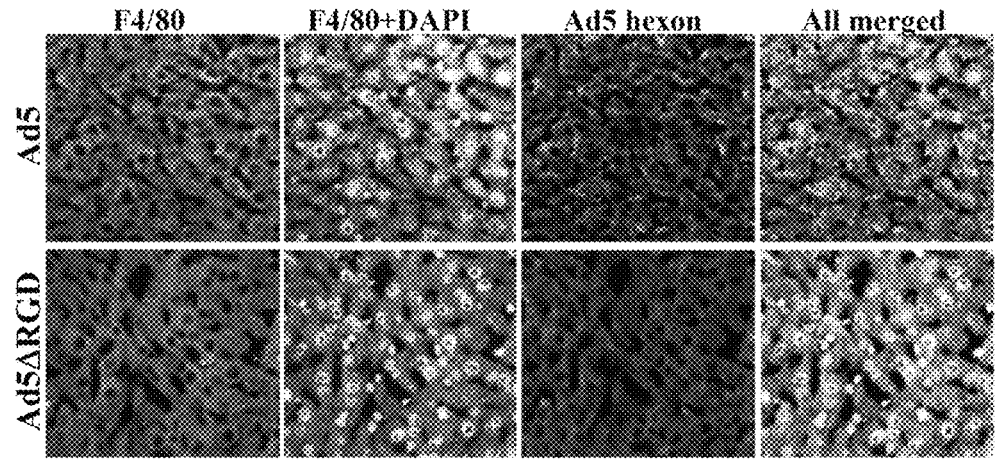

The Ad vectors, as described herein, can be administered to a mammal intravenously after pharmacological conditioning of the host to at least partially inhibit host mechanisms for trapping virus in the liver. For example, association of modified Ad virions with liver sinusoids can be reduced below a threshold for detection after injection of warfarin- and clodronate liposome-treated mammals with a penton-mutated Ad (FIG. 7D). Warfarin can reduce the interaction of hexon proteins with blood factors, and clodronate liposome treatment can at least partially inhibit virus sequestration within Kupffer cells. Ad virion sequestration within Kupffer cells may occur via mechanisms unrelated to blood coagulation factors and/or cellular integrins. In some embodiments, one or more predetermined hexon protein mutations can be used to abrogate Ad virion binding and transduction of blood cells, rather than employing a pharmacological intervention, such as warfarin.

Figure 2A:
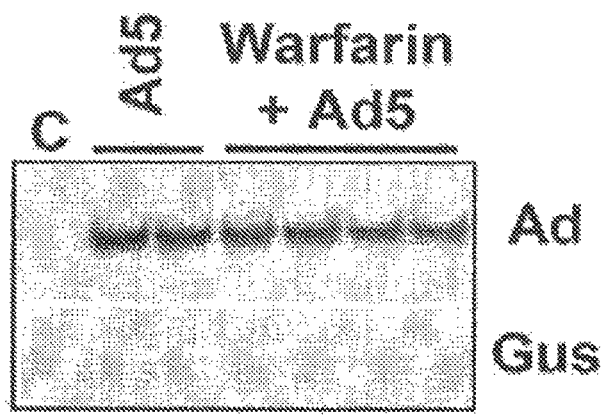
Figure 3A:
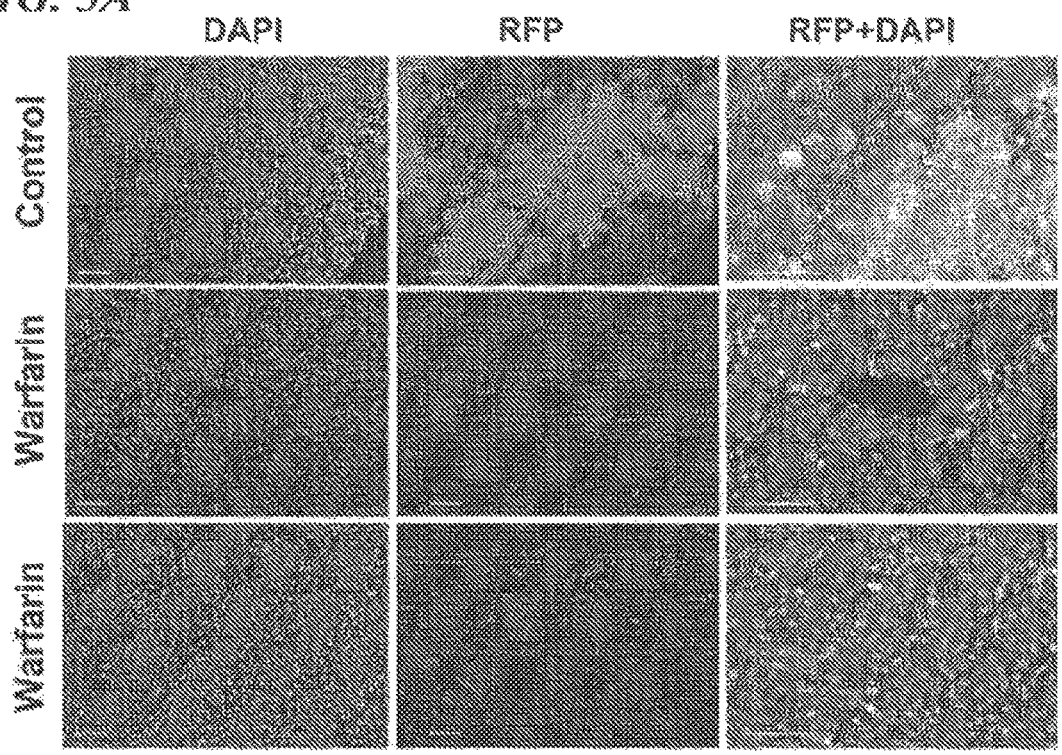
Figure 3B:
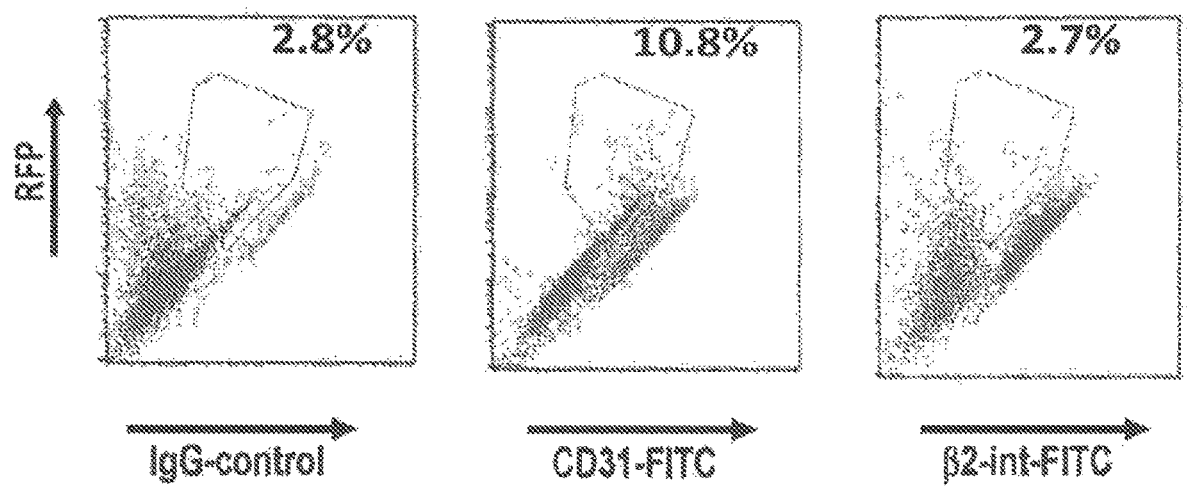
Figure 4A:
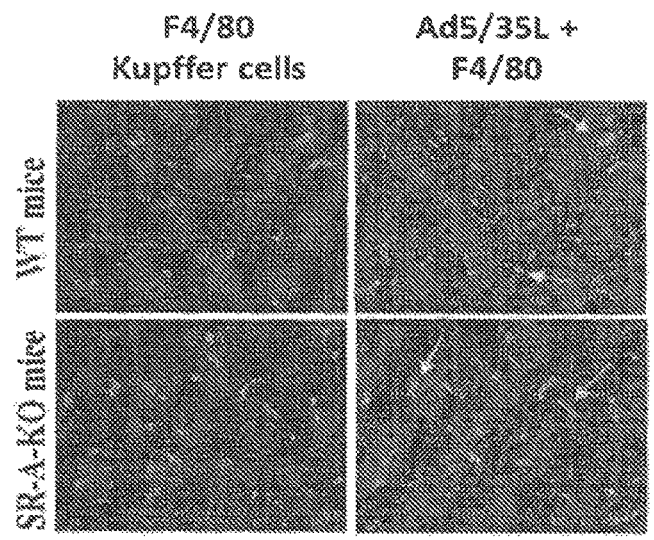
Figure 4B:
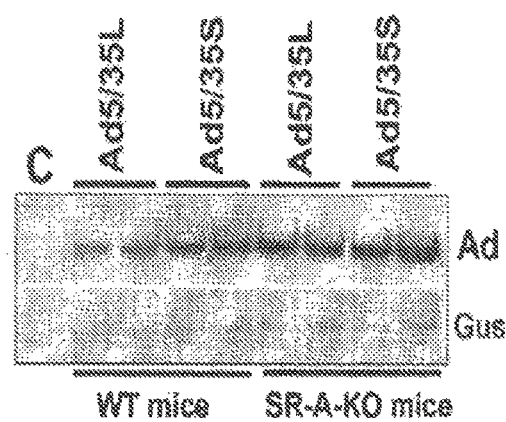
Figure 4C:
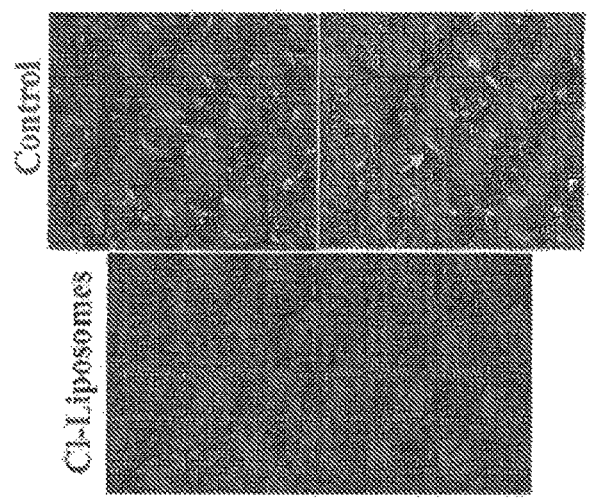
Figure 4D:
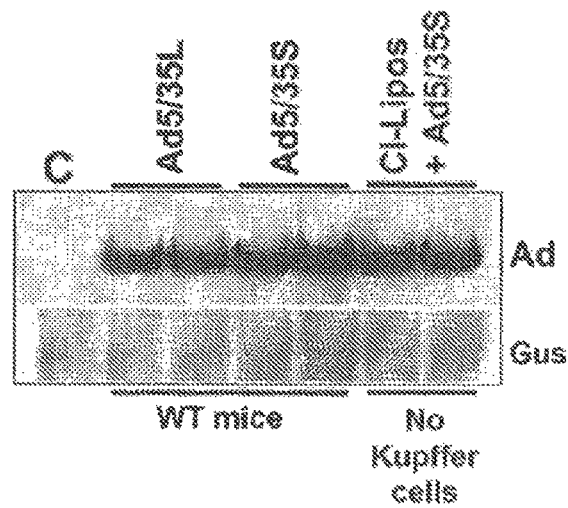
Figure 5A:
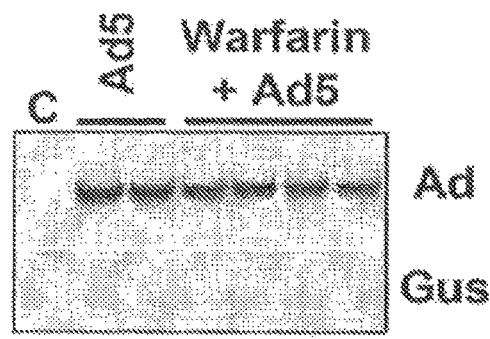
Figure 5B:
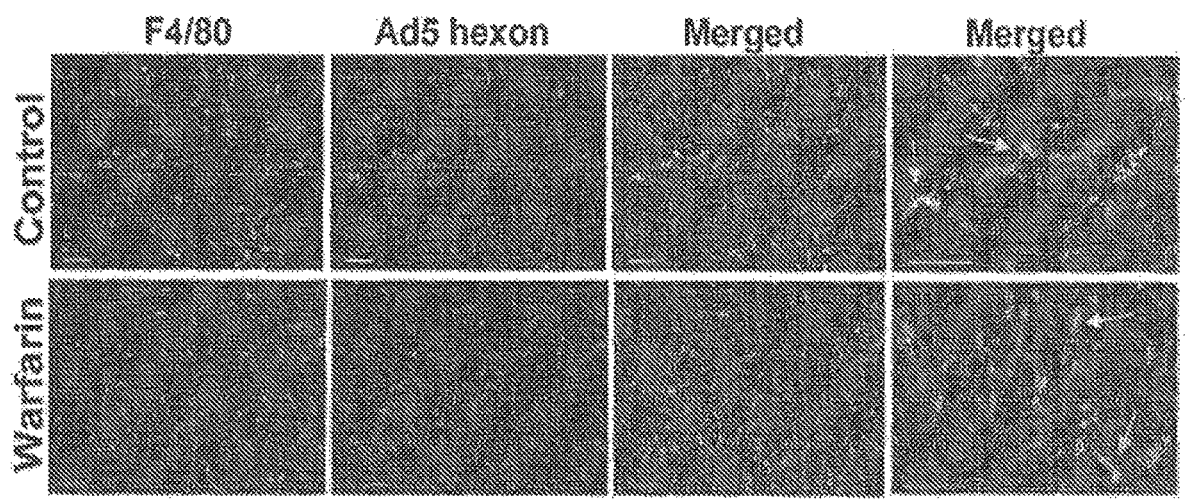

Herein, the contribution of each of the known mechanisms in mediating the sequestration of blood-born Ad virions in the liver was systematically analyzed. The data indicates that specific elimination of Kupffer cells with clodronate liposomes or inactivation of blood-factor pathway with warfarin independently does not result in a measurable reduction of Ad DNA levels trapped in the liver after intravenous virus injection (FIGS. 2A and 4D). Although the treatment of mice with warfarin completely ablated Ad5 mediated hepatocyte transduction, the capacity of Kupffer cells to trap Ad virions remained unaffected (FIG. 4C). Moreover, it was found that in warfarin-treated mice, Ad transduces liver sinusoid endothelial cells (FIG. 3), a cell type not readily transduced by Ad virions after intravenous injection. The simultaneous elimination of Kupffer cells and ablation of a blood-factor pathway resulted in only a 35% reduction in the amounts of Ad DNA trapped in the liver after intravenous virus injection (FIGS. 5A, 5B).

Figure 8A:
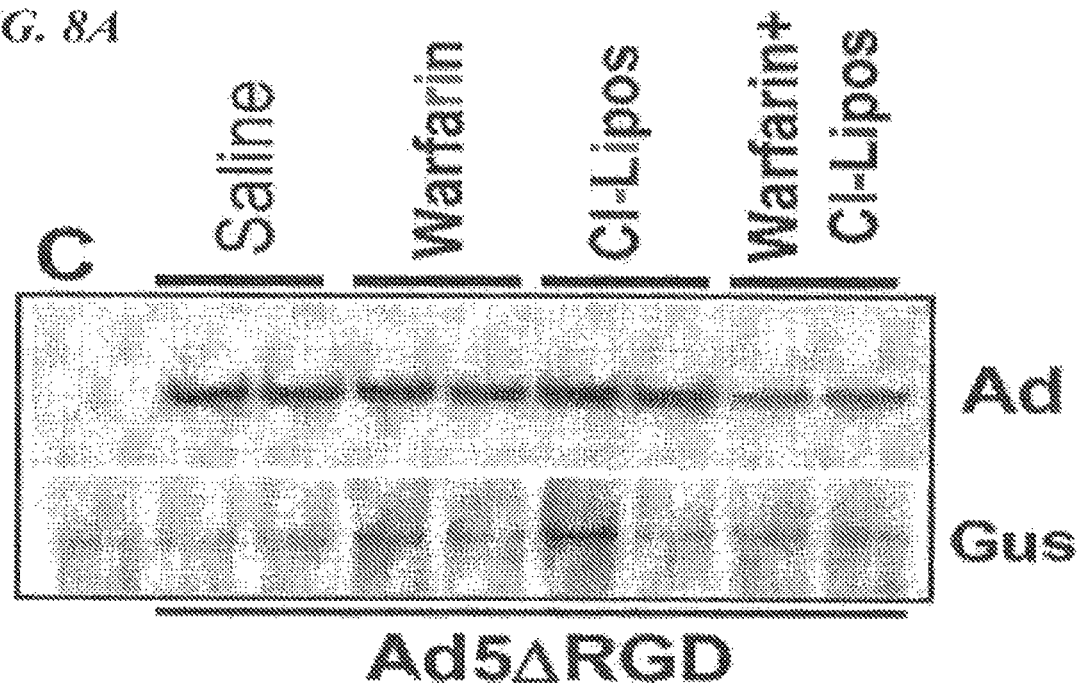
Figure 8B:
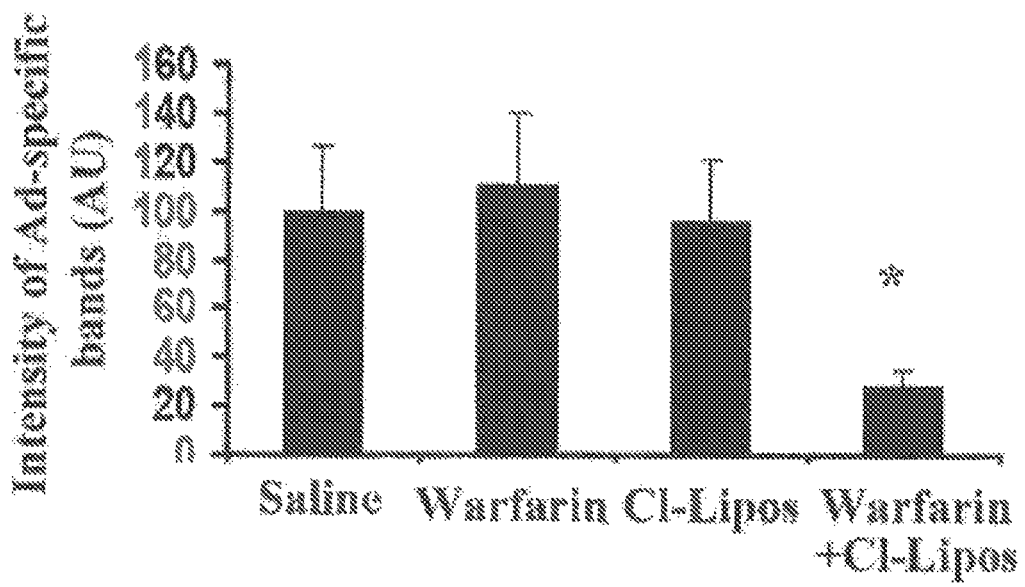

Evaluation of liver sections of mice treated with both clodronate liposomes and warfarin followed by Ad administration revealed that the large amounts of Ad particles were localized to the liver sinusoids as free particles. Administration of Ad5 into β3-integrin knockout mice that were treated with warfarin and clodronate liposomes further reduced the levels of Ad DNA sequestered by the liver (FIG. 7). The microscopically detectable association of Ad virions with liver sinusoids can be completely eliminated after injection of warfarin, and clodronate liposome-treated mice with an Ad5ΔRGD vector, possessing RGD motif-deletion within the penton base protein FIG. 7D). The levels of Ad5ΔRGD DNA trapped in the liver after intravenous virus injection in these mice were below 20% of the levels observed in animals treated with each of the drugs individually or untreated controls (FIG. 8). The data provides evidence for the redundancy and synergism of molecular pathways that control the sequestration of blood-born Ad virions in the liver tissue.

To provide for novel Ad vectors of the present invention that exhibit significantly reduced sequestration in the liver after circulation in the blood, a series of mutant Ad5-based vectors were constructed comprising individual mutations abrogating virus interaction with cellular β3 integrins in vivo (e.g. Ad5ΔRGD (FIG. 17), Ad-Lam1 (FIG. 20, SEQ ID No.: 3), and Ad-Lam3 (FIG. 20, SEQ ID No.: 4), blood coagulation factors (Ad-TEA, HVR7 T425A mutant, SEQ ID No.: 2, FIGS. 13,14), a virus Ad-2M, comprising combined mutations in penton RGD loop and hexon HVR7 loop (FIG. 21), and a virus Ad-3M, comprising three simultaneous mutations—1) the penton RGD-loop mutation (SEQ ID No.: 4); 2) the hexon HVR7 T425A mutation (SEQ ID No.: 2); and the novel hexon HVR1 mutation (SEQ ID No.: 5, FIGS. 22, 23). After intravenous injection of all of these viruses in mice, only Ad-3M virus escaped being sequestered in the liver, while all other virus variants were trapped in the liver at the amounts similar to those observed for wild type virus, Ad-WT, representing a capsid without any modifications (FIGS. 21C, 23B). The properties of genetic mutation of Ad hexon HVR1 loop, which are allowing for elimination of Ad interactions with liver Kupffer cells in vivo after intravascular virus delivery have never been reported and represent integral part of and innovative beneficial aspects of this invention.

In addition to escaping of being sequestered in the liver tissue, Ad-3M vector did not accumulate in Kupffer cells at a physical particle level (FIG. 23C), did not triggered their necrotic death (FIG. 23E), and was unable to activate inflammatory cytokines and chemokines in the spleen (FIG. 23D), demonstrating greatly reduced toxicity after intravascular administration, compared to control unmodified Ad-WT virus (SEQ ID No.: 1) or Ad-Lam1 (SEQ ID No.: 3), Ad-Lam3 (SEQ ID No.: 4), and Ad-2M vectors, comprising individual mutations in penton or penton and hexon HVR7 mutations only (FIG. 21C, 21D). These properties of the Ad-3M virus can be beneficial for human gene therapy applications and allow for escalating administered vector doses without compromising the safety of the therapy.

In another aspect, a DNA fragment encoding a mutant Ad hexon, penton, fiber, and/or non-structural protein and a vector for expressing such a DNA fragment, are provided. The necessary transcriptional and translational signals can also be supplied by the native Ad nucleic acids and/or its flanking regions, or can be heterologous. The DNA fragment can be, for example, an expression cassette. Such an expression cassette optionally can include a heterologous promoter operatively linked to a DNA fragment encoding a mutant Ad hexon. The vector can be, for example, a plasmid or virus, integrative or otherwise.

The DNA fragment, expression cassette and/or vector also can be combined with one or more substances capable of improving the transfection efficiency and/or the stability of the fragment, cassette or vector. Such substances include, for example, polymers, lipids (e.g., cationic lipids), liposomes, nuclear proteins and neutral lipids.

In certain embodiments, the Ad can be a recombinant and replication-defective Ad (i.e., incapable of autonomously replicating in a host cell). Such a replication-deficient Ad can include, for example, a mutation or deletion of one or more viral regions, such as, for example, all or part of the E1 region and/or E3 region. The genome of an Ad optionally can include additional deletions or mutations affecting other regions, such as, for example, the E2, E4 and/or L1-L5 regions, including complete deletion of the virus coding sequences and replacement with non-Ad DNA (so called "helper-dependent" vectors).

The Ad vectors can optionally be recombinant Ads and comprise one or more genes of interest contained within a nucleic acid segment, which is introduced into the Ad vectors. The genes of interest can be placed under the control of the elements necessary for their expression in a host cell. The gene of interest is typically a human or non-human heterologous gene (i.e., a non-Ad gene). The gene of interest can be, for example, genomic, cDNA (complementary DNA), a hybrid or chimeric gene (e.g., a minigene lacking one or more introns), or the like. It can be obtained, for example, by conventional molecular biology techniques and/or by chemical synthesis. A gene of interest can encode, for example, an antisense RNA, shRNA, lncRNA, or siRNA, a ribozyme or an mRNA that can be translated into a polypeptide of interest. A polypeptide of interest can be, for example, a nuclear, cytoplasmic, membrane, secreted or other type of protein. Further, the polypeptide of interest can be, for example, a polypeptide as found in nature, a chimeric polypeptide obtained from the fusion of sequences of diverse origins, or of a polypeptide mutated relative to the native sequence having improved and/or modified biological properties.

In certain embodiments, the nucleic acid segment can comprise a predetermined gene of interest that is configured to achieve a predetermined function or outcome. The gene of interest can encode, for example and without limitation, one of the following polypeptides: cytokines or lymphokines ($\alpha$-, $\beta$- or $\gamma$-interferon, interleukins (e.g., IL-1$\alpha$, IL-2, IL-6, IL-10, IL-12, IL-15, IL-15R, and IL-24), tumor necrosis factors (TNF), colony stimulating factors (e.g., GM-CSF, C-CSF, M-CSF, or the like)); cellular or nuclear receptors (e.g., those recognized by pathogenic organisms (e.g., viruses, bacteria or parasites)); proteins involved in activation of innate immune signaling of prokaryotic or eukaryotic origin (e.g. bacterial flagellin, or the like); proteins involved in triggering a genetic diseases (e.g., factor VII, factor VIII, factor IX, dystrophin or minidystrophin, insulin, CFTR protein (Cystic Fibrosis Transmembrane Conductance Regulator)); growth hormones (e.g., insulin, hGH or the like); enzymes (e.g., urease, renin, thrombin, or the like); enzyme inhibitors (e.g., al-antitrypsin, antithrombin III, viral protease inhibitors, or the like); polypeptides with antitumor effect (e.g., which are capable of at least partially inhibiting the initiation or the progression of tumors or cancers), such as antibodies, inhibitors acting on cell division or transduction signals, products of expression of tumor suppressor genes (specifically, but without limitation, p53 or pRb), proteins stimulating the immune system, or the like); proteins of the class I or II major histocompatibility complex or regulatory proteins acting on the expression of the corresponding genes; polypeptides capable of inhibiting a viral, bacterial or parasitic infection or its development (e.g., antigenic polypeptides having immunogenic properties, antigenic epitopes, antibodies, transdominant variants capable of inhibiting the action of a native protein by competition, or the like); toxins (e.g., herpes simplex virus 1 thymidine kinase (HSV-1-TK), ricin, cholera toxin, diphtheria toxin, or the like) or immunotoxins; markers (13-galactosidase, luciferase, Green Fluorescent Protein, or the like); polypeptides having an effect on apoptosis (e.g., inducer of apoptosis: Bax, or the like, inducer of apoptosis Bcl2, Bclx, or the like); cytostatic agents (e.g., p21, p16, Rb, or the like); apolipoproteins (e.g., apoE or the like); superoxide dismutase, catalase, nitric oxide synthase (NOS); growth factors (e.g., Fibroblast Growth Factor (FGF), Vascular Endothelial Cell Growth Factors (VEGFs), insulin, or the like), or others genes having therapeutic or research interest. It should be noted that this list is not limiting and that other genes can also be used. In certain embodiments, the polypeptide of interest is not a marker (e.g., $\beta$-galactosidase, luciferase, Green Fluorescent Protein, or the like).

The Ad optionally can include a selectable gene which allows for selection or identification of the infected cells. Suitable selectable genes include, for example, Neo (encoding neomycin phosphotransferase), DHFR (Dihydrofolate Reductase), CAT (Chlorainphenicol Acetyl transferase), PAC (Puromycin Acetyl-Transferase), GPT (Xanthine Guanine Phosphoriboxyl Transferase), or the like. In other embodiments, the Ad is free of selectable genes.

In certain embodiments, the gene of interest can optionally include elements necessary for the expression of the gene in a host cell. Such elements include, for example, elements facilitating transcription of the gene into RNA and/or the translation of an mRNA into a protein. Suitable promoters include, for example, those of eukaryotic or viral origin. Suitable promoters can be constitutive or regulatable (e.g., inducible). A promoter can be modified to increase promoter activity, suppress a transcription-inhibiting region, make a constitutive promoter regulatable, or the like, introduce a restriction site, or the like. Examples of suitable promoters include, for example, the CMV (Cytomegalovirus) viral promoter, the RSV (Rous Sarcoma Virus) viral promoter, the promoter of the HSV-1 virus TK gene, the early promoter of the SV40 virus (Simian Virus 40), the Ad MLP promoter, the eukaryotic promoters of the murine or human genes for PGK (Phospho Glycerate kinase), MT (metallothionein), al-antitrypsin and albumin (liver-specific), immunoglobulins (lymphocyte-specific), a tumor-specific promoter (e.g., a-fetoprotein AFP (see, e.g., Ido et al., Cancer Res. 55:3105-09 (1995)); MLJC-1; prostate specific antigen (PSA) (see, e.g., Lee et al., J. Biol. Chem. 271:4561-68 (1996)); and flt1 specific for endothelial cells (e.g., Morishita et al., J. Biol. Chem. 270:27948-53 (1995)).

A gene of interest can also include additional elements for the expression (e.g., an intron sequence, a signal sequence, a nuclear localization sequence, a transcription termination sequence, a site for initiation of translation of the IRES type, or the like), for its maintenance in the host cell, or the like.

Also provided are methods of preparing a human or non-human Ad vector according to the present disclosure. Such methods can include, for example, transfecting the genome of the Ad (encoding a mutant Ad hexon protein) into an appropriate cell line and culturing the transfected cell line under appropriate conditions in order to allow the production of the Ad. The Ad optionally can be recovered from the culture. In certain embodiments, e.g. for gene therapy and cancer therapy, the Ad is substantially purified.

The cell line can be selected according to the deficient functions in the Ad, as applicable. A complementation host cell line capable of providing in trans the deficient function(s) can be used. In certain embodiments, the 293 line is used for complementing the E1 function (see, e.g., Graham et al., I Gen. Virol. 36:59-72 (1977) (Graham and van der Eb, 1973)). A complementation host cell line also can complement multiple Ad gene deficiencies, such as, for example, a deficiency of the E1 and E2 or E4. In certain embodiments, a helper virus can be used to complement the defective Ad in a host cell. Methods of propagating defective Ads are known in the art (see, e.g., Graham and Prevec, Methods in Molecular Biology (ed. E. J. Murey, The Human Press Inc.), vol. 7, p. 190-128 (1997)). The Ad genome also can be reconstituted in vitro in, for example, *Escherichia coli* (*E. coli*) by ligation and/or by homologous recombination.

Further provided herein is a host cell infected with an Ad according to the present disclosure or capable of being obtained by a method according to the present invention. The infected host cell can be, for example, a mammalian cell, such as a human cell, or a nonhuman, animal cell. An infected host cell also can be, for example, a primary or tumor cell and of any suitable origin, for example, of hematopoietic (e.g., a totipotent stem cell, leukocyte, lymphocyte, monocyte or macrophage, or the like), muscle (e.g., a satellite cell, myocyte, myoblast, smooth muscle cell), cardiac, nasal, pulmonary, tracheal, hepatic, epithelial or fibroblast origin.

In addition to the examples of the embodiment of Ads and Ad vectors, provided herein are isolated nucleic acids encoding an Ad penton protein, the penton protein comprising a mutation in the RGD motif of the penton protein, wherein the mutation causes reduced binding of a host cell β3 integrin proteins in vivo, when expressed in an Ad. In a further aspect, disclosed herein are isolated nucleic acids, wherein the nucleic acid additionally encodes an Ad hexon protein, the hexon protein comprising a mutation in the HVR3, HVR5, or HVR7 region of the hexon protein, wherein the mutation causes reduced binding of a vitamin K dependent clotting factor in vivo when expressed in an Ad.

ii. Nucleic Acids

The provided nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

It is understood that nucleotide analogs need only contain a single modification, but may also contain multiple modifications within one of the moieties or between different moieties.

iii. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

1. Viral Promoters and Enhancers

Preferred promoters controlling transcription from vectors in mammalian host cells may be obtained from various sources, for example, the genomes of viruses such as: polyoma, Simian Virus 40 (SV40), Ad, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers f unction to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and Ad enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

2. Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes ß-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

iv. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

v. Pharmaceutical Carriers/Delivery of Pharmaceutical Products

In one aspect, it is understood and herein contemplated that the novel Ads of the present invention and nucleic acids can be used as a component in a pharmaceutical composition for therapeutic or prophylactic purposes. In one aspect, provided herein are pharmaceutical compositions comprising any of the Ads, Ad vectors, and nucleic acids disclosed herein. It is understood and herein contemplated that for reasons well-known in the art, it may be advantageous for any pharmaceutical composition to comprise a replication-defective or replication-attenuated recombinant Ad. In one aspect, the pharmaceutical composition can comprise an Ad, wherein the Ad is a replication-competent or replication-restricted to replicate in tumor cells only recombinant Ads.

Further provided are pharmaceutical compositions comprising a therapeutic or prophylactic agent, a host cell or an Ad, in combination with a pharmaceutically acceptable carrier. In certain embodiments, the composition can be used for preventive and/or treatment of diseases, such as genetic diseases (e.g., hemophilia, cystic fibrosis, diabetes, Duchenne's myopathy or Becker's myopathy, or the like), localized and disseminated metastatic cancers of solid or hematologic origin, including those induced by oncogenes or viruses, viral diseases, such as hepatitis B or C and AIDS (acquired immunodeficiency syndrome resulting from HIV infection), recurring viral diseases, such as viral infections caused by the herpesvirus and cardiovascular diseases including restenosis.

Accordingly, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129:57-80, (1992); and Roffler, et al.,

*Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

1. Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Therapeutic Uses

In one aspect, disclosed herein are methods of treatment according to which a therapeutically effective quantity of an Ad according to the present description or of a host cell is administered to a patient requiring such a treatment. Such methods can comprise treating a host with one or more pharmaceutical entities prior to, or after infection with Ad.

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

c. METHODS OF USING THE COMPOSITIONS i. Methods of Evading Sequestration of an Ad in the Liver

In one aspect, it is understood and herein contemplated that the Ads of the present invention are designed to evade the problem of sequestration of the Ad in a host's liver. Accordingly, disclosed herein are methods of administering an Ad such that the Ad virions evade sequestration in a host's liver, wherein the method comprises the steps of: a) providing an Ad with a mutation in the RGD motif of the penton protein, wherein the mutation causes reduced binding of β3 integrins of a host normal liver cell in vivo; b) reducing the binding of the Ad with a vitamin K dependent clotting factor (such as, for example Factor VII, Factor IX, Factor X, and Protein C) in the host; and, c) reducing the binding of the Ad to Kupffer cells.

It is understood and herein contemplated that the step of reducing the binding of the Ad with a vitamin K dependent clotting factor in the host can comprise providing an Ad with a mutation in the HVR3, HVR5, or HVR7 region of the hexon protein, wherein the mutation causes reduced binding of a vitamin K dependent clotting factor. In one aspect, reducing the bindning of the Ad with a vitamin K depending clotting factor can comprise the administration of a pharmaceutical entity, such as, for example, warfarin or treating the host with a pharmacological intervention that at least partially inactivates Kupffer cells comprising, for example, administering clodronate liposomes.

Additionally, it is understood that the step of preventing binding of the Ad with a Kupffer cells can comprise providing an Ad with a mutation in the HVR1 region of the hexon protein and/or treating the host with a pharmacological intervention that at least partially inactivates Kupffer cells comprises administering clodronate liposomes.

ii. Method of Treating Cancer

The disclosed Ad compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Compounds disclosed herein may also be used for the treatment of precancer conditions such as cervical and anal dysplasias, other dysplasias, severe dysplasias, hyperplasias, atypical hyperplasias, and neoplasias.

d. EXAMPLES

Figure 1:
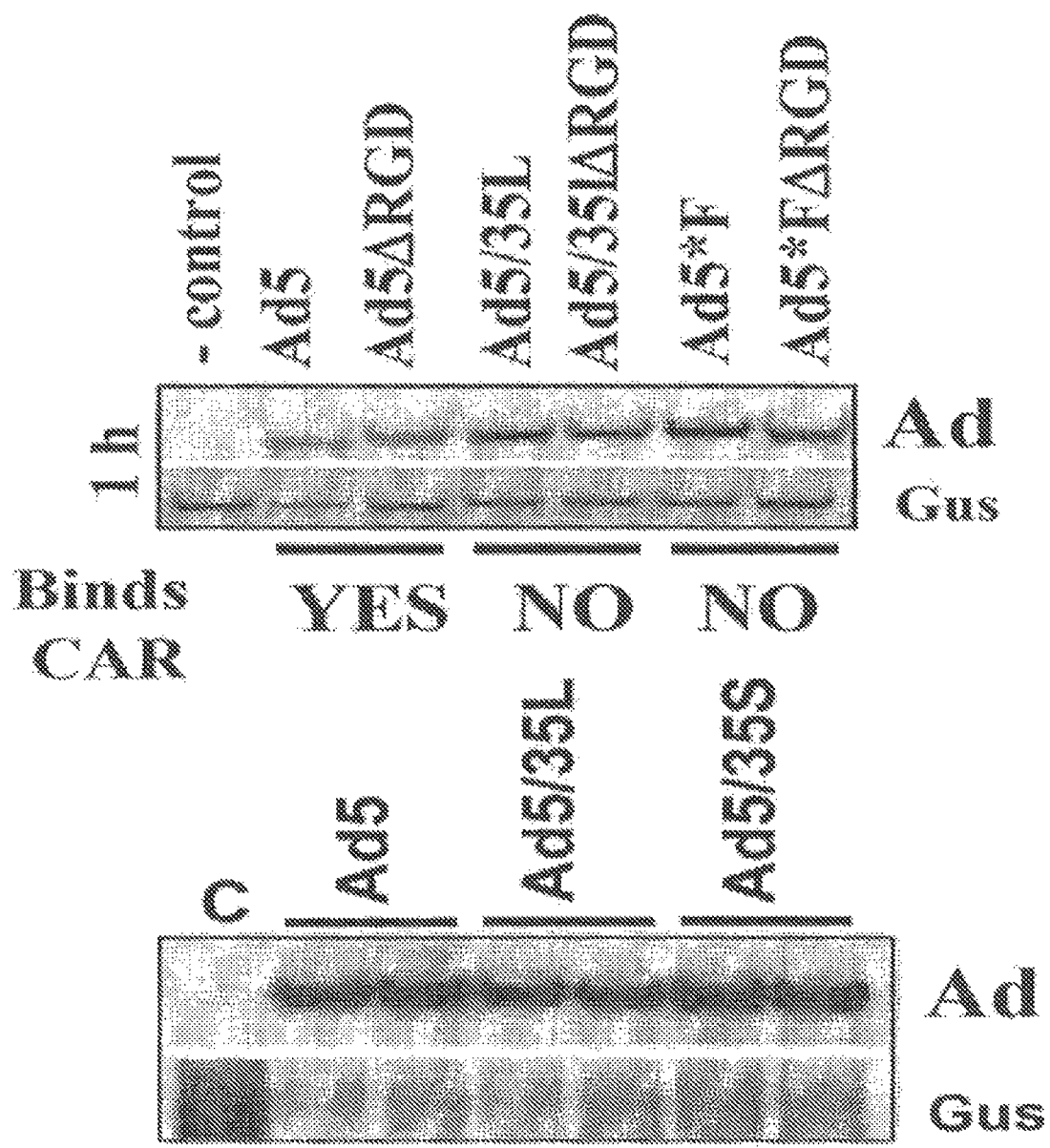

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

i. Example 1: Blood-Born Ad Virions are Efficiently Sequestered in the Liver Independently of the Virus Fiber Structure or RGD Motif-Mediated Penton Binding to Integrins To assess the potential role of the Ad fiber structure or an RGD motif-mediated penton binding to cellular integrins in mediating the sequestration of the blood-born virus particles in the liver, a set of the previously constructed Ad5-based vectors which possessed mutated fibers or RGD motif deletion within the penton base was utilized. Ad5 and Ad5ΔRGD vectors were able to bind CAR as a primary virus attachment receptor. Ad5/35L, Ad5/35LΔRGD, Ad5*F and Ad5*FΔRGD possessed the fiber knob domains that were unable to bind CAR due to a single point mutation within the Ad5 fiber knob that abrogates its binding to CAR (for Ad5*F and Ad5*FΔRGD), or due to the substitution of an entire Ad5 fiber knob domain for a fiber knob domain derived from Ad35, which binds human CD46 as a primary attachment receptor (for Ad5/35L, Ad5/35LΔRGD). Ad5/35S vector possesses a wild type Ad5 capsid except for the fiber shaft and knob domains that were derived from Ad35. All these vectors were injected intravenously into C57BL6/J mice and 1 h later, livers were harvested and the amount of Ad DNA trapped in the liver for each of the vectors was analyzed using Southern blotting. This analysis revealed that independently of modifications of the fiber or the RGD motif deletion in the penton base, all vectors accumulated at comparable levels in the liver (FIG. 1). This example provides direct evidence that the prior art disclosed in U.S. Pat. No. 5,712,136 does not teach on or enable the construction of the Ad of the present invention that escapes sequestration in the liver after intravascular administration in vivo.

ii. Example 2: Inactivation of the Blood Factor Pathway of Hepatocyte Transduction does not Prevent Blood-Born Ad Virion Sequestration in the Liver or Virus Accumulation in Kupffer Cells When Ad5 is injected intravenously, virus hexon protein binds coagulation factor X with very high affinity and that this interaction leads to efficient virus entry into hepatocytes and hepatocyte transduction in vivo. To better understand whether inactivation of this in vivo pathway of Ad virion entry into hepatocytes would result in the reduction of the amounts liver-sequestered Ad particles after intravenous virus injection, unmodified Ad virus as administered into control untreated mice and mice treated with warfarin, which inactivates all vitamin K-dependent blood coagulation factors. Analysis of Ad DNA trapped in the liver 1 h after intravenous virus injection showed that warfarin treatment did not result in a significant reduction of Ad virion sequestration in the liver at this time point (FIG. 2A).

Figure 2B:
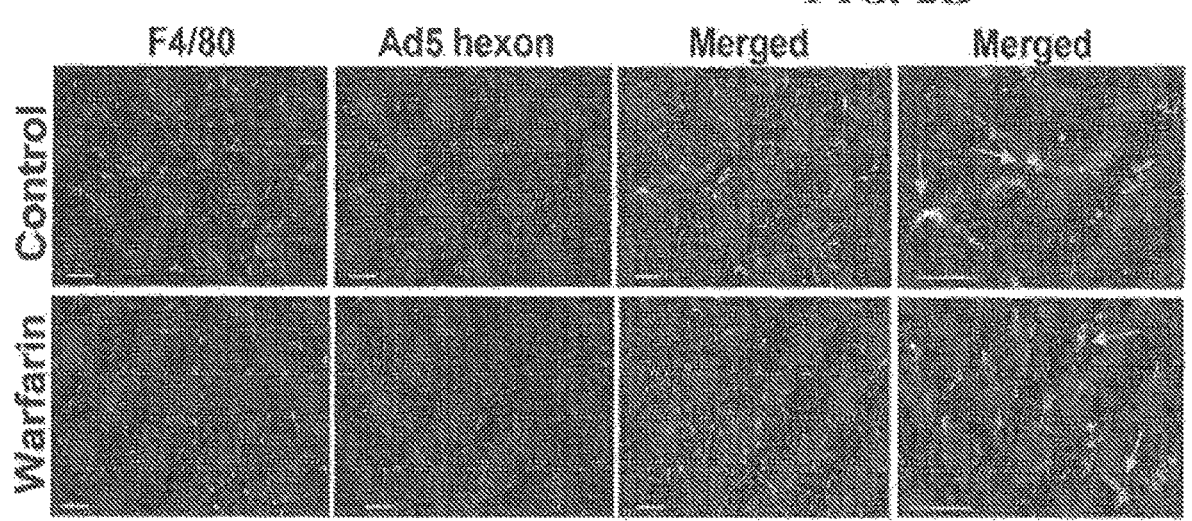

After intravenous injection, large amounts of Ad virions are known to be trapped by liver residential macrophages, Kupffer cells. To assess whether the Kupffer cell capacity to trap blood-born Ad particles is changed in mice treated with warfarin, Ad5 was administered intravenously and 1 h later analyzed the co-localization of virus particles with Kupffer cells by immunostaining and fluorescent microscopy. This analysis revealed that in the control and warfarin-treated mice, Kupffer cells were present in the liver (FIG. 2B). Importantly, when liver sections of mice were co-stained with Ad5 hexon-specific antibody and F4/80 antibodies, a clear co-localization of Ad hexon-specific staining was observed with Kupffer cells (FIG. 2B), indicating that warfarin treatment of mice did not ablate the Kupffer cell capacity to trap blood-born Ad.

Figure 2C:
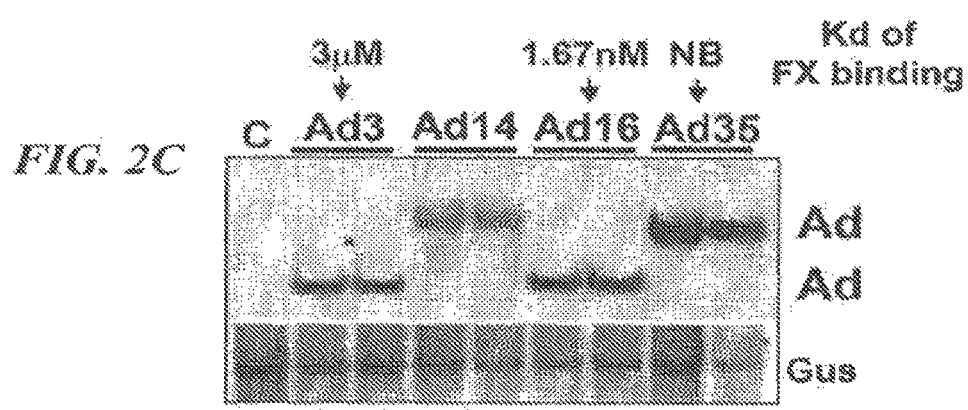

Different wild type human Ad serotypes show high variability in Kds of FX binding to their capsids. To further evaluate whether variations in amino acid composition of the exposed regions of hexon and Kds of FX binding can affect the efficacy of Ad virion sequestration in the liver, mice were injected intravenously with wild type human Ad serotypes Ad3, Ad14, Ad16, and Ad35. Herein it is shown that Ad16 has 1.67 nM Kd of FX binding, while Ad3 has Kd of FX binding equal 3000 nM and Ad35 did not demonstrate FX binding at all. The evaluation of sequestration of these viruses in the liver after intravenous administration showed no difference in the amounts of Ad3 and Ad16 and higher levels of Ad35 DNA (FIG. 2C), indicating that virus binding to FX cannot be the only important pathway mediating the sequestration of the blood-born Ad virions in the liver.

To analyze whether the treatment of mice with warfarin had any effect on the Ad-mediated hepatic cell transduction, control mice and warfarin-treated mice were administered Ad5RFP vector, possessing unmodified wild type Ad5 capsid, but expressing red fluorescent protein under the control of CMV promoter. Histological evaluation of liver sections for RFP expression showed that Ad5RFP transduced hepatocytes with very high efficiency in control mock-treated mice (FIG. 3A upper panels). Also, the treatment of mice with warfarin completely abrogated Ad5-mediated hepatocyte transduction. Surprisingly, detailed evaluation of liver sections also revealed that in the warfarin-treated group, Ad5RFP also transduced sinusoid endothelial cells (FIG. 3A, lower panels, and 3B). Although the level of RFP expression in these cells was quite low, RFP expression was detected in 10.8% of all analyzed cells. CD31/RFP-double positive cells represented 17% of all CD31-positive endothelial cells. In contrast, RFP expression was not observed in β2-integrin-positive cells of hematopoietic origin, including circulating and residential monocytes and macrophages (FIG. 3B). Collectively, the data indicate that although warfarin-mediated inactivation of the blood factor pathway of hepatocyte infection completely abrogates Ad virions hepatocyte transduction, it does not appreciably affect Ad virions sequestration in the liver after intravenous virus injection. Moreover, wild type human Ad serotypes that vary dramatically in their Kds of FX binding accumulate in the liver at comparable levels after intravenous virus administration. The treatment of mice with warfarin did not prevent Ad accumulation in Kupffer cells; however, it allowed for re-direction of Ad infection from hepatocytes to sinusoid endothelial cells.

iii. Example 3: The Depletion of Kupffer Cells has No Effect on Ad Sequestration in the Liver Kupffer cells are known to accumulate large amounts of Ad particles shortly after intravenous virus administration. Polyinosinic acid, poly(I), administration into mice prior to Ad injection drastically reduces the capacity of Kupffer cells to trap blood-born Ad in vivo. This data suggest that a poly(I)-specific receptor, scavenger receptor A, can be involved in sequestering Ad virions from the blood after its intravenous injection. To evaluate this possibility, Ad5-based vectors were administered into wild type or scavenger receptor A knockout mice (SR-A-KO) and analyzed both virus DNA deposition in the liver by Southern blotting and virus trapping in Kupffer cells by fluorescent microscopy. These analyses showed that in both control wild type mice and SR-A-KO mice, Kupffer cells retained the capacity to accumulate Ad particles after intravenous virus administration (FIG. 4A). It was also found that the amount of Ad vector DNA that could be recovered from the liver after intravenous virus injection was virtually identical in wild type and SR-A-KO mice (FIG. 4B), indicating that SR-A is not, or at least cannot be, the only receptor responsible for the Kupffer cells capacity to trap blood-born Ad in vivo.

Figure 5C:
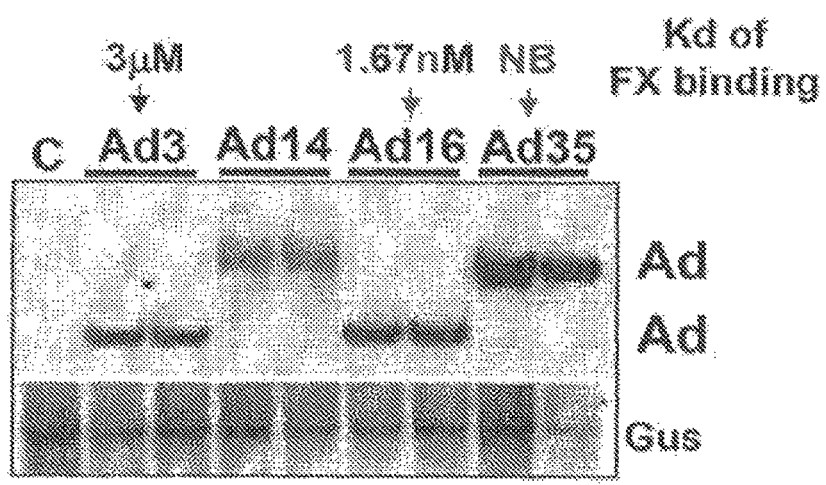

Next, whether the depletion of these phagocytic cells can reduce the liver's capacity to sequester the blood-born Ad was analyzed. To deplete Kupffer cells, macrophage elimination by a single dose clodronate liposome injection was used. Intravenous administration of clodronate liposomes into mice resulted in complete elimination of Kupffer cells from the liver (FIG. 4C). However, the Southern blot analysis of Ad DNA amounts in the livers of clodronate liposome-treated mice or control mice treated only with PBS showed no difference in the amounts of Ad trapped in the liver independently of the presence of Kupffer cells in liver parenchyma (FIG. 4D).

iv. Example 4: Simultaneous Treatment of Mice with Warfarin and Clodronate Liposomes Results in an Only Partial Reduction in Liver Capacity to Sequester Blood-Born Ad The findings that inactivation of blood factor pathway or depletion of Kupffer cells resulted in no measurable reduction in the amounts of Ad DNA trapped in the liver after intravenous virus administration were rather unexpected, since large amounts of Ad particles accumulate in Kupffer cells and Ad DNA persists long-term in transduced hepatocytes. The data indicates that a dynamic balance can exist between the mechanisms of the Ad sequestration by Kupffer cells and hepatocytes in vivo. This data also indicates that the mechanisms of sequestration of blood-born Ad can work in a redundant and synergistic manner. To evaluate this possibility, the sequestration of Ad DNA in the livers of mice treated with both the warfarin and clodronate liposomes prior to Ad administration was analyzed. This analysis revealed that when harvested at 1 h after intravenous Ad injection, the amount of virus DNA trapped in the liver was 35% lower in mice treated with both warfarin and clodronate liposomes, compared to mice treated with warfarin only (FIGS. 5A, 5B). Although the difference between these two experimental groups was statistically significant, it was not dramatic. Close evaluation of Ad distribution in the livers of mice treated with warfarin and clodronate liposomes showed abundant punctuate Ad-specific staining localized to liver sinusoids (FIG. 5C). Because this type of Ad distribution in the livers of mice treated with either warfarin or clodronate liposomes independently was not observe, the data indicate that yet another mechanism of Ad sequestration became engaged when both Kupffer cells and the blood factor pathway are inactivated. Because Ad particles might accumulate in platelets, liver sections were stained with a platelet-specific anti-CD41 antibody. Using this approach, Ad hexon-specific staining was found to be co-localized with CD41-specific staining in very few areas, while the vast majority of punctuate Ad hexon-specific staining was not overlapping with CD41 staining.

Figure 6A:
Figure 6B:
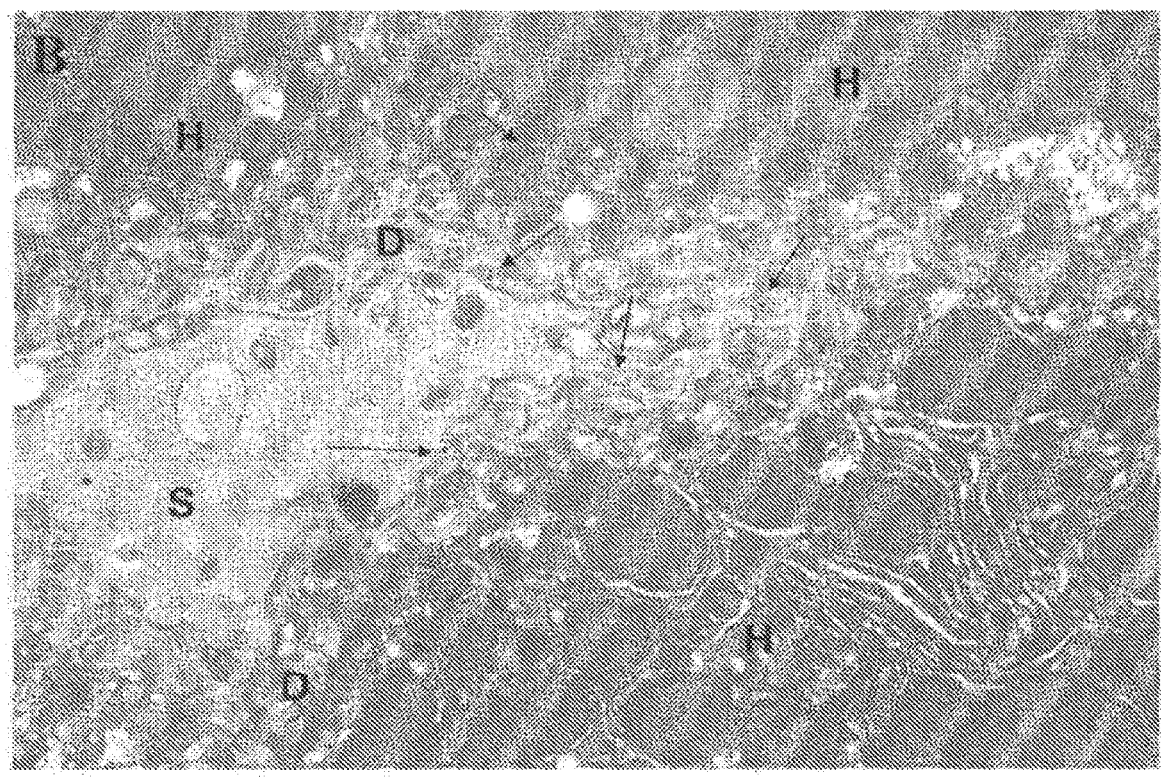

To better define the localization of Ad particles in the liver sinusoids of mice treated with warfarin and clodronate liposomes, transmission electron microscopy was employed. One hour after virus injection, liver tissue was harvested, fixed, and processed for ultra-thin sectioning. Electron microscopy analysis revealed that cytoplasmic organization of hepatocytes was highly distorted in warfarin-treated mice, indicating a major cytotoxic effect of this drug on hepatic cells. Ad particles were easily identifiable on thin sections and were localized to the Disse space, the anatomical area underneath and between sinusoid endothelial cells and the hepatocyte surface (FIG. 6). As expected, Ad particles were present in liver sinusoids as free particles (FIG. 6).

Collectively, this data indicates that under the conditions when sequestration mechanisms mediated by Kupffer cells and blood coagulation factors are not functioning, Ad trapping in the Disse space between liver sinusoids endothelial cells and hepatocytes can become the major mechanism responsible for trapping large amounts of blood-born Ad in the liver.

v. Example 5: RGD Motif-Mediated Ad Interactions Play a Major Role in Sequestering Blood-Born Ad in the Liver when Other Virus Clearance Mechanisms have been Inactivated The Ad internalization into cells is facilitated by the penton base RGD motif-mediated binding to cellular integrins. Many RGD motif-interacting integrins were shown to serve as functional co-receptors, capable of facilitating Ad internalization into different kinds of cells. Moreover, it was shown that Ad interaction with integrins can mediate both the virus attachment to and internalization into cells. Because RGD motif-interacting β3-integrin is a subunit $α_vβ3$ integrin expressed on endothelial cells, sequestration of blood-born Ad in the liver can be reduced in mice that are knockout for β3-integrin gene. To evaluate this further, β3-KO mice were administered with Ad5 with or without treatment with warfarin and clodronate liposomes and ana- lyzed the virus DNA deposition in the liver by Southern blotting. This analysis revealed that although the accumulation of Ad5 in the livers of wild type control and β3-KO mice was comparable, the treatment of β3-KO mice with warfarin and clodronate liposomes resulted in a significantly greater reduction in levels of Ad trapped in the liver after intravenous virus injection, compared to wild type animals (FIGS. 7A-7B). The analysis of Ad trapping in Kupffer cells after intravenous virus administration showed that in both strains of mice, Kupffer cells were capable of trapping blood-born Ad (FIG. 7C), indicating that β integrin is unlikely to contribute significantly to the capacity of Kupffer cells to trap blood-born Ad particles.

To further evaluate if Ad penton RGD motif-mediated interactions are responsible for Ad retention in the Disse space, wild type mice were injected with an Ad5ΔRGD vector, possessing a three amino acid deletion in the penton base. Using Southern blotting, a major reduction in levels of Ad DNA was observed to be recovered from the livers of wild type mice treated with warfarin and clodronate liposomes that were injected with Ad5ΔRGD vector (FIG. 7A). The levels of Ad5ΔRGD DNA associated with the liver were 30%, compared to the levels of Ad5 DNA in mice treated with both warfarin and clodronate liposomes, and were 18% compared to Ad5 DNA levels in the mock-treated control group (FIG. 7B). The analysis of Ad5ΔRGD distribution in the livers of mice treated with warfarin and clodronate liposomes using fluorescent microscopy showed a complete lack of Ad-specific staining (FIG. 7D).

To further verify the role of the Ad penton RGD motif in mediating the trapping of blood-born Ad in the liver, and to assess the engagement order of pathways governing this process, Ad5ΔRGD was administered into mice treated with either warfarin or clodronate liposomes alone. The analysis of Ad DNA deposition in the livers of these mice showed that, similarly to mice injected with control unmodified Ad5, treatment with either warfarin or clodronate liposomes alone did not result in a measurable reduction of vector DNA trapped in the liver after intravenous injection (FIG. 8). However, the combination of pharmacological treatment of mice simultaneously with warfarin and clodronate liposomes and the ablation of RGD motif-mediated interactions resulted in a major reduction in the amount of vector DNA associated with liver tissue, providing the evidence for the redundancy and synergism of molecular mechanisms that operate in the liver and enable quantitative removal of the Ad from the blood and trapping it in the liver tissue after intravenous Ad injection (FIG. 9).

vi. Example 6: Hexon-Modified Ads that are Ablated for Binding to Blood-Coagulation Factors Hexon modifications that can ablate Ad5 hexon binding to blood coagulation factors include deletion of TET amino acid sequence in HVR7 (FIG. 11A), or it substitution for an amino acids including, but not limited to, NAA (Ad51-derived HVR7 sequence, which does not bind FX, FIG. 12D), or mutation of the hexon in any other way to functionally inactivate coagulation factor binding. Another example of a modification that can ablate coagulation factor binding is the insertion of positively-charged amino acids (R, K, H) in HVR7 or HVR3, thus mimicking the natural geometrical arrangement of amino acids in Ad3 and Ad5, which do not bind FX efficiently, although they possess canonical FX binding TDT sequence in HVR3 (FIG. 12D, continued).

Specific minimal mutation of Ad hexon allowing for complete ablation of Ad interaction with coagulation factors, including but not limited to FX and FVII, is a single amino acid substitution of Threonine (425) for Alanine (T425A, FIGS. 13 and 14A,B). This mutation is sufficient to abrogate all FX-dependent interaction of Ad with the host, including efficient hepatocyte transduction and induction of a select subset of NF-κB-dependent inflammatory cytokines and chemokines including IL-1β, IL-6, and MIP1α (FIG. 15). However, this mutation alone does not prevent Ad trapping in tissue macrophages, including Kupffer cells (FIG. 22D), splenic marginal zone macrophages (FIGS. 14G, 14H, Ad-TEA variant) or virus sequestration in the liver (FIG. 22C) after intravenous virus administration.

vii. Example 7: Penton-Modified Ads that are Ablated for Binding to Cellular β3 and β5 Integrins Ad5ΔRGD virus possesses a tri-amino acid deletion within flexible Ad5 penton loop that ablates Ad5 interaction with integrins via RGD motifs (FIG. 17).

Penton modifications that can abrogate Ad5 interactions with integrins can include deletion of an entire integrin-interacting RGD motif-containing loop of Ad5 penton, deletion or substitution of only three amino acids R-G-D (FIGS. 16, 17), or mutation of the penton in any way to prevent functional penton interactions with β3 and β5 integrins.

The Ad interaction with β3 integrin class on macrophages activates a unique signaling pathway of innate immunity that is driven by IL-1α-IL-1R1 signaling (FIG. 18). Ad5ΔRGD virus, possessing deletion of RGD amino acid motif and, therefore, ablated for binding to RGD-interacting integrins, failed to functionally activate IL-1α-dependent pro-inflammatory signaling (FIGS. 18, 19), resulting in reduced or negligible levels of inflammatory cytokine and chemokine activation in the liver and spleen after intravascular virus administration, compared to unmodified Ad-WT virus (FIG. 18E). This pro-inflammatory response of macrophages to Ad is driven by specific interaction of the virus penton RGD motifs with β3 class integrins, since administration of the wild type unmodified Ad into β3 integrin-deficient mice triggered low to no inflammatory cytokine activation (IL-1α, IL-1β, IL-6, TNF-α, FIG. 18). This finding represents the basis for the construction of Ad variants with modified pentons that exhibit significantly lower levels of inflammation and therefore improved toxicity profiles, compared to Ad variants with RGD motif-containing pentons.

Another example of a modification that can ablate the penton interaction with integrins via RGD motifs is a substitution of an RGD-motif-containing flexible loop of Ad5 with an amino acid sequence(s) that contains no RGD motifs and that is able to selectively target Ad to a specific subset of integrins or other receptors, which are not expressed efficiently on liver cells, but can be expressed on tumor cells in vivo. These types of receptors include, but not limited to, α3β1, α6β4, or α6β1 integrins, which are highly expressed on tumor cells, but not on liver cells in vivo.

To target Ad to non-natural classes of integrins via a non-RGD motif containing peptides, inserted into Ad5 penton instead of RGD loop, Ad-Lam1 and Ad-Lam3 vectors were constructed (FIG. 20). Ad5-Lam1 vector contains 50 amino acids surrounding SIKVAV amino acid motif from human Laminin-1 (SEQ ID No.: 3). Ad5-Lam3 vector contains 54 amino acids surrounding SKVAV amino acid sequence from human Laminin-3 (SEQ ID No.:4). Both of these laminin-derived sequences contain no R-G-D amino acid motifs, yet are able to bind to α6β1 integrins via SIKVAV or SKVAV motifs on 293 cells to enable virus entry and propagation.

Other examples of iso-functional Ad5 RGD loop substitution with non-RGD motif-containing peptides to enable the virus targeting to non-β3 integrins are shown in FIG. 25. (SEQ ID Nos.: 9, 10)

viii. Example 8: Ad Vectors Possessing Mutations in Hexon and Penton, Allowing the Virus Particles to Escape Trapping in the Liver at a Physical Particle Level after Intravascular Administration Ad5 virus particles (FIG. 21, Ad-2M) with hexon mutation T425A, described in Example 6 and penton mutations described in Example 7, were intravenously injected into mice and virus trapping in the liver was analyzed 1 hour after virus administration. No significant difference in the amount of Ad-2M virus trapped in the liver was found, when compared to control unmodified Ad-WT virus, or viruses containing individual mutations either in hexon (H425A, Ad-TEA) or penton (Ad-Lam3, Ad-Lam, FIG. 21C). Kupffer cells in the liver trapped Ad-2M virus particles as efficiently as Ad-WT particles (FIG. 21D). This data is consistent with finding from mice pharmacologically conditioned with warfarin (to inactivate blood coagulation factors) and injected with Ad5ΔRGD and demonstrated no reduction in the levels of virus particles sequestered in the liver, compared to unmodified virus or saline-conditioned mice (FIG. 8A).

Ad2-M virus was used as a platform, and additional novel deletion was introduced into hexon HVR1 loop (SEQ ID No.: 5), which was empirically found to allow for the virus to escape being trapped in Kupffer cells after intravascular virus administration (FIG. 22). The resultant virus, Ad-3M, represents one of the preferred embodiments of the invention which is based on human Ad serotype 5 and contains simultaneously three mutations, namely two mutations in hexon and one in penton (FIG. 23A). When injected intravenously, Ad-3M virus demonstrated significantly reduced accumulation in the liver at a physical particle level, including Kupffer cells (FIG. 23B, C, E), compared all other vectors, including Ad-WT, a wild type virus comprising no modifications in capsid proteins.

The specific mutation in Ad5 hexon HVR1 loop described in FIG. 22 (SEQ ID No.: 5) and its embodiment in Ad-3M virus are provided as an example only without limitations for alternate modifications. The other examples of mutation in HVR1 can include, but not limited to, substitutions of the HVR1 loop between amino acids D136 and K165 with GGSG glycine linker, so that the entire sequence of the new HVR1 extended deletion in the resultant vector reads: 136-DEAAT-GGSG-QQK-165 (SEQ ID No.: 6). Another modifications of Ad5 HVR1 loop can also include the transplantation of HVR1 loop from any other human or animal Ad serotype, such as Ad41 (natural short) and Ad51 (natural intermediate) in place of HVR1 of Ad5 (FIG. 22) to generate vectors with chimeric HVR1 sequences from Ad41 135-W-KDNN-K-165 (SEQ ID No.: 7); and from Ad51 135-W-EQKKTTGGGNDME-TH-167 (SEQ ID No.: 8).

Intravenous administration of Ad-3M virus also triggered little to none inflammatory cytokine activation in the spleen and, in contrast to mice injected with Ad-WT virus, no Kupffer cell death was observed in mice injected with Ad-3M vector 1 hour after virus injection (FIG. 23E). This data shows an equifunctional role of three distinct hepatocellular compartments in enabling Ad trapping in the liver after intravascular administration and implicates specific molecular mechanisms in mediating virus-hepatic cell interaction (FIG. 24). This model necessitates the introduction of three specific mutations into Ad5-based vectors to allow for virus escape from being sequestered by the liver after intravascular administration, as exemplified for the preferred embodiment of this invention, Ad-3M vector (FIG. 23).

Upon targeting to extrahepatic (tumor cells and metastases in other organs) or non-hepatic cells in the liver (tumor metastases in the liver) via fiber modifications or by other means (FIG. 26), the virus dose that is therapeutic for the described penton and hexon-mutated vectors, can be much lower and resulting in viral safety being much higher, due to the low acute systemic toxicity of such a virus, compared to unmodified virus variants.

ix. Example 9: Discussion

Ad is a non-enveloped virus with a double-stranded linear DNA genome (Shenk, 2001). The susceptibility of cells to virus infection in vitro was ascribed, at least in part, to efficient Ad fiber binding to a specific attachment receptor on the cell surface (Nemerow, 2000). For human species A, C, D, E, and F Ad serotypes, CAR was shown to bind the fiber knob domain and mediate efficient virus entry into cells in vitro (Roelvink et al., 1998). For the majority of human species B serotypes, CD46 was identified as a high affinity virus attachment receptor (Gaggar et al., 2003). The fiber binding to the virus attachment receptor is followed shortly by the RGD motif dependent interaction of a penton base protein to cellular integrins (Wickham et al., 1993). This interaction promotes Ad particle internalization into the cell as well as initiates the virus capsid disassembly program. Different Ad serotypes infect a variety of cells in vitro and in vivo with high efficiency. Based on this property of Ad, numerous Ad-based vectors have been developed for gene transfer and vaccination studies (Thomas et al., 2003). However, when Ad vectors were delivered at high doses or via routes not associated with natural Ad infection, the infectivity and tissue bio-distribution did not correlate with the levels of the fiber attachment receptors (Alemany and Curiel, 2001). Specifically, after intravenous injection of human Ad5-based vectors, 99% of the delivered vector dose is rapidly sequestered in the liver (Khare et al., 2011a). Moreover, ablation of both CAR and integrin interactions through mutation of Ad fiber and penton proteins did not prevent virus accumulation in the liver and efficient hepatocyte transduction (Shayakhmetov et al., 2004). The efficient interaction between Ad and liver cells causes clinically significant hepatotoxicity and represents a major hindrance if gene delivery to extra-hepatic cells and tissues, such as disseminated metastatic tumors, is required.

The liver residential macrophages, Kupffer cells, are amongst the most studied factors contributing to rapid sequestration of blood-born Ad in the liver (Di Paolo et al., 2013; Di Paolo et al., 2009b; Khare et al., 2011b; Lieber et al., 1997; Manickan et al., 2006; Wolff et al., 1997; Worgall et al., 1997). After intravenous virus injection, Kupffer cells trap large amounts of virus particles. This accumulation of Ad particles in Kupffer cells causes a non-linear dose response for Ad vector-mediated transgene delivery into hepatocytes. Ad interactions with Kupffer cells induce activation of inflammatory responses. Recent data suggests that high dose intravenous Ad administration can induce rapid Kupffer cell death that might also contribute to activation of pro-inflammatory host responses (Di Paolo et al., 2013). On the other hand, it was also shown that inactivation of Kupffer cells prior to intravenous Ad administration significantly increases the levels of circulating virus and transduction of hepatic and extra-hepatic cells (Khare et al., 2013; Khare et al., 2011b; Wolff et al., 1997). Although Kupffer cells can accumulate large amounts of blood-born Ad, virus entry into Kupffer cells does not lead to their transduction in vivo, indicating that Kupffer cells represent a poor niche for Ad propagation. Instead, Kupffer cell rapidly die via a necrotic type of cell death (Di Paolo et al., 2013; Manickan et al., 2006). Collectively, these data strongly indicated that Ad rapping by Kupffer cells is the first in line of the potential mechanisms mediating sequestration of blood-born Ad in the liver.

The data obtained in this study indicates however, that the Ad trapping by Kupffer cells is not the only mechanism responsible for the sequestration of blood-born Ad in the liver. Surprisingly, complete elimination of Kupffer cells from the liver parenchyma after clodronate liposome administration led to no reduction in Ad DNA sequestered in the liver after intravenous virus injection (FIG. 4). This data indicates that functional inactivation of Kupffer cells with gadolinium chloride also failed to reduce the amount of Ad DNA trapped in the liver shortly after intravenous virus injection. Because elimination of Kupffer cells leads to marked increase in the level of Ad-mediated hepatocyte transduction, the data indicates that the vector particles that escaped sequestration by Kupffer cells are now efficiently entered hepatocytes, resulting in greatly increased levels of transgene expression.

The earlier data suggested that the entry of Ad5 into hepatocytes is mediated by blood factors and does not depend on virus interactions with CAR or integrins (Kalyuzhniy et al., 2008; Waddington et al., 2008). Recent studies clearly demonstrated that high affinity Ad5 hexon binding to coagulation factor X is sufficient to mediate hepatocyte transduction with Ad5 vectors in vivo. Parker at al., have shown that the treatment of mice with the drug warfarin, inactivating all vitamin-K blood coagulation factors, ablates hepatocyte transduction with intravenously injected Ad5 vectors (Parker et al., 2006). Although warfarin treatment of mice completely abrogated hepatocytes transduction with Ad5 vectors in this study (FIG. 3), it was found that the amount of Ad DNA sequestered in the liver was similar in warfarin-treated and control mice (FIG. 2). The earlier studies showed that when liver tissue is perfused with Ad5 in situ in blood-free conditions, Kupffer cells can accumulate Ad particles in a blood factor (FIX)-dependent manner (Shayakhmetov et al., 2005).

Here, it was found that in warfarin-treated mice, Kupffer cells retain the capacity to trap blood-born Ad, indicating that the blood factor-mediated pathway of Ad entry in Kupffer cells is not the only one to control Ad-Kupffer cell interactions. This observation indicates that Kupffer cells can bind Ad via SR-A, since pre-injection of mice with SR-A-specific ligand poly(I) drastically reduced Ad accumulation in Kupffer cells after intravenous virus injection (Haisma et al., 2008). The quantitative analysis of Ad accumulation in the liver and qualitative evaluation of Ad trapping in Kupffer cells using SR-A-KO mice showed that both the amounts of Ad DNA and the capacity of Kupffer cells to accumulate Ad particles were similar in SR-A-KO and control mice (FIG. 4). The data presented herein strongly indicates that the SR-A-dependent mechanism is unlikely to play a dominant role in mediating Ad interaction with Kupffer cells. The effect of poly(I) on Ad trapping in Kupffer cells can be explained by alternate indirect mechanisms, where the signaling downstream of SR-A, upon its binding to poly(I), can block or interfere with Kupffer cell phagocytic function or endosome formation.

The lack of a significant reduction in the amounts of Ad DNA sequestered in the livers of Kupffer cell-depleted or warfarin-treated mice, when compared to control animals, indicates that a previously unknown redundancy and synergism between different mechanisms controlling sequestration of blood-born Ad in the liver exists. To evaluate this further, mice were treated with both warfarin and clodronate liposomes and analyzed Ad sequestration in the liver after intravenous virus injection. The studies unexpectedly revealed only a modest reduction in the amounts of Ad DNA sequestered in the livers of mice treated with the combination of drugs. While 35% less Ad DNA was trapped in livers of mice treated with both warfarin and clodronate liposomes, 65% of Ad DNA still remained trapped in livers of mice that lacked Kupffer cells and possessed no coagulation factors in blood (FIG. 5). This data that Ad sequestration mechanisms likely operate in a redundant and synergistic manner and an unknown sequential order of engagement of these mechanisms to ensure efficient clearance of blood-born Ad from circulation. The detailed analyses of Ad particle distribution in the liver parenchyma using fluorescent microscopy and electron microscopy revealed abundant dispersed Ad particles localized to liver sinusoids (FIG. 7). Because this type of virus distribution was not observed in livers of mice treated with each drug independently, or in mock-treated animals, this data indicates that new interactions of Ad with liver cells become activated only under the condition when other sequestration mechanisms have been inactivated.

In this study, it was demonstrated that Ad penton RGD motifs contribute to virus trapping in the space of Disse that separates liver sinusoid endothelial cells from hepatocytes. The analysis of Ad deposition in the livers of β3-integrin-knockout mice indicates that β3-integrin, contributes to this interaction. Because 43 integrin is expressed on endothelial cells, when Ad particles cannot enter hepatocytes, they can bind RGD-interacting integrins with β3-integrin subunit on sinusoid endothelial and thus become retained in the Disse space, leading to eventual internalization into endothelial cells or hepatocytes, and virus clearance from circulation. The data, demonstrating low level sinusoid endothelial cell transduction with Ad in mice treated with warfarin, supports this idea (FIG. 3).

The data uncovered a previously unknown redundancy and synergism in mechanisms mediating the sequestration of blood-born Ad in the liver. A model was proposed for sequestration of blood-born Ad in the liver (FIG. 9). This conceptual model indicates that a defined set of specific molecular mechanisms become engaged in a redundant, synergistic, and orderly manner to ensure the clearance of blood-born Ad from circulation. When small amounts of Ad particles appear in blood, the virus trapping by Kupffer cells works as a first dominant mechanism, mediating Ad sequestration in the liver. When the Ad dose exceeds the capacity of Kupffer cells to trap the virus, hepatocytes absorb blood-born Ad particles in a blood factor-dependent manner, serving as a second dominant mechanism mediating sequestration of blood-born Ad. However, when the Ad dose is high and both the Kupffer cells and blood-factor pathways are inactivated, sinusoid endothelial cells and the anatomical architecture of liver sinusoids become the third line of defense that sequesters Ad particles in an RGD motif-dependent manner.

To test this model and reduce to practice Ad variant capable of escaping of being sequestered in the liver after intravascular delivery, a set of mutated Ad5-based vectors was developed, where specific mutations ablating interactions with hepatic cells were introduced for some or all of the pathways mediating Ad trapping in the liver (FIG. 24). It is important to note that in the exemplary context of Ad5-based vectors, possessing individual mutations ablating only one or two of the mechanisms that mediate virus trapping in the liver, the sequestration of Ad particles in the liver after intravascular virus administration cannot be prevented. Indeed, Ad vectors ablated either for binding to blood coagulation factors due to T425A hexon mutation (Ad-TEA), or ablated for interaction with RGD-specific cellular integrins due to substitution of RGD penton loop for human laminin-derived peptide (Ad-Lam), or their combination in the single Ad-2M virus, containing both of these mutations simultaneously, all of these vectors were still trapped in the liver tissue one hour after intravenous virus injection as efficiently as non-modified wild type Ad5 virus, Ad-WT (FIG. 21C, SEQ ID No.: 1). However, the best way to carry the invention is the incorporation of the third and novel mutation in hexon HVR1 in addition to T425A hexon and Lam penton mutations into one and the same vector, Ad-3M, which revealed remarkable property of the resultant triple-mutant virus, which was able to escape liver sequestration following its intravascular injection (FIG. 23B).

In addition to its reduced sequestration in the liver tissue, intravenous injection of the triple-mutated Ad-3M vector exhibited remarkably lower inflammatory cytokine and chemokine activation in the spleen, compared to unmodified Ad-WT virus. Unlike unmodified Ad-WT vector, Ad-3M virus also failed to trigger rapid necrotic death of liver macrophages, Kupffer cells, providing direct evidence for greatly improved safety profile, compared to Ad5-WT (FIGS. 23D and 23E). These properties of the virus arise from mutations introduced into Ad5 penton which abrogate its interaction with cellular integrins (FIG. 18) and in hexon, which ablates virus interaction with coagulation factor FX (FIG. 15).

This study is the first demonstration of the Ad vector design for ablating the sequestration of blood-born Ad in the liver based on specific genetic inactivation of a defined set of mechanisms that control this process. The embodiments and specific examples of mutations simultaneously introduced into a single vector provide the rationale for the use of the vectors with liver-escaping properties as the platform for the development of tumor-targeted oncolytic viruses that are effective for the treatment of disseminated metastatic tumors via intravascular route of vector delivery.

x. Example 10: Cells and Viruses 293 (Human Embryonic Kidney, Microbix, Toronto Canada) cells for Ad propagation were grown in Dulbecco's Modified Eagle Medium (DMEM), supplemented with 10% fetal calf serum, 2 mM L-Glutamine and 1× Penicillin/Streptomycin solution (Invitrogen, Carlsbad, Calif.). Wild type human Ad serotypes Ad3 (GB strain, VR3); Ad14 (de Wit, VR1S), Ad16 (Ch.79, VR17), and Ad35 (Holden strain, VR-718) were purchased from the American Type Culture Collection. The human Ad5, possessing intact wild type Ad5 capsid, was constructed previously and is described in detail as Ad5GFP in. The Ad5-based vector Ad5/35S, with Ad35-derived fiber shaft and knob domains, was previously constructed and described as Ad5GFP/F35 in. The Ad5/35L, possessing Ad35-derived fiber knob domain, was previously constructed and described in. Ad5ΔRGD and Ad5/35ΔRGD are identical to Ad5 and Ad5/35L, but possess an RGD motif deletion in the penton base protein. These vectors were previously constructed and described in. Ad5*F and Ad5*FΔRGD were kindly provided by Dr. Ramon Alemany (Barcelona, Spain). Both of these Ad5-based vectors possess a single point Y477A amino acid mutation within the fiber knob domain that abrogates virus binding to CAR. Ad5*FΔRGD also possesses an RGD motif deletion within its penton base protein. Ad5 vector, expressing red fluorescent protein, was kindly provided by Dr. Michael Barry (Rochester, Minn.). All viruses were amplified in 293 cells under conditions preventing cross contamination. Viruses were banded in CsCl gradients; viral bands were collected, dialyzed and aliquoted as described elsewhere. Ad particle concentrations were determined spectrophotometrically by measuring the optical density at 260 nm (0D260), using the extinction coefficient for wild type Ad5, $A260=9.09\times10^{11}$ OD ml cm virion$^{-1}$.

xi. Example 11: Ad Infection In Vivo

All experimental procedures involving animals were conducted in accordance with the institutional guidelines set forth by the University of Washington. C57B1/6 mice were purchased from Charles River, Wilmington, Mass. B3-integrin knockout mice, β3-KO (stock #4669) and scavenger receptor A knock out mice (Msr1, stock #6096) were purchased from Jackson Laboratory, Bar Harbor, Me. All mice were housed in specific-pathogen-free facilities. All wild type viruses or Ad vectors were injected into the tail vein of mice at a dose of $10^{11}$ Ad particles (corresponds to $5\times10^9$ PFU of Ad5 vector determined on 293 cells) in 200 μl of phosphate buffered saline (PBS). For in vivo transduction studies, mice were sacrificed 1 or 48 hours post virus infusion and livers were processed for histological analyses. For analysis of Ad genome accumulation in the liver tissue 1 h and 24 h after Ad vector administration into the tail vein, blood was flushed from the liver by cardiac saline perfusion, livers were harvested, and total DNA was purified. To inactivate vitamin K-dependent blood coagulation factors, mice were injected with warfarin twice, 72 h and 24 h before Ad administration. Warfarin was resuspended in peanut oil and 150 μg of warfarin per mouse per injection were used as described elsewhere. To eliminate Kupffer cells from the liver, mice were injected with 200 μl of clodronate liposomes (Clodronateliposomes.org) 48 h before virus administration. Cl$_2$MDP (or clodronate) was a gift of Roche Diagnostics GmbH, Mannheim, Germany. To analyze Ad liver cell transduction by flow cytometry, liver cells were purified with collagenase perfusion and plated on Primaria 6-well plates 24 hours after intravenous virus injection. Next day, cells were detached from the plate using 2 mM EDTA solution and stained with anti-CD31 (endothelial cells), anti-β3-integrin (cells of hematopoietic origin, including Kupffer cells and circulating monocytes), or isotype control antibodies. Positive staining of cells was analyzed by flow cytometry.

xii. Example 12: Analysis of Ad-Kupffer Cell Interaction In Vivo

To analyze Ad interactions with Kupffer cells, $10^{10}$ virus particles were injected into the tail vein, and 60 min later, livers were flushed with saline via cardiac perfusion, harvested and immediately frozen in an OCT compound. Frozen liver sections were fixed and stained with rat anti-mouse F4/80 primary antibody (BD Biosciences, San Diego, Calif.) to detect Kupffer cells. Specific binding of primary antibodies was visualized with secondary anti-rat-Alexa Flour 488 antibody (Molecular Probes Inc., Eugene, Oreg.). To detect Ad particles, liver sections were stained with anti-hexon polyclonal antibody (Abcam, Cambridge, Mass.). The staining with biotinilated anti-hexon primary antibody was developed with secondary Cy3-labeled streptavidin. To detect platelets and endothelial cells on liver sections, antibodies to CD41 (platelets, clone MWReg30) or CD31-FITC (endothelial cells, clone MEC13.3 (both from BD Biosciences) were used. Cell nuclei were counterstained with 1 μg/ml 4',6-diamidino-2-phenylindole (DAPI) (Sigma, St. Louis, Mo.).

xiii. Example 13: Southern Blot Analyses

For analysis of Ad genomic DNA deposition and persistence in mouse livers, isolation of total liver DNA and Southern analysis were performed as described elsewhere. Briefly, at the indicated time points, livers were harvested and total liver DNA was isolated using DNA salting-out protocol, followed by phenol/chloroform and chloroform isoamyl alcohol purifications. Next, 10 μg of purified total liver DNA was digested with HindIII endonuclease overnight and loaded onto 1% agarose gel. After completion of electrophoretic separation of the DNA fragments, they were transfected onto a Hybond-XL membrane (GE Healthcare) and the membrane was hybridized with a 32P-labeled mouse β-glucuronidase (Gus) gene specific probe to ensure equivalent DNA loads. The image of Gus-specific hybridization was obtained by exposing the membrane to both a phosphorimager screen and an X-ray film. Next, the membrane was stripped off the Gus-specific probe and re-hybridized with an Ad-specific 32P-labeled probe (8 kb HindIII—A-fragment, corresponding to the E2 region of the Ad genome). The image of the hybridization reaction was obtained by exposing the membrane to a phosphorimager screen and an X-ray film. The intensity of Gus- and Ad-specific signals in phosphorimager-collected images were analyzed using manufacturer's software.

xiv. Example 14: Proteome Profiler Antibody Arrays

A "Proteome Profiler antibody array: Mouse Cytokine Array Panel A" (#ARY006, R&D System) was used, according to the manufacturer's instructions. Each spleen was homogenized in 2 ml of sample solution, and 1 ml (½ spleen) was used to incubate with each membrane on a rocking platform overnight. Membranes were developed with ImmunoStar HRP-substrate (BioRad, #1705041).

xv. Example 15: RNAse Protection Assay

Total RNA was extracted from tissues using the "RNAqueous-Midi kit" (Ambion Inc., Austin, Tex.). Ten μg of RNA were hybridized with a mix of 32P-labeled RNA probes. The 32P-labeled RNA probe mix was prepared by in vitro transcription using the "In vitro transcription kit", CK-3, and custom template sets were provided by BD Biosciences/Pharmingen (San Diego, Calif.). The hybridized RNAs were treated with RNAse, using the "RNAse protection Assay kit" (BD Biosciences), precipitated and the protected fragments were resolved on vertical sequencing (10% acrylamide) gels. Following electrophoresis, the gels were dried and exposed to X-ray film (Kodak-X-Omat) and PhosphorImager screen (Molecular Dynamics, Sunnyvale, Calif.). The signals on the screen were analyzed by PhosphorImager Image-Quant software. The RNAse protection assay was performed using RNA samples of at least 3 to 5 individual mice per each virus. At least two independently prepared virus stocks were used for RNA levels analysis.

xvi. Example 16: Immunohistochemical and Immunofluorescence Stainings

Mice were anaesthetized, and spleens and livers were collected, frozen in O.C.T. compound and stored at −80° C. until processed. Six to eight micron sections were cut, air dried, fixed for 10 minutes in acetone at −20° C., air dried for at least 4 hours, re-hydrated in TBS for one hour, blocked in 2% N.S. for 1 hour and incubated with primary antibodies overnight at 4° C. with or without 0.1% saponin depending on the antigen. Then, sections were incubated with HRP-labeled secondary antibodies for 1 hour. Slides were developed with ImmPact DAB or NovaRed substrates (Vector Laboratories), air dried, mounted, and analyzed on a Leica microscope. For immunofluorescence stainings, slides were immediately mounted after washing the secondary antibodies. Confocal imaging was done on a Zeiss 510 Meta Confocal microscope.

xvii. Example 17: Statistical Analysis

All statistical analyses were done using an unpaired two sided Student's t-test on Instat software. The data are expressed as means ±/−s.d. The number of animals used in the experiments for each individual condition varied from 3 to 5.

e. REFERENCES CITED

| U.S. PATENT DOCUMENTS | | | |
|---|---|---|---|
| 5,712,136 | Wickham et at, | January 1998 | 435/456 |

OTHER PUBLICATIONS

Alemany, R., and Curiel, D. T. (2001). CAR-binding ablation does not change biodistribution and toxicity of adenoviral vectors. Gene Ther 8, 1347-1353.

Alemany, R., Suzuki, K., and Curiel, D. T. (2000). Blood clearance rates of adenovirus type 5 in mice. The Journal of general virology 81, 2605-2609.

Alonso-Padilla, J., Papp, T., Kajan, G. L., Benko, M., Havenga, M., Lemckert, A., Harrach, B., and Baker, A. H. (2015). Development of Novel Adenoviral Vectors to Overcome Challenges Observed With HAdV-5-based Constructs. Mol Ther.

Baker, A., McVey, J H, Waddington, S N, Di Paolo, N C, Shayakhmetov, D M. (2007). The influence of blood on in vivo adenovirus bio-distribution and transduction. Mol Ther, epub (ahead of print).

Baker, A. H., Nicklin, S. A., and Shayakhmetov, D. M. (2013). FX and Host Defense Evasion Tactics by Adenovirus. Molecular Therapy 21, 1109-1111.

Barouch, D. H., Kik, S. V., Weverling, G. J., Dilan, R., King, S. L., Maxfield, L. F., Clark, S., Ng'ang'a, D., Brandariz, K. L., Abbink, P., et al. (2011). International seroepidemiology of adenovirus serotypes 5, 26, 35, and 48 in pediatric and adult populations. Vaccine 29, 5203-5209.

Bergelson, J. M., Cunningham, J. A., Droguett, G., Kurt-Jones, E. A., Krithivas, A., Hong, J. S., Horwitz, M. S., Crowell, R. L., and Finberg, R. W. (1997). Isolation of a common receptor for Coxsackie B viruses and adenoviruses 2 and 5. Science 275, 1320-1323.

Bradley, R. R., Lynch, D. M., Iampietro, M. J., Borducchi, E. N., and Barouch, D. H. (2012). Adenovirus serotype 5 neutralizing antibodies target both hexon and fiber following vaccination and natural infection. J Virol 86, 625-629.

Brunetti-Pierri, N., Palmer, D. J., Beaudet, A. L., Carey, K. D., Finegold, M., and Ng, P. (2004). Acute toxicity after high-dose systemic injection of helper-dependent adenoviral vectors into nonhuman primates. Hum Gene Ther 15, 35-46.

Di Paolo N C, B. L., Irons EE, Papayannopoulou T, Tomlinson S, Shayakhmetov DM (2014). IL-1a and complement cooperate in triggering local neutrophilic inflammation in response to adenovirus and eliminating virus-containing cells. PLoS Pathogens DOI: 10.1371/journal.ppat.1004035.

Di Paolo, N. C., Doronin, K., Baldwin, L. K., Papayannopoulou, T., and Shayakhmetov, D. M. (2013). The Transcription Factor IRF3 Triggers "Defensive Suicide" Necrosis in Response to Viral and Bacterial Pathogens. Cell Reports 3, 1840-1846.

Di Paolo, N. C., Miao, E. A., Iwakura, Y., Murali-Krishna, K., Aderem, A., Flavell, R. A., Papayannopoulou, T., and Shayakhmetov, D. M. (2009a). Virus binding to a plasma membrane receptor triggers interleukin-1 alpha-mediated proinflammatory macrophage response in vivo. Immunity 31, 110-121.

Di Paolo, N. C., van Rooijen, N., and Shayakhmetov, D. M. (2009b). Redundant and Synergistic Mechanisms Control the Sequestration of Blood-born Adenovirus in the Liver. Molecular Therapy 17, 675-684.

Doronin, K., Flatt, J. W., Di Paolo, N. C., Khare, R., Kalyuzhniy, O., Acchione, M., Sumida, J. P., Ohto, U., Shimizu, T., Akashi-Takamura, S., et al. (2012). Coagulation factor X activates innate immunity to human species C adenovirus. Science 338, 795-798.

Gaggar, A., Shayakhmetov, D., and Lieber, A. (2003). CD46 is a cellular receptor for group B adenoviruses. Nature Medicine 9, 1408-1412.

Graham, F. L., and van der Eb, A. J. (1973). A new technique for the assay of infectivity of human adenovirus 5 DNA. Virology 52, 456-467.

Haisma, H. J., Kamps, J. A., Kamps, G. K., Plantinga, J. A., Rots, M. G., and Bellu, A. R. (2008). Polyinosinic acid enhances delivery of adenovirus vectors in vivo by preventing sequestration in liver macrophages. The Journal of general virology 89, 1097-1105.

Kalyuzhniy, O., Di Paolo, N. C., Silvestry, M., Hofherr, S. E., Barry, M. A., Stewart, P. L., and Shayakhmetov, D. M. (2008). Adenovirus serotype 5 hexon is critical for virus infection of heptocytes in vivo. Proceedings of the National Academy of Sciences of the United States of America 105, 5483-5488.

Khare, R., Chen, C. Y., Weaver, E. A., and Barry, M. A. (2011a). Advances and future challenges in adenoviral vector pharmacology and targeting. Curr Gene Ther 11, 241-258.

Khare, R., Hillestad, M. L., Xu, Z., Byrnes, A. P., and Barry, M. A. (2013). Circulating antibodies and macrophages as modulators of adenovirus pharmacology. J Virol 87, 3678-3686.

Khare, R., May, S. M., Vetrini, F., Weaver, E. A., Palmer, D., Rosewell, A., Grove, N., Ng, P., and Barry, M. A. (2011b).

Generation of a Kupffer cell-evading adenovirus for systemic and liver-directed gene transfer. Mol Ther 19, 1254-1262.

Kojaoghlanian, T., Flomenberg, P., and Horwitz, M. S. (2003). The impact of adenovirus infection on the immunocompromised host. Rev Med Virol 13, 155-171.

Lieber, A., He, C. Y., Meuse, L., Schowalter, D., Kirillova, I., Winther, B., and Kay, M. A. (1997). The role of Kupffer cell activation and viral gene expression in early liver toxicity after infusion of recombinant adenovirus vectors. J Virol 71, 8798-8807.

Manickan, E., Smith, J. S., Tian, J., Eggerman, T. L., Lozier, J. N., Muller, J., and Byrnes, A. P. (2006). Rapid Kupffer cell death after intravenous injection of adenovirus vectors. Molecular Therapy 13, 108-117.

Nemerow, G. R. (2000). Cell receptors involved in adenovirus entry. Virology 274, 1-4.

Nemerow, G. R., and Stewart, P. L. (1999). Role of alpha(v) integrins in adenovirus cell entry and gene delivery. Microbiol Mol Biol Rev 63, 725-734.

Parker, A. L., Waddington, S. N., Nicol, C. G., Shayakhmetov, D. M., Buckley, S. M., Denby, L., Kemball-Cook, G., Ni, S. H., Lieber, A., McVey, J. H., et al. (2006). Multiple vitamin K-dependent coagulation zymogens promote adenovirus-mediated gene delivery to hepatocytes. Blood 108, 2554-2561.

Raper, S. E., Chirmule, N., Lee, F. S., Wivel, N. A., Bagg, A., Gao, G. P., Wilson, J. M., and Batshaw, M. L. (2003). Fatal systemic inflammatory response syndrome in a ornithine transcarbamylase deficient patient following adenoviral gene transfer. Mol Genet Metab 80, 148-158.

Raper, S. E., Yudkoff, M., Chirmule, N., Gao, G. P., Nunes, F., Haskal, Z. J., Furth, E. E., Propert, K. J., Robinson, M. B., Magosin, S., et al. (2002). A pilot study of in vivo liver-directed gene transfer with an adenoviral vector in partial ornithine transcarbamylase deficiency. Hum Gene Ther 13, 163-175.

Roberts, D. M., Nanda, A., Havenga, M. J. E., Abbink, P., Lynch, D. M., Ewald, B. A., Liu, J., Thorner, A. R., Swanson, P. E., Gorgone, D. A., et al. (2006). Hexon-chimaeric adenovirus serotype 5 vectors circumvent pre-existing anti-vector immunity. Nature 441, 239-243.

Roelvink, P. W., Lizonova, A., Lee, J. G., Li, Y., Bergelson, J. M., Finberg, R. W., Brough, D. E., Kovesdi, I., and Wickham, T. J. (1998). The coxsackievirus-adenovirus receptor protein can function as a cellular attachment protein for adenovirus serotypes from subgroups A, C, D, E, and F. J Virol 72, 7909-7915.

Shayakhmetov, D. M., Gaggar, A., Ni, S. H., Li, Z. Y., and Lieber, A. (2005). Adenovirus binding to blood factors results in liver cell infection and hepatotoxicity. Journal of Virology 79, 7478-7491.

Shayakhmetov, D. M., Li, Z. Y., Ni, S., and Lieber, A. (2004). Analysis of adenovirus sequestration in the liver, transduction of hepatic cells, and innate toxicity after injection of fiber-modified vectors. J Virol 78, 5368-5381.

Shenk, T. (1996). Adenoviridea. In Fields Virology, B. N. Fields, Knipe, D. M., Howley, P. M., ed. (Philadelphia: Lippincott-Raven Publisher), pp. 2111-2148.

Shenk, T. (2001). Adenoviridae. in Field's Virology (D. M. Nipe and P. M. Howley, Eds.), 2265-2328.

Thomas, C. E., Ehrhardt, A., and Kay, M. A. (2003). Progress and problems with the use of viral vectors for gene therapy. Nature Reviews Genetics 4, 346-358.

Waddington, S. N., Mcvey, J. H., Bhella, D., Parker, A. L., Barker, K., Atoda, H., Pink, R., Buckley, S. M. K., Greig, J. A., Denby, L., et al. (2008). Adenovirus serotype 5 hexon mediates liver gene transfer. Cell 132, 397-409.

Wickham, T. J., Mathias, P., Cheresh, D. A., and Nemerow, G. R. (1993). Integrins alpha v beta 3 and alpha v beta 5 promote adenovirus internalization but not virus attachment. Cell 73, 309-319.

Wolff, G., Worgall, S., van Rooijen, N., Song, W. R., Harvey, B. G., and Crystal, R. G. (1997). Enhancement of in vivo adenovirus-mediated gene transfer and expression by prior depletion of tissue macrophages in the target organ. J Virol 71, 624-629.

Worgall, S., Wolff, G., Falck-Pedersen, E., and Crystal, R. G. (1997). Innate immune mechanisms dominate elimination of adenoviral vectors following in vivo administration. Hum Gene Ther 8, 37-44.

What is claimed:

1. A method of delivering a gene to a non-hepatic mammalian cell in a subject, comprising the steps of:
   administering to the subject an effective amount of an adenovirus comprising:
   a mutation in the RGD motif of the penton protein, wherein the mutation causes reduced binding of β3 integrins of a host cell;
   a mutation in the HVR1 region of the hexon protein, wherein the mutation causes reduced virus trapping in Kupffer cells; and
   a mutation in the HVR7 region of the hexon protein, wherein the combination of the mutation in the RGD motif, the mutation in the HVR1 region and the mutation in the HVR7 region causes reduced liver sequestration of the adenovirus.

2. The method of claim 1, wherein the RGD motif of the penton protein is substituted with a non-RGD motif-containing peptide, capable of binding to non-β3 cellular integrins.

3. The method of claim 1, wherein the adenovirus is a species B, C, or D adenovirus.

4. The method of claim 1, wherein the adenovirus is serotype 5 or 2.

5. The method of claim 1, wherein the adenovirus further comprises a mutation in the HVR3 or HVR5 region of the hexon protein.

6. The method of claim 5, wherein the mutation in the HVR3 or HVR5 region of the hexon protein is a substitution.

7. The method of claim 1, wherein the adenovirus comprises a single virus genomic DNA molecule comprising a nucleotide sequence that encodes SEQ ID NO: 2.

8. The method of claim 1, wherein the mutation in the HVR1 region of the hexon protein is a substitution.

9. The method of claim 1, wherein the adenovirus comprises a gene of interest that encodes a polypeptide selected from the group consisting of cytokines, cellular receptors, nuclear receptors, ligands, coagulation factors, CFTR proteins, insulins, dystrophins, growth hormones, immunestimulatory or immune-suppressing proteins of eukaryotic or prokaryotic origin, enzymes, enzyme inhibitors, polypeptides with antitumor effect, polypeptides capable of inhibiting a bacterial, parasitic or viral infection, antibodies, toxins, immunotoxins, ribozymes, and markers.

10. The method of claim 1, wherein the adenovirus comprises a single virus genomic DNA molecule comprising a nucleotide sequence that encodes SEQ ID NO:3 or SEQ ID NO:4.

11. The method of claim 1, wherein the adenovirus is administered intravenously.

12. The method of claim 1, wherein the adenovirus is a replication-competent adenovirus.

13. The method of claim 1, wherein the adenovirus comprises a gene encoding a shRNA or a LncRNA.

* * * * *